United States Patent
Rossi et al.

(10) Patent No.: US 9,353,374 B2
(45) Date of Patent: May 31, 2016

(54) RNA APTAMERS AGAINST BAFF-R AS CELL-TYPE SPECIFIC DELIVERY AGENTS AND METHODS FOR THEIR USE

(71) Applicant: CITY OF HOPE, Duarte, CA (US)

(72) Inventors: John Rossi, Duarte, CA (US); Katrin Tiemann, Pasadena, CA (US); Jiehua Zhou, Monrovia, CA (US); Britta Vallazza, Hagen (DE)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/685,486

(22) Filed: Apr. 13, 2015

(65) Prior Publication Data
US 2016/0076036 A1    Mar. 17, 2016

Related U.S. Application Data

(60) Division of application No. 13/651,265, filed on Oct. 12, 2012, now Pat. No. 9,006,416, which is a continuation of application No. PCT/US2011/032385, filed on Apr. 13, 2011.

(60) Provisional application No. 61/323,761, filed on Apr. 13, 2010.

(51) Int. Cl.
| | |
|---|---|
| *C12N 15/11* | (2006.01) |
| *C12N 15/113* | (2010.01) |
| *C12N 15/115* | (2010.01) |
| *A61K 47/48* | (2006.01) |
| *A61K 31/713* | (2006.01) |

(52) U.S. Cl.
CPC .......... *C12N 15/1135* (2013.01); *A61K 31/713* (2013.01); *A61K 47/48092* (2013.01); *C12N 15/115* (2013.01); *C12N 2310/14* (2013.01); *C12N 2310/3519* (2013.01); *C12N 2320/32* (2013.01)

(58) Field of Classification Search
CPC ............. C12N 15/115; C12N 2310/14; C12N 2310/16; C12N 2310/3519
See application file for complete search history.

(56) References Cited

U.S. PATENT DOCUMENTS

| | | | | |
|---|---|---|---|---|
| 8,030,290 | B2 * | 10/2011 | Rossi ................. | C12N 15/1132 514/44 R |
| 8,222,226 | B2 * | 7/2012 | Rossi ................. | C12N 15/1132 514/44 A |
| 2008/0214436 | A1 * | 9/2008 | Yu ...................... | A61K 31/7105 514/1.1 |

OTHER PUBLICATIONS

McNamara et al. Nat. Biotechnol. 2006, 24: 1005-15.*
Lyu et al. Mol. Cancer Ther. 2007, 6: 460-70.*

\* cited by examiner

*Primary Examiner* — Brian Whiteman
(74) *Attorney, Agent, or Firm* — Perkins Coie LLP; Lara Dueppen

(57) ABSTRACT

In one embodiment, a B cell specific aptamer-siRNA chimera is provided. The B cell specific aptamer-siRNA chimera may include an RNA aptamer that binds BAFF-R and an siRNA molecule conjugated to the RNA aptamer via a nucleotide linker. In another embodiment, a B cell specific RNA aptamer is provided. The RNA aptamer may be a molecule that binds to BAFF-R that has the sequence SEQ ID NO:37, SEQ ID NO:38 or SEQ ID NO:39. In some embodiments, the RNA aptamer is conjugated, via a nucleotide linker, to an siRNA molecule that suppresses expression of one or more target oncogenes in one or more B cells. In one aspect, the one or more target oncogenes are selected from Bcl6, Bcl2, STAT3, Cyclin D1, Cyclin E2 and c-myc. In another embodiment, methods for treating a B cell malignancy in a cancer patient are provided. Such methods may include administering a therapeutically effective amount of a therapeutic composition, the therapeutic composition comprising a B cell specific RNA aptamer that binds BAFF-R.

20 Claims, 64 Drawing Sheets

| Groups | Fixed sequence GGGAGGACGAUGCGG | | Frequency (170 sequences) of BAFF-R pool | Fixed sequence CAGACGACUCGCCCGA | SEQ ID NO |
|---|---|---|---|---|---|
| Group 1 Total 43 25.2% | Conserved domain: | R-1 | GAGGCUCAACAAUGAUAGAGCCCGCAAUGUUGAUGAGUUGCCAGUCUG | 19 (11.2%) | 14 |
| | | R-2 | GAGGCUCGGCUUAGUAAGUAAGAUUGAGCCGCAUGACGCUCCGAGUCUG | 5 (2.9%) | 15 |
| | | R-3 | GGAGGCUCUUAGAGCCCUGCAUCUUGGAAAAUAGGAUAAGGCCCGUGAC | 4 (2.4%) | 16 |
| | GAGGCUC 27.8% | R-4 | GAGGCUCGUGGAUGUUUAUCGAAGAGCCGCAAUCCGGUUUGUCUGGUG | 4 (2.4%) | 17 |
| | | R-5 | GAGGUUCGUCAUAUAGGGGUACUGAACCCGCGUCGGUGUUCGGUUUGGC | 1 | 18 |
| | | R-6 | UGAGGCUCAUAGAGCACCGCAAAGAUAGAAGUUUGUUGCCAUCGAUAGU | 5 (2.9%) | 19 |
| | | R-7 | UGAGGCUCGAUUAGAGGGUUGGUCUCUUGUGAGCCCGUAUCGGAAUGCUG | 1 | 20 |
| | | R-8 | UUUUGAGGCUCGCGACUACGAAGAGCAAACCGUAUCGCGUUGCAGCAUGA | 4 (2.4%) | 21 |
| Group 2 Total 26 15.3% | UUUCCC/ | R-9 | CAGGUUUCCCGUUUGUCGGUUCAAACGGCGUCCUGCCGUUAGUUGGUGUG | 14 (8.2%) | 22 |
| | GGCGUCC | R-10 | UUUCCCGGCCAAGUAGCUGGGCGUCCGCAUUCCUCAGGACCGUACGCCG | 11 (6.5%) | 23 |
| | | R-11 | UUUCCCUAGGACAUCGAUCUUAGGCGUCCGCACGUCAACCUCCCGUG | 1 | 24 |
| Group 3 Total 7 | AAUCGC(C)G(R-12 U)AAU | | AAUCGCGAAUGAGGCUCUUAGAGCAUUCGGCGCGCAAACCAGGACACGC | 4 (2.4%) | 25 |
| | | R-13 | UCAAUCGCGUAAUAACGCGUUUGUGAACUGAAUCCGGUCUGAGGUG | 3 (1.8%) | 26 |
| Group 4 Total 6 | AUA(G)ACU | R-14 | AUAACUAUUGUGCUAGAGGGCUUAUUAUUGAGCCGGUUGAUAGUUGCG | 5 (2.9%) | 27 |
| | | R-15 | AUGACUGACAGGGACUUCUUGGCAAUUUUGCUGCGGAGUUCACGGUGGCGC | 1 | 28 |
| Group 5 | | R-16 | UUUACUGACCGUUUUGUAGGUAGCCUUGCUCACAAGAAGUGUGGCG | 6 (3.5%) | 29 |
| Group 6 | | R-17 | GACUUAGAUGUCACGUUGUAUAAAUCGGUCGUCCUCUGUUACGCUGGCUG | 2 | 30 |
| Group 7 | | R-18 | GAUAGGACAUGCGGAUUCCGUUGUGUUUACGUGUUACUCAGGUCUGGC | 2 | 31 |
| Group 8 | | R-19 | UUGAUUGUAAGAAUUGUGCAAUGUGCAUUUCAOCUCUAGCAACGUGAC | 3 (1.8%) | 32 |
| Group 9 | | R-20 | CUUAUGGUCUUUAUGUGUUUUUUUUCUCCGACCCGCCGGUUCUUGGUCUGC | 2 | 33 |
| Group 10 | UGUCCG | R-21 | UGUCCGAAUCCGAGAAACGGGAUCCCGCGUCCGGCGUCAUGUAGUUGGU | 3 (1.8%) | 34 |
| Group 11 | ATCC | R-22 | AUCCUCCGAAGGUCGCGCCAACGUCACACAUUAAGCUUUUGUUCGUCUG | 2 | 35 |
| Others | | | Orphan sequences | 68 | n/a |

Figure 14

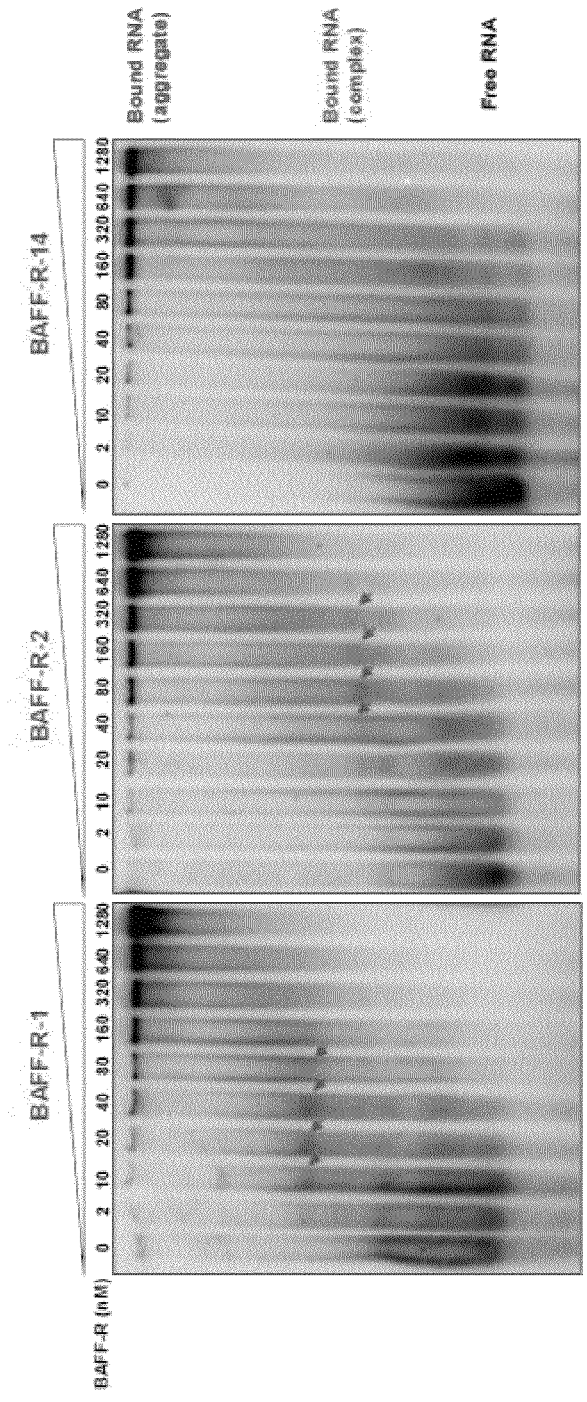
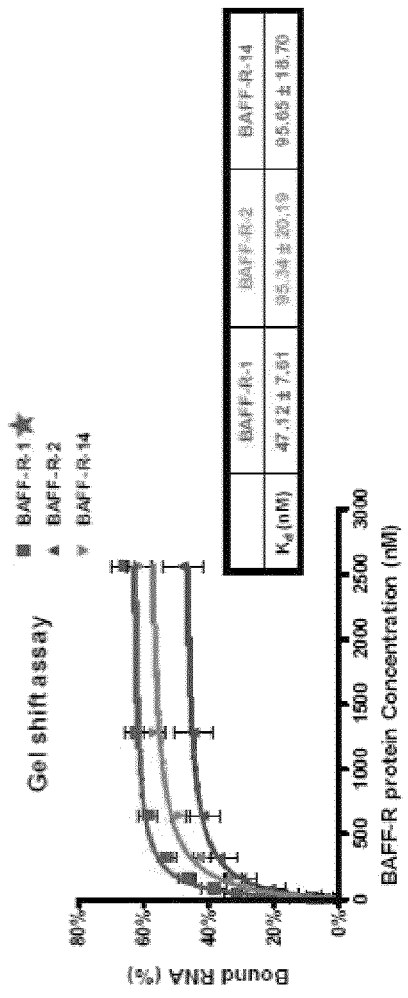
Fig. 16A
Fig. 16B

Over-expression of BAFF-R

SELEX-1 (25°C)

| Round | Target/RNA ratio | Target (pmol) | RNA (pmol) | t-RNA (pmol) | Binding (%) | DNA (µg) |
|---|---|---|---|---|---|---|
| 1 hot | 1:1 | 1700 | 1700 | - | 5,7 | 3 |
| 1 cold | 1:1 | 2000 | 2000 | - | | |
| 2 | 1:5 | 150 | 750 | 250 | 1,8 | 3 |
| 2 repeat 1 | 1:5 | 200 | 1000 | 250 | 1,2 | 0,66 |
| 1 repeat 1 | 1:5 | 400 | 2000 | - | 1,7 | 1,5 |
| 1 repeat 2 | 1:5 | 400 | 2000 | - | 1,2 | 13 |
| 2 repeat 2 | 1:5 | 200 | 1000 | - | 1,9 | 13 |
| 3 | 1:7,5 | 140 | 1000 | 250 | 1,3 | 13 |
| 4 | 1:7,5 | 140 | 1000 | 500 | 1,1 | 14 |
| 5 | 1:7,5 | 100 | 750 | 500 | 1,3 | 10 |
| 5 repeat | 1:7,5 | 100 | 750 | 500 | 1,2 | 9,6 |
| 6 | 1:7,5 | 100 | 750 | 500 | 1,3 | 14,2 |
| 7 | 1:7,5 | 100 | 750 | 1000 | 1,6 | 16,4 |
| 8 | 1:7,5 | 100 | 750 | 1000 | 2,9 | 15,4 |
| 9 | 1:10 | 75 | 750 | 1000 | 3,5 | 11,9 |
| 10 | 1:10 | 75 | 750 | 2000 | 7,3 | 17,6 |
| 11 | 1:10 | 50 | 500 | 3000 | 8,9 | 15 |
| 12 | 1:10 | 50 | 500 | 4000 | 10,1 | 10 |
| 12 F | 1:10 | 50 | 500 | 4000 | 1,7 | |

SELEX-2 (37°C)

| Round | Target/RNA ratio | Target (pmol) | RNA (pmol) | t-RNA (pmol) | Binding (%) | DNA (µg) |
|---|---|---|---|---|---|---|
| 4 | 1:7,5 | 100 | 750 | 250 | 1,3 | 10,5 |
| 5 | 1:10 | 75 | 750 | 500 | 1,9 | 13,8 |
| 6 | 1:10 | 75 | 750 | 1000 | 2,6 | 9 |
| 7 | 1:10 | 50 | 500 | 2000 | 6,7 | 14,8 |
| 8 | 1:10 | 40 | 500 | 4000 | 6,7 | |
| 7 F | 1:7,5 | 100 | 750 | 1000 | 0,7 | |
| 8 F | 1:7,5 | 100 | 750 | 1000 | | |
| 9 F | | | | | | |
| 10 F | | | | | | |

Figure 36

Jeko-1

Rec-1

Z138

Granta 519

Rec-1

Z138

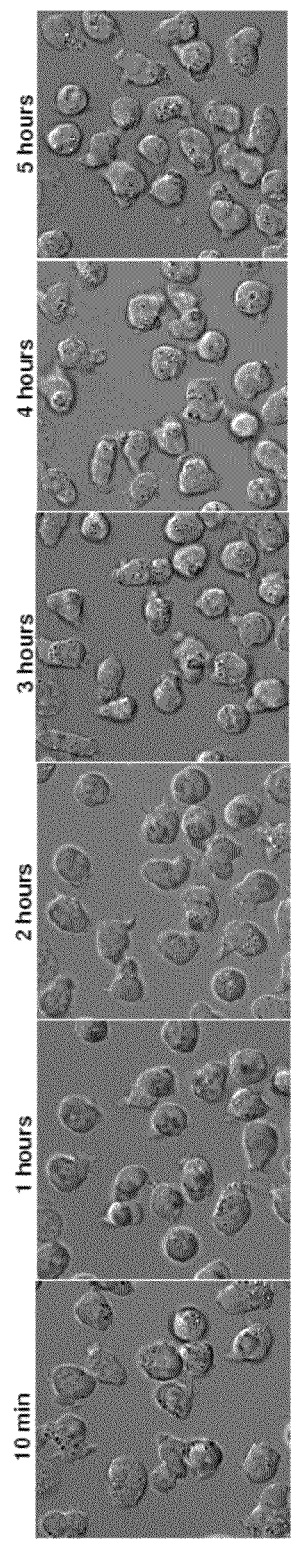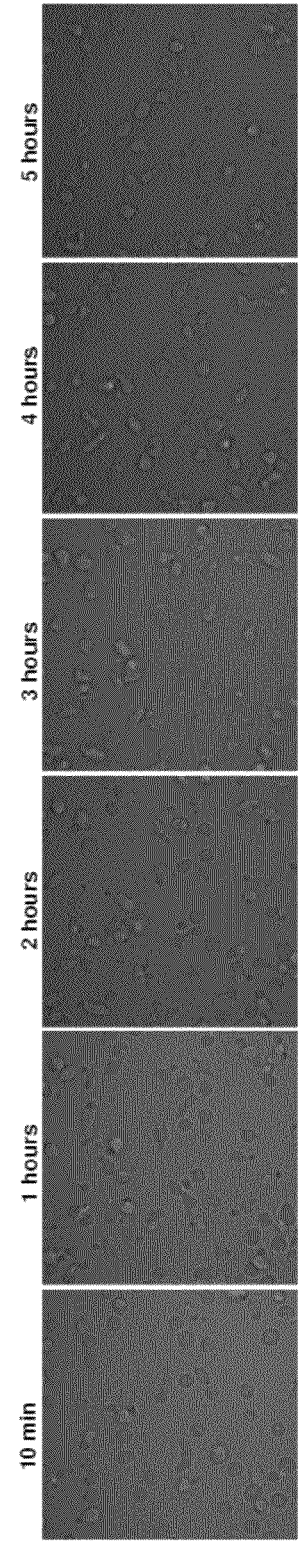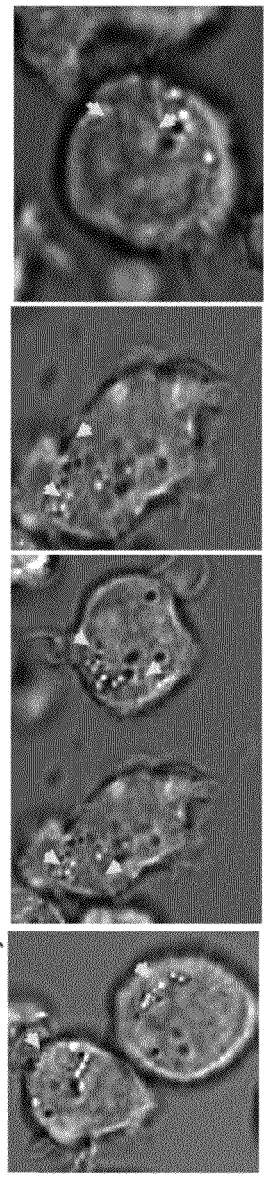
Fig. 41A
Fig. 41B
Fig. 41C

Jeko-1

Z138

(Z138)

(Jeko-1)

Fig. 57A

| Rank | Probe ID/ Gene Symbol | Fold-Change |
|---|---|---|
| 43 | LOC440173 | 1.8 |
| 46 | DNAH14 | 1.8 |
| 55 | LIPK | 1.7 |
| 59 | KRTAP9-3 | 1.7 |
| 67 | SNORD77 | 1.6 |
| 71 | OR5M3 | 1.6 |
| 75 | IL10 | 1.6 |
| 81 | LOC440925 | 1.5 |
| 84 | C15orf29 | 1.5 |
| 85 | MIR21 | 1.5 |

Fig. 57B

| Rank | Probe ID / Gene Symbol | Fold-Change |
|---|---|---|
| 11 | BTBD11 | -1.9 |
| 14 | LOC653543 | -1.8 |
| 21 | FAM129C | -1.6 |
| 26 | CTD-2514C3.1 | -1.6 |
| 27 | LOC284805 | -1.6 |
| 30 | LOC158572 | -1.5 |
| 33 | LOC729173 | -1.5 |
| 36 | S100A4 | -1.5 |
| 40 | RIMBP3C | -1.5 |
| 44 | CCIN | -1.5 |

Fig. 58A

| Rank | Probe ID / Gene Symbol | Fold-Change |
|---|---|---|
| 16 | KRTAP9-3 | 1.5 |
| 19 | GJA5 | 1.5 |
| 21 | ZNF434 | 1.5 |
| 24 | ANKRD20B | 1.4 |
| 30 | DNAJB14 | 1.4 |
| 32 | CA3 | 1.4 |
| 33 | NOL7 | 1.4 |
| 35 | ADRA1A | 1.4 |
| 36 | OR5M3 | 1.3 |
| 37 | FOXK2 | 1.3 |

Fig. 58B

| Rank | Probe ID / Gene Symbol | Fold-Change |
|---|---|---|
| 5 | BTBD11 | -2.2 |
| 12 | LOC158572 | -1.5 |
| 15 | MGC24103 | -1.5 |
| 18 | UTS2D | -1.4 |
| 19 | FAM18B2 | -1.4 |
| 22 | PDE6G | -1.4 |
| 23 | C6orf10 | -1.4 |
| 27 | FLJ11710 | -1.3 |
| 28 | ACTL8 | -1.3 |
| 29 | KCNV1 | -1.3 |

Fig. 59A

| Rank | Probe ID / Gene Symbol | Fold-Change |
|---|---|---|
| 11 | SNORD77 | 1.9 |
| 20 | IL10 | 1.6 |
| 26 | NOL7 | 1.5 |
| 28 | OR2M7 | 1.5 |
| 34 | C15orf29 | 1.5 |
| 36 | ZFP14 | 1.4 |
| 37 | ARRDC3 | 1.4 |
| 40 | SNORD54 | 1.4 |
| 41 | CXorf25 | 1.4 |
| 49 | SAMD9L | 1.4 |

Fig. 59B

| Rank | Probe ID / Gene Symbol | Fold-Change |
|---|---|---|
| 12 | DTX2 | -1.5 |
| 13 | ACTL8 | -1.5 |
| 14 | RIMBP3C | -1.5 |
| 19 | OR1L3 | -1.4 |
| 22 | FAM18B2 | -1.4 |
| 23 | MGC24103 | -1.4 |
| 25 | REEP4 | -1.4 |
| 26 | CECR2 | -1.3 |
| 28 | C21orf30 | -1.3 |
| 30 | CD24 | -1.3 |

Fig. 60A

| Rank | Probe ID / Gene Symbol | Fold-Change |
|---|---|---|
| 17 | ZNF434 | 1.6 |
| 20 | CA3 | 1.5 |
| 21 | NCOA1 | 1.5 |
| 23 | NOL7 | 1.5 |
| 24 | EXOC5 | 1.5 |
| 29 | IL10 | 1.5 |
| 30 | HSDL2 | 1.4 |
| 31 | SAMD9L | 1.4 |
| 32 | SNORD77 | 1.4 |
| 33 | ALPK2 | 1.4 |

Fig. 60B

| Rank | Probe ID / Gene Symbol | Fold-Change |
|---|---|---|
| 5 | LOC158572 | -1.8 |
| 12 | GUCA1C | -1.6 |
| 14 | LOC729173 | -1.6 |
| 18 | FLJ25758 | -1.5 |
| 22 | LOC653543 | -1.5 |
| 25 | HMGB3L1 | -1.4 |
| 26 | PP2672 | -1.4 |
| 27 | KLHL38 | -1.4 |
| 28 | GIMAP5 | -1.4 |
| 29 | MGC24103 | -1.4 |

RNA APTAMERS AGAINST BAFF-R AS CELL-TYPE SPECIFIC DELIVERY AGENTS AND METHODS FOR THEIR USE

PRIORITY CLAIM

This application is a divisional application of U.S. application Ser. No. 13/651,265, filed Oct. 12, 2012, which is a continuation application of International Application No. PCT/US2011/032385, filed Apr. 13, 2011, which claims priority to U.S. Provisional Patent Application No. 61/323,761, filed Apr. 13, 2010, the subject matter of all of which is hereby incorporated by reference in its entirety, as if fully set forth herein.

STATEMENT REGARDING FEDERALLY SPONSORED RESEARCH

The invention was made with Government support under Grant No. AI29329 awarded by the National Institutes of Health (NIH). The Government has certain rights in the invention.

BACKGROUND

Non-Hodgkin's Lymphoma (NHL) killed 20,000 people in 2009 and 66,000 new cases were identified (Jemal et al. 2009). NHL comprises a group of heterogeneous lymphoid malignancies for which conventional chemo- and radiotherapy approaches are rarely curative and many lymphomas relapse within the first year. Newer drugs such as proteasome, cell-cycle-dependent kinase and histone deacetylase inhibitors show promising results in lymphoma therapy, but are non-specific, thereby causing unwanted effects in non-lymphoma tissues such as nausea, vomiting, diarrhea, dehydration, cardiac dysrhythmias, myelosuppression, deep vein thrombosis, pulmonary embolism, and neuropathy. Therefore, a more targeted approach is needed.

Most NHLs are of B cell origin (Kueppers 2005). Diffuse Large B Cell Lymphoma (DLBCL) is the most common type of NHL (Mackay & Schneider 2009). Other lymphoma subtypes often transform into it when they progress. Patients treated with chemo- or radiotherapy often in combination with Rituxumab often respond well initially (Friedberg & Fisher 2008), nevertheless, approximately 50% of DLBCL patients relapse within 2 to 3 years of treatment and require additional therapy such as stem cell transplantation, which is often not curative (Friedberg & Fisher 2008; Feugier et al. 2005; Friedberg & Fisher 2006). Representing 6% of all NHL, Mantle cell lymphoma (MCL) is a relatively rare cancer. However, the clinical evolution of MCL is aggressive, with the lowest 5 year survival rate of any type of lymphoma, and is characterized with poor response to conventional therapeutic regimens (Campo et al. 1999).

A feature of many types of B cell lymphomas is the constitutive expression of oncogenes. Oncogenes are transcription factors, anti-apoptotic genes or genes involved in the cell cycle that are the result of reciprocal chromosomal translocation and mutations. When overexpressed, such genes result in uncontrolled cell proliferation, survival of malignant cells and protection against ionizing radiation and many commonly used chemotherapeutics (Kueppers 2005). Many NHLs, including MCL and DLBCL overexpress genes such as Bcl6, STAT3, c-myc, Bcl2, syk, and Cyclin family members such as Cyclin D1, Cyclin D2 and Cyclin E2 (Monti et al. 2005, Shaffer et al. 2006).

Anti-apoptotic Bcl2 gene is translocated in 85% of follicular lymphoma and in 15-30% of DLBCL (Bakhshi et al. 1985). Its overexpression correlates with poor prognosis in NHL patients due to the prolonged survival of the cancer cells (Reed 1996). Additionally, there is evidence that elevated expression of Bcl2 confers multidrug resistance to cells (Makin and Hickman 2000, Domen et al. 1998) and thus provides protection against radiation therapy and commonly used chemotherapeutics.

In 15% of DLBCL and 100% of Burkitt's lymphoma, the oncogene c-myc shows genetic alterations. Cyclin D1 (CCND1), which is involved in cell cycle regulation, is translocated in 95% of MCL. Patients with truncated versions of the Cyclin D1 gene have poor prognosis (Chen et al. 2008). Constitutive expression of STAT3, a transcription factor, deregulates cell cycle progression, apoptosis, angiogenesis and tumor cell evasion of the immune system (Yu and Jove 2004; Yu et al. 2009). The activated B cell subgroup of DLBCL and MCL depends on overexpression of STAT3 for cell survival and proliferation (Ding et al. 2008; Lai et al. 2003).

Knockdown of such oncogenes in B cells by RNA interference (RNAi) may be a promising approach for treating B cell lymphomas. RNAi is a conserved endogenous mechanism in which small interfering RNAs (siRNAs) suppress target-specific gene expression by promoting mRNA degradation. There are many potential uses for siRNAs in a clinical setting, for example, in developing therapeutic agents. However, there are several challenges in using siRNAs in vivo, including poor stability, potential for off-target effects and ensuring specific delivery to the correct tissue or cells.

SUMMARY

The invention described herein relates to a B cell specific siRNA delivery system for silencing one or more predetermined target genes. In some embodiments, the system comprises a BAFF-R binding molecule that is associated with an siRNA molecule to form a BAFF-R binding molecule-siRNA complex, wherein the BAFF-R binding molecule-siRNA complex is internalized by a B cell and wherein the internalized siRNA inhibits the expression of one or more predetermined genes. In some embodiments, the BAFF-R binding molecule may be a BAFF Ligand construct. In other embodiments, the BAFF-R binding molecule may be an RNA molecule.

In one embodiment, a B cell specific aptamer-siRNA chimera is provided. The B cell specific aptamer-siRNA chimera may include an RNA aptamer that binds BAFF-R and an siRNA molecule conjugated to the RNA aptamer via a nucleotide linker. The nucleotide linker may include approximately 2-10 uracils. The RNA aptamer may be designed such that it accomplishes two therapeutic functions. First, the aptamer may competitively inhibit BAFF Ligand mediated cell proliferation, and second, the RNA aptamer, when fused to the siRNA chimera, is internalized by a B cell allowing the internalized siRNA to inhibit the expression of one or more predetermined genes.

In one aspect, the RNA aptamer is an RNA molecule having the sequence SEQ ID NO:37, SEQ ID NO:38 or SEQ ID NO:39. Upon binding BAFF-R, the aptamer may block BAFF ligand mediated cell proliferation.

In another aspect, the siRNA molecule suppresses expression of a target oncogene when internalized by a B cell. In some aspects, the target oncogene may be selected from Bcl6, Bcl2, STAT3, Cyclin D1, Cyclin E2 and c-myc. In one embodiment, the siRNA molecule may have a sense strand SEQ ID NO:7 and an antisense strand SEQ ID NO:8.

In other aspects, the siRNA molecule may be a bifunctional siRNA molecule which suppresses expression of at least two target oncogenes when internalized by the B cell. The two target oncogenes may be selected from Bcl6, Bcl2, STAT3, Cyclin D1, Cyclin E2 and c-myc. In these aspects, the chimera may have (i) a sense strand selected from SEQ ID NO:37, SEQ ID NO:38 or SEQ ID NO:39, and an antisense strand having the sequence SEQ ID NO:40; (ii) a sense strand selected from SEQ ID NO:41 or SEQ ID NO:42 and an antisense strand having the sequence SEQ ID NO:43; (iii) a sense strand having the sequence SEQ ID NO:46 and an antisense strand having the sequence SEQ ID NO:47; or (iv) a sense strand having the sequence SEQ ID NO:49 and an antisense strand having the sequence SEQ ID NO:48.

In another embodiment, a B cell specific RNA aptamer is provided. The RNA aptamer may be a molecule that binds to BAFF-R that has the sequence SEQ ID NO:37, SEQ ID NO:38 or SEQ ID NO:39. In some embodiments, the RNA aptamer is conjugated, via a nucleotide linker, to an siRNA molecule that suppresses expression of one or more target oncogenes in one or more B cells. In one aspect, the one or more target oncogenes are selected from Bcl6, Bcl2, STAT3, Cyclin D1, Cyclin E2 and c-myc. The siRNA molecule may have a sense strand SEQ ID NO:7 and an antisense strand SEQ ID NO:8.

In another embodiment, methods for treating a B cell malignancy in a cancer patient are provided. Such methods may include administering a therapeutically effective amount of a therapeutic composition, the therapeutic composition comprising a B cell specific RNA aptamer that binds BAFF-R. In one aspect, the B cell specific RNA aptamer is SEQ ID NO:37, SEQ ID NO:38 or SEQ ID NO:39.

In some embodiments, the therapeutic composition may additionally include an siRNA molecule that suppresses expression of one or more target oncogenes in one or more B cells. In this case, the siRNA is conjugated, via a nucleotide linker, to the RNA aptamer to form an aptamer-siRNA chimera. The one or more target oncogenes may be selected from Bcl6, Bcl2, STAT3, Cyclin D1, Cyclin E2 and c-myc. Further, the siRNA molecule comprises a sense strand SEQ ID NO:7 and an antisense strand SEQ ID NO:8. In some embodiments, the aptamer-siRNA chimera may have a sense strand having the sequence SEQ ID NO:46 or SEQ ID NO:49 and an antisense strand having the sequence SEQ ID NO:47 or SEQ ID NO:48, respectively.

BRIEF DESCRIPTION OF THE DRAWINGS

FIG. 14 is a table showing the alignment and identification of RNA aptamers (R1-R-22). Each RNA aptamer has a core region that has a first fixed sequence, GGGAGGAC-GAUGCGG (SEQ ID NO:12), attached to the 5' end of the core region and a second fixed sequence, CAGAC-GACUCGCCCGA (SEQ ID NO:13) attached to the 3' end of the core region. Following the 12$^{th}$ round of selection, the selected RNA pool was cloned and sequenced. After alignment of all 170 clones, eleven groups of anti-BAFF-R aptamers were identified. Only the random sequences of the aptamer core regions (5'-3') are indicated (SEQ ID NOs:14-35). Isolates occurring with multiple frequencies are specified. Sequenced aptamers were grouped by conserved nucleotide stretches underlined in the table, Group 1 had the highest frequency among all sequenced aptamers.

FIG. 16A shows gel mobility shift assays. The 5'-end P$^{32}$ labeled individual aptamers were incubated with the increasing amounts of BAFF-R protein. The binding reaction mixtures were analyzed by gel mobility shift assays.

FIG. 16B shows the calculated K$_d$ determinations for the gel mobility shift assays provided in FIG. 16A.

FIG. 36 is a table showing the results from two separate SELEX experiments targeting the BAFF-R-6×His-GST construct according to some embodiments. SELEX-1 was performed at room temperature (25° C.) and SELEX-2 was performed at physiological temperature (37° C.).

FIG. 41A illustrates an internalization and intracellular localization analyses. Jeko-1 cells were grown in 35 mm plates and incubated in culture medium with a 60 nM concentration of chimeras containing a 5'-Cy3-labeled sense strand for real-time live-cell confocal microscopy analysis as previously described. The chimeras showed cell-type specific binding affinity.

FIG. 41B illustrates an internalization and intracellular localization analyses. OEM control cells were grown in 35 mm plates and incubated in culture medium with a 60 nM concentration of chimeras containing a 5'-Cy3-labeled sense strand for real-time live-cell confocal microscopy analysis as previously described. The chimeras showed cell-type specific binding affinity.

FIG. 41C shows results from a localization study. After 5 hours incubation, cells were stained with Hoechst 33342 (nuclear dye for live cells) and then analyzed by confocal microscopy. The chimeras were localized in the cytoplasm of cells.

FIG. 57A shows the most common upregulated genes in Group 2 (BAFF ligand treatment) compared to Group 1 (control). The most common genes among all groups are in bold.

FIG. 57B shows the most common downregulated genes in Group 2 (BAFF ligand treatment) compared to Group 1 (control). The most common genes among all groups are in bold.

FIG. 58A shows the most common upregulated genes in Group 3 (R-1 aptamer treatment) compared to Group 1 (control). The most common genes among all groups are in bold.

FIG. 58B shows the most common downregulated genes in Group 3 (R-1 aptamer treatment) compared to Group 1 (control). The most common genes among all groups are in bold.

FIG. 59A shows the most common upregulated genes in Group 4 (BAFF ligand+R-1 aptamer treatment) compared to Group 1 (control). The most common genes among all groups are in bold.

FIG. 59B shows the most common downregulated genes in Group 4 (BAFF ligand+R-1 aptamer treatment) compared to Group 1 (control). The most common genes among all groups are in bold.

FIG. 60A shows the most common upregulated genes in Group 5 (R-22 aptamer treatment) compared to Group 1 (control). The most common genes among all groups are in bold.

FIG. 60B shows the most common downregulated genes in Group 5 (R-22 aptamer treatment) compared to Group 1 (control). The most common genes among all groups are in bold.

DETAILED DESCRIPTION

Figure 1:
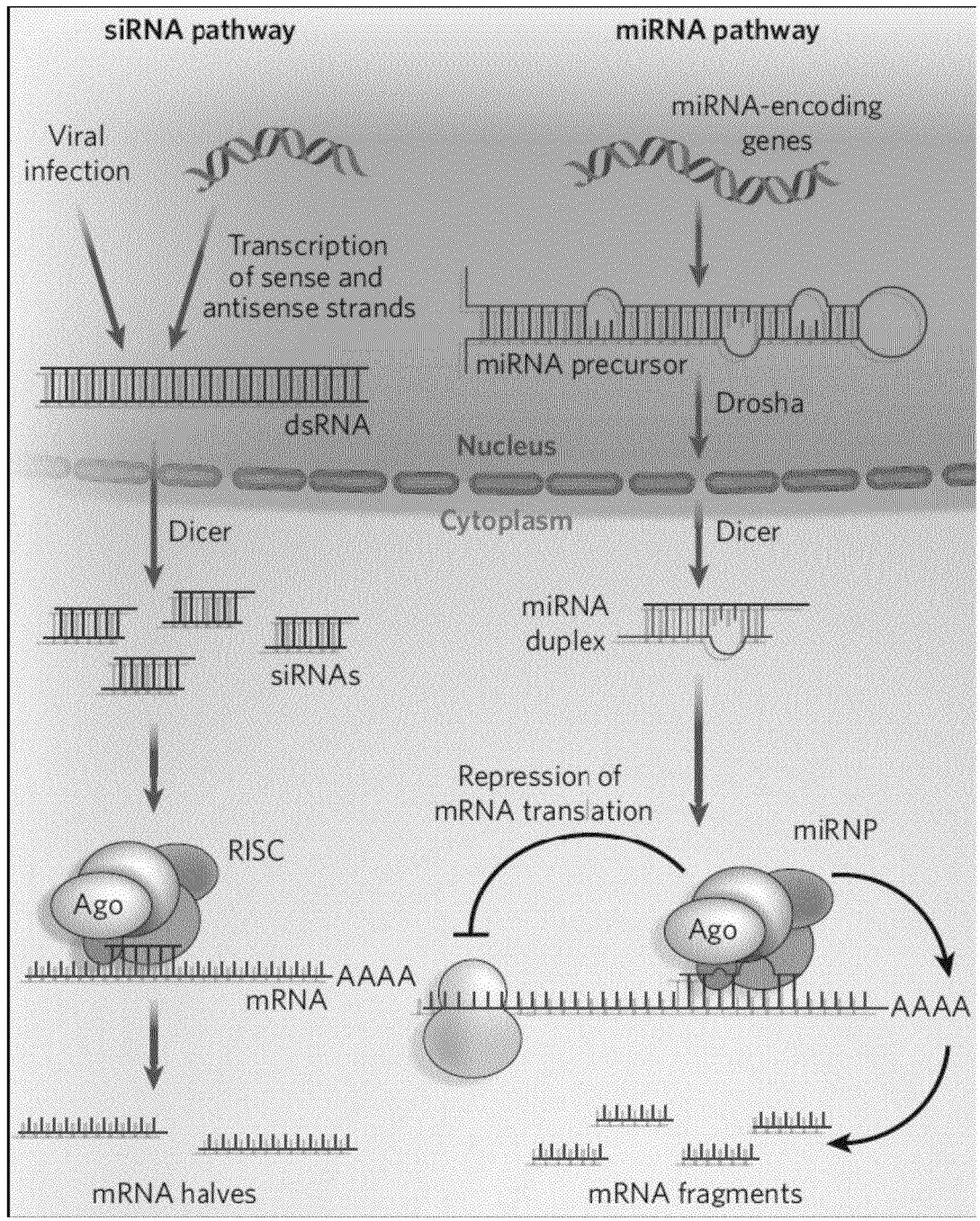
FIG. 1 is a schematic illustration of the siRNA—and the miRNA—pathway (adopted from Grosshans and Filipowicz, 2008).

B cell specific aptamers, systems for cell specific siRNA delivery and methods for their use are provided herein. According to the embodiments described herein, the B cell aptamers may be used alone or in combination with siRNA molecules for treatment of B cell malignancies.

B Cell-Specific Aptamers

In one embodiment, aptamers for targeting B cells are provided for the treatment of B cell malignancies or other B cell related diseases or conditions such as autoimmune diseases. An "aptamer" is any suitable small molecule, such as an nucleic acid or a peptide molecule that binds specifically to a target, such as a small molecule, protein, nucleic acid, cell, tissue or organism. Aptamers that target specific cell surface proteins can be employed as delivery molecules to target a distinct cell type, thereby reducing off-target effects or other unwanted side effects. Further, by binding a specific cell surface protein, the aptamers may also be used as a therapeutic agent on their own.

According to the embodiments described herein, aptamers for targeting B cells may bind a target molecule on the surface of B cells. In some embodiments, the target molecule is the B cell activating factor receptor (BAFF-R), which is normally modulated by its ligand, BAFF (or "BAFF ligand").

Proper expression of a functional antigen receptor is a prerequisite for the production and subsequent survival of a pool of mature peripheral B lymphocytes. Mature lymphocytes also require antigen receptor independent signals to survive, which in case of B-cells is mediated by BAFF (also known as BLyS, TALL-1 and TNFSF13B) (Schiemann et al. 2001). The mechanism that is involved in the intracellular events that link BAFF to its biological effects is poorly characterized (Bossen and Schneider 2006), however it is believed that one action of BAFF is to activate the NFκB pathway resulting in the processing of the p100 NF-κB2 protein to its active p52 component in primary B cells (Kayagaki et al. 2002).

BAFF is part of the tumor necrosis factor (TNF) family of cytokines and has been shown to enhance the maturation and survival of peripheral B-cells (Thompson et al. 2001; Moore et al. 1999; Gross et al. 2000). Within its human gene, exon 1 codes for the transmembrane domain and its flanking regions, exon 2 for a furin processing site, and exons 3-6 for the TNF homology domain, which is responsible for receptor binding.

BAFF is a Type II membrane-bound protein, but can also be released as a soluble homo-trimer upon proteolytic cleavage at the furin consensus site. BAFF binds to three receptors, named BCMA (B cell maturation antigen), TACI (transmembrane activator and calcium modulator and cyclophilin ligand interactor) and BAFF-R (BAFF receptor), on mature B cells in the peripheral immune system and promotes the activation and survival of B cells, both in vitro and in vivo. BAFF is produced by dendritic cells, monocytes and macrophages (Craxton et al. 2003) and binds the BAFF-R (Thompson et al. 2001) as well as TACI (von Bulow and Bram 1997) with affinities in the nanomolar range, but also shows two to three order of magnitude weaker binding to BCMA (Laabi et al. 1992). All three receptors, BCMA, TACI, and BAFF-R, display structural conservation in a β-hairpin structure that fits in a binding pocket of BAFF. The following helix-loop-helix motif is different among the receptors, with BAFF-R containing only the first helix. While BCMA and TACI also interact with other ligands, BAFF-R is exclusive to BAFF. BAFF trimerizes and binds to the BAFF-R on the cell surface where it is internalized by receptor-mediated endocytosis (Nimmanapalli et al. 2006; Lyu et al. 2007). the interaction of BAFF and BAFF-R has been identified as significant in B-cell survival, proliferation and maintenance (Shulga-Morskaya et I. 2004; Thompson et al. 2000; Batten et al. 2000).

BAFF-R distribution and biological activity is restricted to mature B-Lymphocytes and various tumor B-cell lines (Moore et al. 1999; Nardelli et al. 2001). Diffuse Large B-cell Lymphoma, Mantle Cell lymphoma and marginal zone-B-cell Lymphoma cells derived from patients express BAFF-R, while tumor cells from patients with T-cell NHL did not express any BAFF-R (Briones et al. 2002). BAFF ligand trimerizes and binds to the BAFF-R on the cell surface where it is internalized by receptor mediated endocytosis (Nimmanapalli et al. 2006; Lyu et al. 2007). Upon BAFF binding, this pathway can enhance cell proliferation. BAFF-R, restrictedly expressed on B-cell lines, represents an attractive target for intervention in autoimmune diseases.

Excessive BAFF production has been shown to trigger severe autoimmune disorders in mice resembling systemic lupus erythematosus (SLE) and Sjögren's syndrome (SS) (Ju et al. 2007). In addition, numerous B-cell malignancies show increased or overexpression of BAFF-R (He et al. 2004; Novak et al. 2004; Kern et al. 2004; Tecchio et al. 2007), which is expressed only in B cells, and is not present in other normal cells, including T lymphocytes. Non-Hodgkin's Lymphoma cell lines such as Jeko-1, Rec-1, JVM-2, SUDHL4, Raji and Z138 express BAFF-R to different degrees. Additionally, BAFF trimerizes and binds to the BAFF-R on the cell surface where it is internalized by receptor mediated endocytosis. This allows targeting of the BAFF-R for delivery purposes. The BAFF/BAFF-R pathway also enhances cell proliferation. BAFF-R, as the predominant BAFF receptor restrictedly expressed on B cell lines, represents an attractive target for intervention in B cell lymphomas and autoimmune diseases. This interaction also increases the survival and proliferation of malignant cells, enabling cancer cells to proliferate faster than normal B-cells. Because BAFF-R is the sole receptor that mediates the B cell survival signal from BAFF (Yan et al. 2001), agents that modulate this ligand/receptor system could be useful treatments for various B cell malignancies.

Furthermore NHL B-cell lines derived from patients contain more BAFF than normal B cells (He et al. 2004). Further studies suggest that BAFF promotes in vitro and in vivo B-cell survival by up-regulating anti-apoptotic proteins such as Bcl-2 and Bcl-xL (Do et al. 2000; Khare et al. 2000; Shulga-Morskaya et al. 2004). The BAFF-R is the most abundantly expressed in approximately 80% of mantle cell Lymphomas and 40% of Diffuse Large B-cell Lymphomas (Nakamura et al. 2005).

Therefore, in some embodiments, a B cell specific aptamer that targets and binds BAFF-R is provided. In one embodiment, the BAFF-R aptamer is a nucleic acid molecule. For example, the nucleic acid BAFF-R aptamer may be an RNA aptamer molecule. In some embodiments, the RNA aptamer may be any one of the aptamers illustrated in FIG. 14. In other embodiments, the RNA aptamer may have the sequence SEQ ID NO:9 (R-1), SEQ ID NO:10 (R-14) or SEQ ID NO:11 (R-22).

Nucleic acid aptamers with binding affinities in nanomolar range have been utilized for flexible applications ranging from diagnostic to therapeutic assay formats (Zhou & Rossi 2009). Moreover, aptamers that target specific cell surface proteins are employed as delivery molecules to target a distinct cell type, hence reducing off-target effects or other unwanted side effects (Zhou et al. 2008; McNamara et al. 2006).

Selection of aptamers may be accomplished by an optimized protocol for in vitro selection, known as SELEX (Systemic Evolution of Ligands by EXponential enrichment). Although the SELEX process has been established as a general technique for aptamer selection, it is not predictable nor is it standardized for use with any target. Instead, the SELEX process must be optimized and customized for each particular target molecule. Each SELEX experiment includes its own challenges and is not guaranteed to work for all targets.

Many factors are important for successful aptamer selection. For example, the target molecule should be stable and easily reproduced for each round of SELEX, because the SELEX process involves multiple rounds of binding, selection, and amplification to enrich the nucleic acid molecules. In addition, the nucleic acids that exhibit specific binding to the target molecule have to be present in the initial library. Thus, it is advantageous to produce a highly diverse nucleic acid pool. Because the starting library is not guaranteed to contain aptamers to the target molecule, the SELEX process for a single target may need to be repeated with different starting libraries. Aptamer selection using SELEX is unpredictable. Even when all of the factors are optimized for successful aptamer selection, the SELEX process does not always yield viable aptamers for every target molecule.

To demonstrate the unpredictable nature of the SELEX process, the process that led to the generation of the aptamers described herein is illustrated in Example 3 below. This process ultimately led to the isolation of several new 2'-Fluoro substituted RNA aptamers against human BAFF-R from an 81-nt RNA library by using a nitrocellulose-filter based SELEX process (Systematic Evolution of Ligands by EXponential enrichment).

In some embodiments, the aptamers described herein may be 2'-fluro modified RNA aptamers that bind specifically to BAFF-R and that are generated from an 81 nt RNA library via in vitro SELEX. As further discussed in the Examples below, these aptamers showed specific binding to and internalization by BAFF-R expressing B-Lymphoma cells but not by BAFF-R negative T-cells (OEM).

In some embodiments, the aptamers described herein may be used alone as part of a therapeutic composition for treating a B cell malignancy. BAFF stimulates survival of B-cells upon binding to BAFF-R (Thompson et al. 2000; Batten et al. 2000) and also enhances NHL B cell proliferation especially in combination with APRIL (He et al. 2004). Furthermore, peripheral blood mature B-cells from mice over-expressing BAFF have an increase of Bcl-2 protein expression (Mackay et al. 1999), which at least in part accounts for their enhanced survival. As discussed in the examples below, gel shift assays showed that the aptamers described herein can specifically bind to the human BAFF-R protein with nanomolar affinities (for example: R1 $K_d$=47.12 nM; R2 $K_d$=95.34 nM; R14 $K_d$=95.65 nM). Furthermore, flow cytometry and real-time confocal microscopy analysis revealed that these aptamers are able to selectively bind and be internalized into the Jeko-1 cells, a type of B-cell lines expressing BAFF-R protein. Unlike the endogenous BAFF ligand, the aptamers R-1 and R-14 and the aptamer chimeras derived from R-1 (described below) do not enhance cell proliferation, nor do they upregulate Bcl2 expression, and the R1 aptamer is able to block BAFF ligand mediated proliferation of these cells in MTS assays.

Further, the aptamers blocked ligand-mediated proliferation in NHL cell lines due to competing for the receptor with BAFF ligand, indicating that the aptamers are effective for inhibiting or suppressing ligand-mediated proliferation in B cell malignancies and may therefore be used as a therapeutic for B cell malignancies or autoimmune disease.

In another embodiment, the BAFF-R aptamers described herein may also be used as a cell specific delivery vehicle to deliver a therapeutic payload to B cells. For example, the BAFF-R aptamer may be conjugated to an siRNA molecule as described in detail below. According to the embodiments described herein, BAFF-R aptamers were generated with nanomolar binding affinity, that can act as a cell-specific delivery vehicle as well as a therapeutic agent that can inhibit or suppress proliferation of B cells or B lymphoma cells, without enhancing their survival. As described in the examples below, the BAFF-R aptamers can deliver siRNAs efficiently to NHL cell lines without increasing cell proliferation or survival of cancerous cells. In a therapeutic setting, multiple aptamers and siRNAs might be needed to inhibit or kill cancer cells completely as in most cancers more than one gene is deregulated. Therefore, the BAFF-R aptamers illustrate dual functions: inhibition of proliferation and survival mediated by BAFF and an siRNA delivery vehicle.

siRNA and B Cell-Specific siRNA Delivery Systems

Cell specific siRNA delivery may be used to suppress the expression of target genes that are associated with conditions or diseases that are particular to a certain cell population, tissue or organ, by exploiting the RNA interference (RNAi) system.

RNA interference (RNAi) is a process of target sequence-specific gene knock-down resulting in blocking the expression of a targeted gene. RNAi is triggered by double-stranded RNA (dsRNA) which can be produced endogenously (by miRNA-encoding genes) or introduced by administering specific sequences. Long dsRNA is processed by the enzyme Dicer (after processing by Drosha in case of miRNA precursors) to form short interfering RNA (siRNA) or micro RNA (miRNA). One strand of the siRNA or miRNA (the "guide RNA strand") subsequently guides the assembly of a multi-protein complex known as the RNA induced silencing complex (RISC) or the miRNA-ribonucleoprotein (miRNP), with its core component Argonaute 2. Depending on the extent of homology of the guide RNA strand to the target sequence, the target mRNA can either be degraded or its translation can be suppressed, resulting in gene silencing (Barik 2008) (FIG. 1).

The RNAi pathway described above is present in virtually every experimental eukaryotic system, and siRNA may be used to target any gene in the genome. Thus, in some embodiments, the cell-specific siRNA delivery system described herein may be used to validate B cell disease models in cell-based systems (in vitro) or in an animal model (in vivo). In other embodiments, the cell-specific siRNA delivery system may be used to validate the mechanism of action for drugs through the removal of suspected targets as well as identify new drug candidates in genome-wide, functional genomics screens. In further embodiments, the cell-specific siRNA delivery system may exploit the RNAi pathway directly to treat diseases associated with B cells using RNAi based therapeutics in the clinic (Paddison and Vogt 2008).

There are at least three main components of the RNAi pathway for dsRNA based gene silencing: Drosha, Dicer, and Argonaute (Ago) gene family members. The RNase III family members Drosha and Dicer are responsible for the first catalytic steps that convert various forms of dsRNA into shorter guide dsRNA of 21-25 nucleotides (nt) in length. The cleaved dsRNAs have characteristic ends consisting of a 5' phosphate group and a two nucleotide overhang at the 3' end. All Drosha- and Dicer-related genes have a single dsRNA-binding domain and two tandem RNAse III domains. Dicers also have two other conserved sequence motifs: the DExH/DEAH ATPase/RNA helicase domain and a PAZ domain which can be found only in RNAi related genes. The core component of RISC is Ago2 which contains a PAZ domain and a carboxyl-terminal PIWI domain with a high degree of similarity to the catalytic core of RNase H enzymes.

Dicer is responsible for cleavage of dsRNA into pieces ranging from 21 to 27 nt. Dicer is capable of binding the end of the dsRNA and subsequently cuts a pre-determined length from the end, which in higher eukaryotes is approximately 22 nt, the average size of a siRNA. Analysis of the crystal structure of a Dicer from the parasite *Giardia* revealed that Dicer itself is the molecular ruler that recognizes dsRNA ends and cuts at a pre-determined distance from the end. The mature siRNA is then unwound and only one strand is incorporated into the RISC to guide it and seek target RNA. The selection of which strand will be the guide RNA strand may relate to certain features of the sequence of siRNA, such as the internal energy of the siRNA molecule (Schwarz et al. 2003). The internal stability of the 5' end of the antisense strand is also important to this selection, because its stability has been found to be lower than other portions of the molecule in effective siRNAs.

The core of the RISC is Argonaute 2 (Ago2). Analysis of the crystal structure of Ago2 revealed that the PAZ domain enables binding of the 3' end through a nucleic acid-binding fold (Song et al. 2003). For this interaction, the presence of a 3' single stranded RNA overhang appears to be critical. The localization of the RISC complex is guided by the antisense single-stranded siRNA component and is mediated through sequence alignment of the two RNA molecules. The PIWI domain is responsible for the slicing activity that Ago family members possess. However, slicer activity is determined by the extent of complementarity between the guide RNA and the target mRNA. In case of a perfect match the target RNA is cleaved at a position ~10 nt from the first nucleotide that represented the first based pair from the 5' end of the original siRNA (Gaudy et al. 2003). An imperfect match (as has been found for most miRNAs in higher eukaryotes) can have several effects: inhibition of translational initiation or elongation, de-adenylation, transport to the cytoplasmic "P-body" for nuclease degradation, or a combination of these three results.

Several types of short RNA structures (also referred to as "RNAi triggers") that are modeled after natural structures in the RNAi pathway may be used to elicit sequence-specific gene silencing. For example, siRNAs that mimic the Dicer cleavage products may be used. In other embodiments, 27mer dsRNA Dicer substrates (Kim et al. 2005) or short-hairpin RNAs (shRNAs) that resemble miRNAs may be used. Successful sequence-specific silencing in mammalian cell lines was first achieved using siRNAs containing 21 nucleotides (nt) of identity to a homologous mRNA target (19 nt of dsRNA and a 2-nt 3' overhang) (Elbashir et al. 2001). siRNAs are believed to bypass processing by Dicer and are incorporated directly into the RISC. As an alternative strategy, in vivo expression cassettes have been developed that resemble endogenously expressed hairpin RNAs that yield Dicer substrates, which are incorporated into the RISC after being processed by Dicer. These have been named short hairpin RNAs (shRNAs) and can be categorized according to the RNA polymerase that is used to drive their expression. Hairpins containing 19-29 basepairs (bp) of dsRNA in addition to the loop structure can be driven from RNA polymerase III promoters (for example the human or mouse U6-snRNA or human RNase P (H1) RNA promoters) and yield short transcripts of defined length containing 2-nt 3' overhangs. The latter feature was identified as being critical for nuclear export and induction of the RNAi pathway through interactions with exportin-5 and Dicer's PAZ domain. Alternatively, RNA polymerase II promoters can be used, yielding shRNAs that resemble endogenous miRNA, which are also expressed from RNA POL II promoters. These shRNA are first processed by Drosha rather than Dicer. Using miRNA-based shRNAs can be advantageous, since they can be expressed from any number of well characterized POL II expression systems (e.g., tissue specific promoters or tet-inducible systems). In addition, the exact 22-nt sequence to be incorporated into RISC via Drosha and Dicer processing is known, which makes the use of algorithms to predict effective target sequences possible.

In some embodiments, a B cell-specific siRNA delivery system is provided. The B cell specific siRNA delivery system includes a B cell targeting moiety that is associated with one or more siRNA molecules that target and inhibit or suppress the expression of one or more oncogenes expressed in B cells. For example, B cell lymphomas overexpress several oncogenes such as transcription factors Bcl6, STAT3 and c-myc, anti-apoptosis protein Bcl2, syk and Cyclin family members such as Cyclin D1, Cyclin D2 and Cyclin E2. Therefore, according to some embodiments, an siRNA molecule that is part of the B cell specific siRNA delivery system may target and inhibit or express one or more oncogenes in B cells including, but not limited to, Bcl6, STAT3, c-myc, Bcl2, Cyclin D1, Cyclin D2, Cyclin E2 and syk.

The siRNA molecule that is associated with the B cell targeting moiety in the B cell-specific siRNA delivery system may include any suitable short RNA structure including, but not limited to, siRNAs, shRNAs, miRNAs and other short dsRNAs. In one embodiment, the siRNA molecule may be a traditional monofunctional siRNA molecule having a functional antisense strand and a complementary sense strand. According to some embodiments, the traditional siRNA molecule may be designed to target Bcl6, STAT3, c-myc, Bcl2, Cyclin D1, Cyclin D2, Cyclin E2 or syk. In some embodiments, the monofunctional siRNA molecule may target Cyclin D1 (Design 1: SEQ ID NO:1 (sense), SEQ ID NO:2 (antisense); Design D2: SEQ ID NO:3 (sense), SEQ ID NO:4 (antisense)) or STAT3 (SEQ ID NO:7 (sense), SEQ ID NO:8 (antisense)).

In another embodiment, the siRNA molecule may be a bifunctional siRNA molecule. A bifunctional siRNA molecule can contain two fully target-complimentary and functional antisense strands against two targets at the same time, but are only partially complementary to each other. The bifunctional design allows inhibiting of two genes simultaneously and therefore, these siRNAs ma decrease off-target effects compared to conventional siRNAs due to the lack of undesired activity of the sense strand. Moreover, because it is desired to target more than one oncogene in NHL or other cancer therapy, the simultaneous delivery of two effective antisense strands indicates the reduction of effective concentration of the siRNA drug, resulting in less toxicity and lower production costs. In addition to the conventional siRNAs of 21 mer duplexes, bifunctional siRNAs were designed as Dicer-substrates. These duplexes include the same sequence as the 21 mer but within a longer 27mer duplex that serves as a Dicer-substrate. A bifunctional siRNA molecule can be synthesized either with 2 nucleotide overhangs, with blunt ends or with one blunt end and two deoxynucleotides at the 3' end of the sense strand and a 3' overhang at the antisense strand. Dicer substrates show improved efficacy at lower concentrations as compared to conventional 21 mer siRNAs (Kim et al. 2005). According to some embodiments, the bifunctional siRNA molecule may be designed to target two genes selected from Bcl6, STAT3, c-myc, Bcl2, Cyclin D1, Cyclin D2, Cyclin E2 and syk. For example (as shown below), the bifunctional siRNA molecule may target 1) Bcl2 and STAT3, 2) c-myc and Bcl2, 3) Cyclin E2 and Cyclin D1 or 4) any other combination of oncogenes expressed by B cells.

Figure 2:
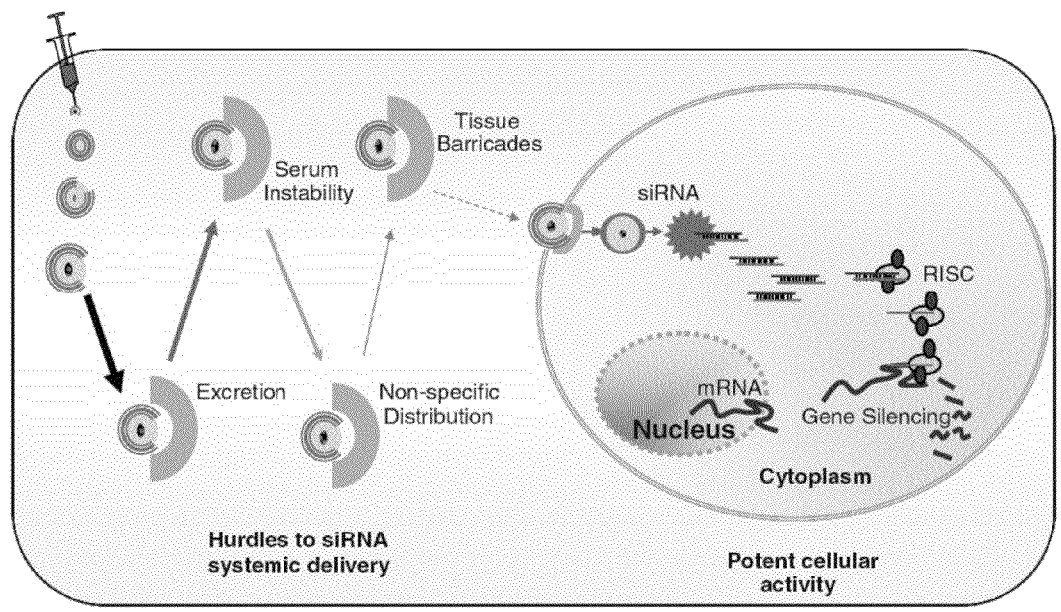
FIG. 2 is a schematic illustration of the challenges of systemic in vivo delivery of siRNA (adopted from Lu et al. 2008).

There are several challenges to the in vivo application of RNAi-based therapeutics (FIG. 2). In particular, the success of in vivo application of RNAi-based therapeutics is largely hindered by, among other things, 1) the lack of a delivery system that can transport the siRNA or other RNAi trigger specifically into the target tissue and subsequently into the cell cytoplasm, and 2) the effect of "off-target" silencing.

Off-target effects can occur when the amount of mismatches between the guide RNA and target sequences is low and consequently tolerated such that both cognate and non-cognate mRNA targets are silenced. This undesirable effect arises as a direct result of guide RNA/Ago binding properties, which are determined by only the first 2-8 nucleotides at the 5' end of the guide RNA strand (Jackson et al. 2003, Birmingham et al. 2006). While this so-called "seed" sequence allows miRNAs to target several mRNAs through partial sequence complementarity, it leads to off-target effects when siRNAs or shRNAs are used. As a consequence each RNAi trigger should be designed in a way as to minimize possible unintended interactions. One way to minimize the unintended interactions would be to confirm that the resulting phenotype is the same for multiple RNAi trigger targeting the same gene. Another way is to use bifunctional RNAi triggers, as described below.

A number of approaches for delivering siRNA to a specific target cell's cytoplasm may be used, ranging in complexity from simple naked siRNAs to complicated nanoparticle-based delivery vehicles. Examples include, but are not limited to, 1) DNA templates encoding siRNA sequences may be delivered to cells that can be transcribed to express siRNAs (Amarzguioui et al. 2005) (but relies on plasmid or viral vectors for the delivery and requires transfection, stable vector integration, and selection for maintenance of expression through generations (Brummelkamp et al. 2002); 2) the use of cationic liposomes, cholesterol conjugates, antibody conjugates, electroporation, direct injection, hydrodynamic transfection, electrical pulsing or any other suitable method of direct delivery (De Fougerolles 2008); 3) cationic lipids, such as Lipofectamine, as a transfection reagent may be used to deliver siRNA in vitro (but is limited to specific cell types, and its application could be toxic to cells and animals (Ohki et al. 2001)); 4) siRNA may be delivered systemically using cholesterol conjugates, liposomes, and polymer-based nanoparticle sized delivery vehicles (but has shown little success thus far); and 5) siRNA may be delivered via peptide-mediated delivery systems.

According to some embodiments, a positively charged peptide or protein may be used to produce a protein-siRNA complex that can be used to deliver siRNAs. The phosphate backbone of siRNAs is negatively charged and allows complex formation with cationic peptides and proteins regardless of its sequence. In some embodiments, the protein-siRNA complex can include a non-specific cell-penetrating peptide (e.g. Tat) to deliver the siRNA to cells. Previous studies have coupled siRNAs with nanoparticles and cell-penetrating peptides, but such couplings were not specific for a certain type of cell. Other studies have linked PEGylated siRNA to a peptide ligand specific to the VEGF receptor-2 or to a cell-surface specific antibody for tissue specific delivery. In other embodiments, the protein-siRNA complex can include a targeting moiety, such as a receptor-binding peptide or antibody for specific delivery. Previous studies have used a 2' ribopurine, 2' fluoropyrimidine chimera that contains a prostate-specific membrane antigen (PSMA) aptamer and a siRNA (McNamara et al 2006, Chu et al. 2006). This construct was internalized into the PSMA-expressing prostate cancer cells and induced the RNAi pathway.

Systemic delivery of siRNAs to specific cells via cell-surface receptors should provide a maximal therapeutic benefit, decrease the therapeutically effective amount of drug needed, and avoid non-specific silencing or toxicity in healthy cells (Simeoni et al. 2005). This complexation-based delivery strategy using a receptor specific ligand has been successfully applied in vivo.

For example, Kumar et al. showed delivery of siRNA achieved by using a synthetic chimeric peptide consisting of a 29-amino acid rabies virus glycoprotein (RVG) peptide that was extended by a nonamer of arginine residues (9R) at the carboxy terminus (Kumar et al. 2007). RVG specifically binds to the acetylcholine receptor expressed on neuronal cells and RVG-9R was capable of delivering siRNAs to neuronal cells. This was demonstrated by incubating the siRNAs with the positively charged RVG-9R peptide and subsequent intravenous administration, resulting in specific gene silencing. In addition, it was shown that treatment of mice with siRNA against the Japanese encephalitis virus complexed with RVG-9R resulted in strong protection from lethal infection (Kumar et al. 2007).

In addition, Nimmanapalli et al. and Lyu et al. showed that a fusion construct of BAFF and recombinant Gelonin (rGel), a type 1 ribosome-inactivating toxin, induces apoptosis specifically in BAFF-R positive cells (Nimmanapalli et al. 2007, Lyu et al. 2007). The construct was shown to selectively bind and internalize through BAFF-R into B-CLL (B-cell chronic lymphocytic leukemia) lymphocytes and induced apoptosis in nanomolar concentrations.

Further, Zhang et al. showed that liposomes with mBAFF (a mutant BAFF protein) and PEG on the surface could deliver vincristine, a common drug used in chemotherapy regimens, in Raji cells. The mutant BAFF protein was capable of binding the receptor, but did not induce proliferation (Zhang et al. 2008).

Thus, in some embodiments, the B cell-specific siRNA delivery system includes a B cell targeting moiety that binds a B cell-specific receptor, for example, the B cell activating factor receptor (BAFF-R).

Thus, in some embodiments, B cell specific siRNA delivery may be mediated by the BAFF-R. This may be accomplished by the use of any suitable and efficient BAFF-R binding molecule that may be associated with or conjugated to one or more of the siRNA molecules described herein. In one embodiment, the BAFF-R mediated siRNA delivery may be accomplished by a BAFF construct that is associated with an siRNA complex. In one embodiment, the BAFF construct may be a fusion protein having a 9-arginine extension "tag" (BAFF-9R), which allows the BAFF construct to bind negatively charged siRNA. The BAFF-R construct is not limited to having a 9-arginine extension tag, but may have any tag that is able to bind negatively charged siRNA (e.g., protamine or other peptides). In another embodiment, the BAFF-R construct may include a 9-arginine or other suitable tag that is added to purified BAFF via chemical reaction.

Figure 3A:
FIG. 3A illustrates the construction of the MBP-His-BAFF-9R construct according to some embodiments. The schematic shows the MBP-His-BAFF-9R construct that contains both an MBP and a 6×His tag at the N-terminus. In addition, a Factor Xa cleavage site between the MBP and the 6×His tag and a recognition site for the tobacco etch virus (TEV) protease make enzymatic cleavage of the tags possible.

The BAFF construct may be produced by any suitable cloning and purification method. For example, the protein of interest, BAFF-9R, may be expressed as a fusion construct tagged with the maltose-binding protein (MBP) using the pMAL system. The MBP tag is large, but is expressed well by E. coli and capable of making the protein of interest more soluble. The pMAL system may be used to fuse the BAFF-9R construct to the C-terminus of MBP. The pMAL-C2x vector introduces a Factor Xa recognition site, so the MBP tag can be subsequently removed. In addition, a 6×His-tag may be added at the N-terminus of BAFF-9R by PCR. The 6×His-tag was separated by recognition site for the tobacco etch virus (TEV) protease, allowing for removal of the tag after successful expression and purification. FIG. 3A shows the scheme of the full fusion MBP-His-BAFF-9R construct that may be expressed using the pMAL system. Other cloning and purification methods that may be used to generate a BAFF-9R aptamer are described in Hergenreider, E., B Cell specific delivery system for siRNA, (May 2008) (unpublished M. S. Thesis, Friedrich-Alexander-Universitat Erlangen-Nümberg), which is incorporated by reference in its entirety, as if fully set forth herein.

In other embodiments, the B cell targeting moiety is a BAFF-R aptamer, such as the BAFF-R aptamers described above. Such a BAFF-R aptamer may be conjugated to an siRNA molecule described herein to form an aptamer-siRNA chimera.

The aptamer-siRNA chimera may be synthesized or constructed using any suitable conjugation method. In one embodiment, the aptamer-siRNA chimera is constructed by a method of covalent conjugation. Synthesis of conjugates, for example, the aptamer-siRNA chimera described herein, via a covalent construction strategy involves chemically linking an siRNA molecule to an aptamer that involves the sharing of pairs of electrons. In one embodiment, a BAFF aptamer may be fused to an siRNA molecule via a nucleotide linker to form a BAFF-R aptamer-siRNA chimera. In one embodiment, the nucleotide linker may be one or more uracil (U). The nucleotide linker may vary in length. For example, the nucleotide linker may be between approximately 2 to 10 uracils alone or in combination with other nucleotides. In some embodiments, the nucleotide linker may be 2, 3, 4, 5, 6, 7, 8, 9, or 10 uracils alone or in combination with other nucleotides in length. In other embodiments, the nucleotide linker may be more than 10 nucleotides in length. In one embodiment, the nucleotide linker is a 2-nucleotide linker (UU). In another embodiment, the nucleotide linker is am 8-nucleotide linker (UUUUUUUU).

In another embodiment, the aptamer-siRNA chimera is constructed by a method of non-covalent conjugation. Non covalent conjugation involves chemically linking two molecules without sharing of pairs of electrons. Non-covalent conjugation may involve electromagnetic or electrostatic interactions such as hydrogen bonds, ionic bonds, van der Waals forces and hydrophobic interactions.

In some embodiments, the aptamer-siRNA chimera is a BAFF-R aptamer-siRNA chimera that can be used for targeted delivery of a 27-mer Dicer substrate siRNA against the Cyclin D1 (CCND1) gene. Such a BAFF-R aptamer-siRNA chimera may have a sense strand with the sequence SEQ ID NO:37, SEQ ID NO:38 or SEQ ID NO:39 and an antisense strand having the sequence SEQ ID NO:40; or a sense strand having the sequence SEQ ID NO:41, SEQ ID NO:42 or SEQ ID NO:43 and an antisense strand having the sequence SEQ ID NO:43.

In other embodiments, the aptamer-siRNA chimera is a BAFF-R aptamer-siRNA chimera that can be used for targeted delivery of a 27-mer Dicer substrate siRNA against the STAT3 gene. Such a BAFF-R aptamer-siRNA chimera may have a sense strand with the sequence SEQ ID NO:46 and an antisense strand having the sequence SEQ ID NO:47 (R-1-STAT3 27-mer OVH Chimera); or a sense strand with the sequence SEQ ID NO:49 and an antisense strand having the sequence SEQ ID NO:48 (R-1-STAT3 27-mer SWAP Chimera).

As discussed in the examples below, these created chimeras retain the high binding affinity of the RNA BAFF-R aptamer alone and can be selectively internalized into Jeko-1 cells but do not bind to the control T-lymphocyte CEM cells that do not express BAFF-R. Further, an aggregation of aptamer or aptamer-siRNA chimeras in the cytoplasm by confocal microscopy was observed, indicating that aptamers are internalized by receptor-mediated endocytosis. Although how they escape the endosomes is unclear, the specific down-regulation of target genes mediated by the aptamer siRNA chimeras suggests that siRNA can be released from endosome and entry RNAi pathway. Two BAFF-R aptamer-STAT3 siRNA chimeras were designed, which are described in detail below. Both chimeras were successfully processed by Dicer and triggered specific mRNA cleavage. They showed similar levels of target mRNA and protein reduction.

It was previously demonstrated that a PSMA-RNA-aptamer conjugated to the toxin gelonin showed enhanced efficacy in treatment of prostate cancer and decreased toxicity on cells not expressing PSMA (Chu et al. 2006). Furthermore, chimeric proteins composed of chemokine ligands such as interleukin-2, -3 or VEGF fused to various toxins (e.g. gelonin, diphteria) demonstrated significant and selective cytotoxic effects against target cells with nanomolar affinity. Recently gelonin was also fused to BAFF (rGel/BLys)[5] and indicated the highest cytotoxicity on MCL cell lines (Lyu et al. 2007). Biodistribution of rGel/BLys in SCID mice showed localization in tumor and reduction of tumor growth (Wen et al. 2010). Nevertheless, the heterogenous intratumoral distribution made the eradication of the solid tumor by treatment with rGel/BLys alone impossible (Wen et al. 2010). These studies taken together indicate that a combination of two or more separate therapeutics such as an antibody/aptamer combined with a toxin/siRNA might have a bigger and better effect than their parts. Hence our aptamer-siRNA chimeras are a step into the right direction in combining effective therapeutics against NHL together to result in a more effective therapeutic.

Thus, the aptamer-siRNA chimeras described herein may be further conjugated to one or more additional therapeutic agents which may include, but are not limited to, chemotherapeutics, targeted therapies, immunotherapeutics, and radiotherapeutics. Examples of such therapeutic agents include, but are not limited to, drugs, chemotherapeutic agents, therapeutic antibodies and antibody fragments, toxins, radioisotopes, enzymes (e.g., enzymes to cleave prodrugs to a cytotoxic agent at the site of the tumor), nucleases, hormones, immunomodulators, antisense oligonucleotides, chelators, boron compounds, photoactive agents and dyes.

In summary, the BAFF-R apatmers described herein act not only as specific delivery vehicles for therapeutic payloads such as siRNA, but may also be used on their own as part of a therapeutic for NHL by blocking ligand mediated proliferation and survival signals.

Treatment of B Cell Malignancies

The aptamers and the aptamer-siRNA chimeras described herein have a dual function that provides a basis for treating B cell malignancies. As described in the Examples below, the aptamers may serve as a B-cell specific targeting delivery vehicle to deliver a payload to a particular cell. In one embodiment, the payload may be an siRNA molecule that is part of the aptamer-siRNA chimeras described herein. In addition, the aptamers may be used on their own to inhibit or suppress proliferation and survival of B cells, and may also be used to eradicate existing primary or metastatic tumors (see Example 6 below).

Therefore, methods for suppressing B cell proliferation, eradicating B cell tumors and treating a B cell malignancy, are provided according to the embodiments described herein. B cell malignancies that may be treated using the methods described herein include, but are not limited to, Non-Hodgkin's Lymphomas (NHL), Diffuse Large B Cell Lymphoma (DLBCL), Small lymphocytic lymphoma (SLL/CLL), Mantle cell lymphoma (MCL), Follicular lymphoma (FL), Marginal zone lymphoma (MZL), Extranodal (MALT lymphoma), Nodal (Monocytoid B-cell lymphoma), Splenic, Diffuse large cell lymphoma, Burkitt's lymphoma and Lymphoblastic lymphoma.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The methods for treating the B cell malignancy includes administering a therapeutically effective amount of a therapeutic composition. An "effective amount," "therapeutically effective amount" or "effective dose" is an amount of a composition (e.g., a therapeutic composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The therapeutic composition may include, among other things, an aptamer, an siRNA molecules, and the aptamer-siRNA chimeras described above and in the examples below. For example, in some embodiments, an RNA aptamer that may be part of the therapeutic composition may be any one or more of the aptamers illustrated in FIG. 14. In other embodiments, such an RNA aptamer may have the sequence SEQ ID NO:9 (R–1), SEQ ID NO:10 (R-14) or SEQ ID NO:11 (R-22), In some embodiments, the siRNA molecule that may be part of the therapeutic composition may be a traditional monofunctional siRNA molecule or a bifunctional siRNA molecule having a functional antisense strand and a complementary sense strand. According to some embodiments, such a traditional or bifunctional siRNA molecule may be designed to target one or more of Bcl6, STAT3, c-myc, Bcl2, Cyclin D1, Cyclin D2, Cyclin E2 or syk. In some embodiments, a monofunctional siRNA molecule may target Cyclin D1 (Design 1: SEQ ID NO:1 (sense), SEQ ID NO:2 (antisense); Design D2: SEQ ID NO:3 (sense), SEQ ID NO:4 (antisense)) or STAT3 (SEQ ID NO:7 (sense), SEQ ID NO:8 (antisense)).

In some embodiments, the aptamer-siRNA chimeras that may be part of the therapeutic composition may be any one or more of (i) a sense strand with the sequence SEQ ID NO:37, SEQ ID NO:38 or SEQ ID NO:39 and an antisense strand having the sequence SEQ ID NO:40 (CCND1 27-mer Dicer substrate siRNA with R-1, R-14 or R-22 aptamer—Design 1); (ii) a sense strand having the sequence SEQ ID NO:41, SEQ ID NO:42 or SEQ ID NO:43 and an antisense strand having the sequence SEQ ID NO:43 (CCND1 27-mer Dicer substrate siRNA with R-1, R-14 or R-22 aptamer—Design 2); (iii) a sense strand with the sequence SEQ ID NO:46 and an antisense strand having the sequence SEQ ID NO:47 (R-1-STAT3 27-mer OVH Chimera); or (iv) a sense strand with the sequence SEQ ID NO:49 and an antisense strand having the sequence SEQ ID NO:48 (R-1-STAT3 27-mer SWAP Chimera).

The therapeutic composition may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The therapeutic compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLES

Example 1

B Cell Specific Delivery of siRNA Mediated by a BAFF Ligand Construct

Figure 3B:
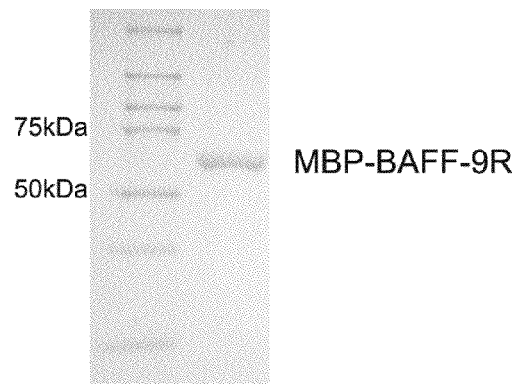
FIG. 3B illustrates the purification of the MBP-His-BAFF-9R construct according to some embodiments. The SDS-Page gel shows the purified MBP-His-BAFF-9R fusion protein construct.
Figure 4:
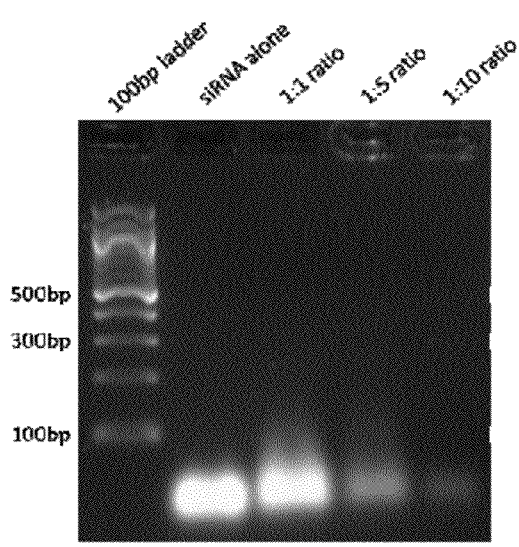
FIG. 4 is a representative gel from a gel retardation experiment showing different ratios of siRNA to MBP-His-BAFF-9R (1:1, 1:5, 1:10) compared to siRNA alone, analyzed on a 2% agarose gel.

A fusion protein of BAFF with an additional 9 arginine residues (MBP-His-BAFF-9R) was over-expressed in E. coli and purified the protein by His-affinity- and Maltose-affinity chromatography. FIG. 3A shows the full fusion construct schematically, and FIG. 3B shows an SDS-Page gel of the purified construct. The 9 arginine tail is responsible for the binding of the negatively charged RNA and the BAFF is used for specifically binding to B cells and internalization. The resulting protein, MBP-His-BAFF-9R, was able to bind siRNA in a concentration dependent manner via electrostatic interactions (FIG. 4).

Figure 5:
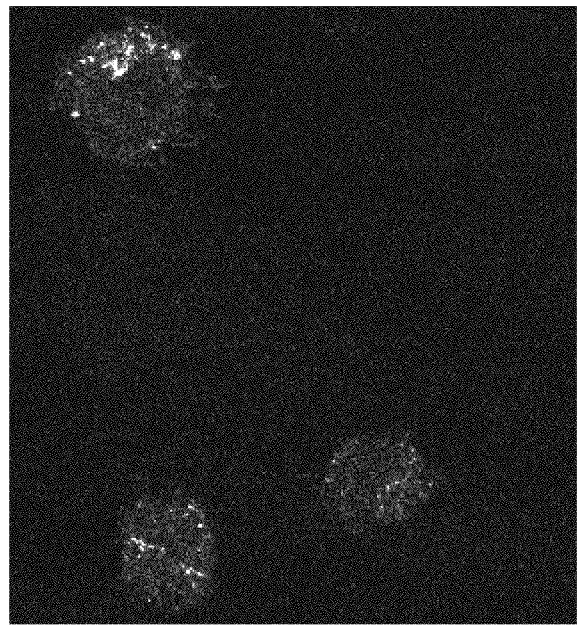
FIG. 5 is a confocal microscope picture of Jeko-1 cells 4 hours after incubation with the preformed complex of MBP-BAFF-9R and Cy3-labeled siRNA, showing that the complex was internalized by the cells.
Figure 6A:
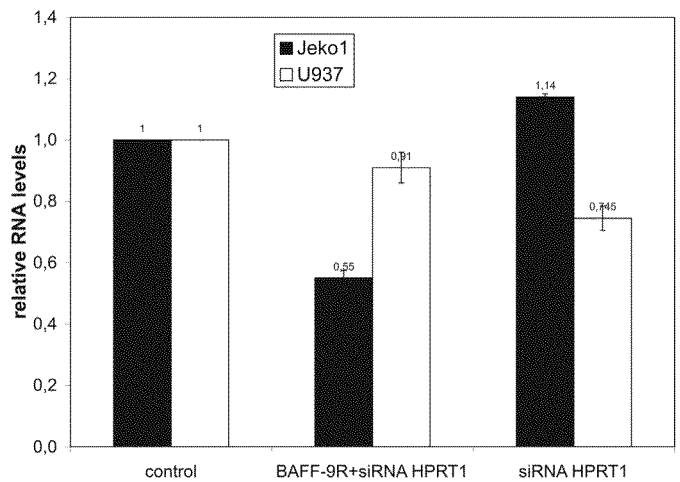
FIG. 6A shows a bar graph illustrating the results of a quantitative RT-PCR experiment for HPRT1 mRNAs extracted from Jeko1 and U937 cells 72 h after transfection of 100 nM siRNAs via MBP-BAFF-9R construct.
Figure 6B:
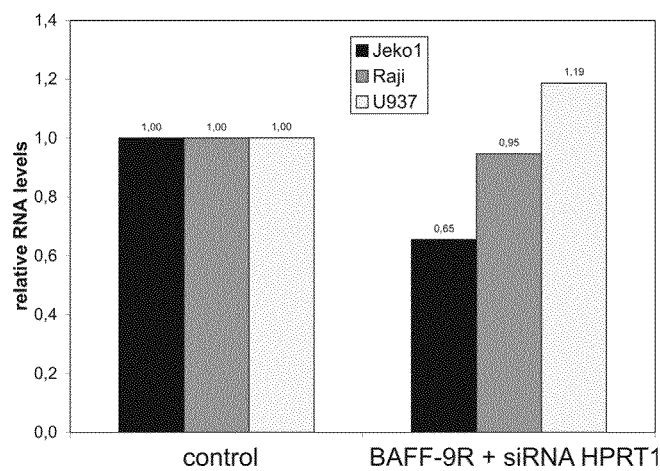
FIG. 6B shows a bar graph illustrating the results of a quantitative RT-PCR experiment for HPRT1 mRNAs extracted from Jeko1, Raji and U937 cells 72 h after transfection of 300 nM siRNAs via MBP-BAFF-9R.
Figure 6C:
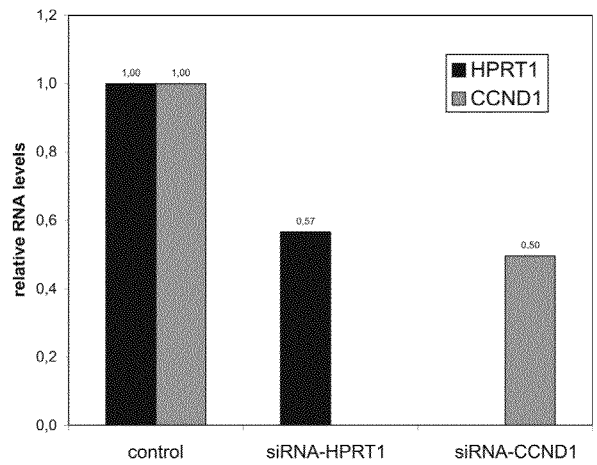
FIG. 6C shows a bar graph illustrating the results of a quantitative RT-PCR experiment for HPRT1 and CCND1 mRNAs extracted from Jeko1 cells 48 h after transfection via electroporation, a conventional transfection method, as a comparison.

It was shown that BAFF was selectively internalized into BAFF-R positive cells, even when extended with the C-terminal 9 arginines and the N-terminal MBP and 6×His tag (FIG. 5). Further, delivery of siRNA was successful in BAFF-R expressing Jeko-1 cells determined by gene knockdown of HPRT1 (control) and CCND1 by quantitative RT-PCR (qRT-PCR) (FIG. 6). Additional experimental details are described in Hergenreider, E., B Cell specific delivery system for siRNA, (May 2008) (unpublished M. S. Thesis, Friedrich-Alexander-Universitat Erlangen-Nümberg), which is incorporated by reference in its entirety, as if fully set forth herein.

Example 2

Generation of Bifunctional siRNA

Figure 7A:
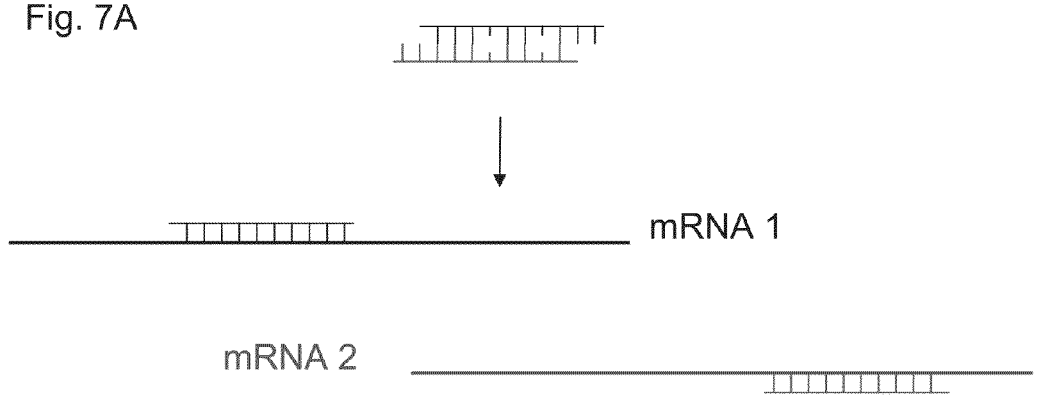
FIG. 7A is a schematic overview of bifunctional siRNA mechanism of design according to some embodiments.
Figure 7B:
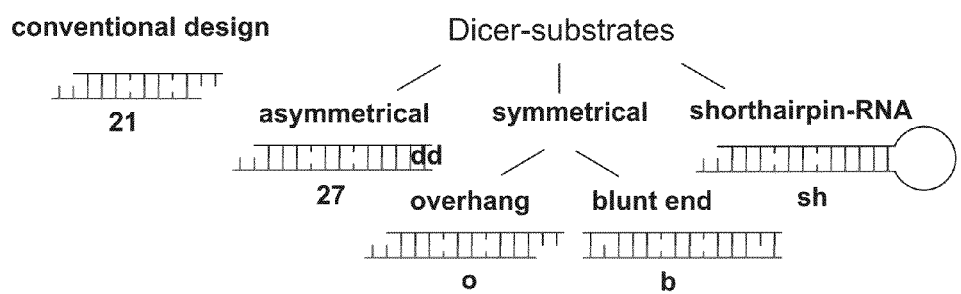
FIG. 7B is a schematic overview of different bifunctional siRNA designs according to some embodiments.

Several bifunctional siRNA were designed that contain two fully target-complimentary and functional antisense strands against two targets at the same time. FIG. 7A illustrates the principle of bifunctional siRNA construction for the two antisense strands, mRNA1 and mRNA2. The two antisense strands can be used to design several different bifunctional siRNAs as illustrated in FIG. 7B.

The first generation of bifunctional siRNAs against STAT3 and Bcl6 mRNA were designed by using a computer algorithm for guide-only siRNAs (http://www.mpibpc.mpg.de/groups/fuehrmann/siRNA) considering symmetrical end stabilities for the last 2-3 nucleotides (Hossbach et al. 2006). The siRNAs were chemically synthesized as 21 mer siRNAs or Diver substrate 25/27mers (Amarzguioui et al. 2006).

Figure 8A:
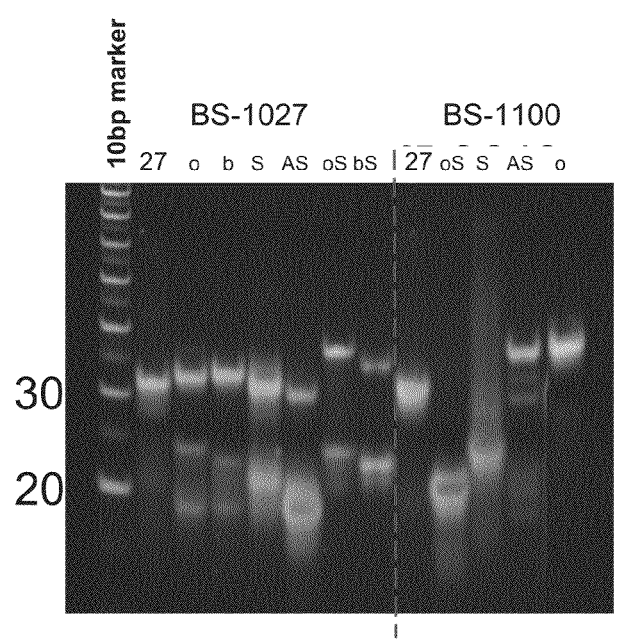
FIG. 8A is a gel representing an analysis of bifunctional siRNA duplexes and corresponding single strands on a 15% native gel stained with SYBR Gold.
Figure 8B:
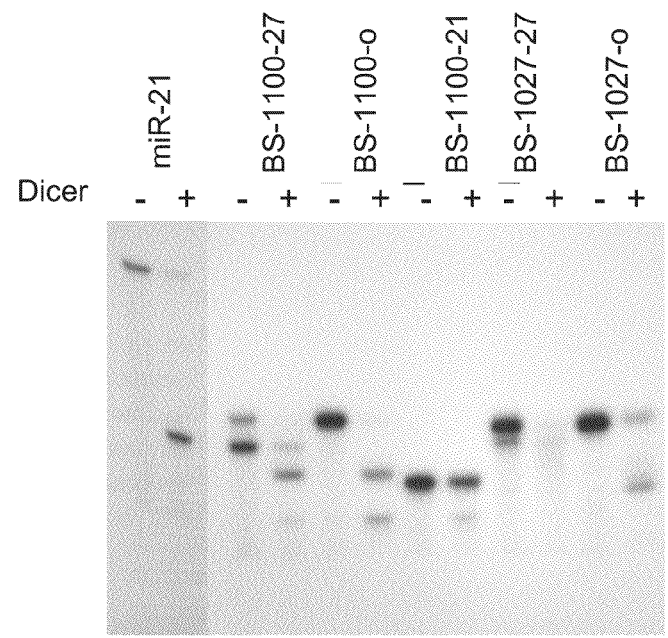
FIG. 8B is a gel representing an analysis of Dicer-substrates that were processed into smaller molecules by Dicer. The indicated siRNAs were incubated in the presence (+) or absence (−) of recombinant human Dicer and then analyzed on a 15% denaturing polyacrylamide gel stained with SYBR Gold. The pre-miRNA miR-21 served as a positive control.
Figure 9A:
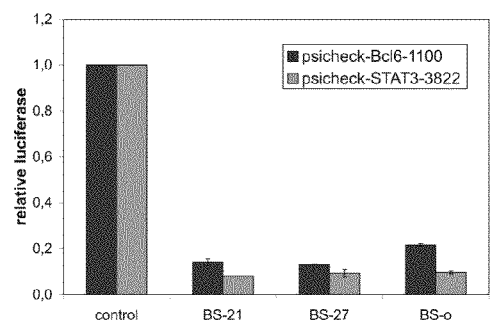
FIG. 9A is a bar graph illustrating the results for the dual-luciferase reporter assays for bifunctional siRNA BS-1100 against Bcl6 and STAT3 in different designs, 24 hours after transfection of 10 nM siRNA in HEK293 cells.
Figure 9B:
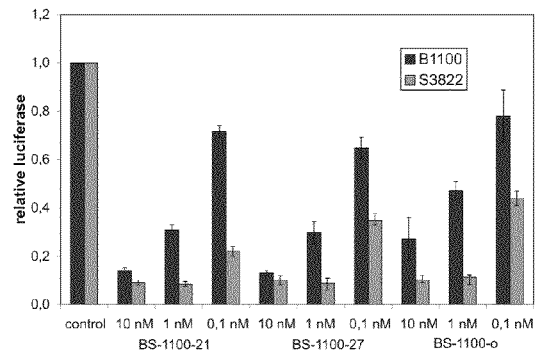
FIG. 9B is a bar graph illustrating the results for the dual-luciferase reporter assays for bifunctional siRNA BS-1100 against Bcl6 and STAT3 in different designs, 24 hours after transfection of titration of siRNA concentration in HEK293 cells.
Figure 9C:
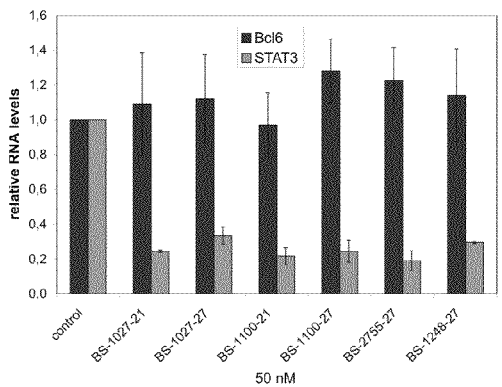
FIG. 9C is a bar graph illustrating the results for real-time PCR performed for siRNAs against STAT3 and Bcl6 mRNA extracted 48 hours after transfection of 50 nM synthetic siRNAs in HEK293 cells.
Figure 9D:
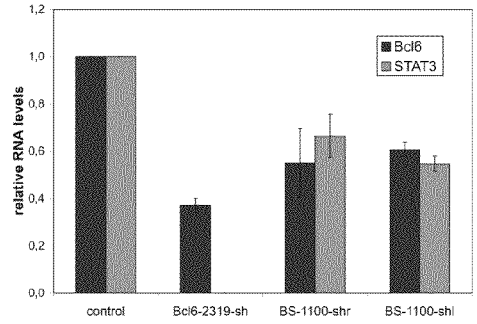
FIG. 9D is a bar graph illustrating the results for real-time PCR performed for siRNAs against STAT3 and Bcl6 mRNA extracted 48 hours after transfection of 100 ng shRNA of BS-1100 in HEK293 cells.

The first generation bifunctional siRNA duplexes and corresponding single strands were analyzed on a 15% native gel stained with SYBR Gold (FIG. 8A). After being processed into smaller molecules by Dicer, the Dicer-substrates, the first generation siRNAs were incubated in the presence (+) or absence (−) of recombinant human Dicer, then analyzed on a 15% denaturing polyacrylamide gel stained with SYBR Gold. The pre-miRNA miR-21 served as a positive control (FIG. 8B). A duel luciferase reporter assay for bifunctional siRNA BS-1100 against Bcl6 and STAT3 in different designs was performed 24 hours after HEK293 cells were transfected with A) 10 nM siRNA (FIG. 9A) or titration of siRNA concentration (FIG. 9B). Real-time PCR was performed for siRNAs against STAT3 and Bcl6 mRNA extracted for HEK 293 cells 48 hours after transfection of 50 mM synthetic siRNAs (FIG. 9C) and 100 ng shRNA of first generation bifunctional siRNA BS-1100 (FIG. 9D).

Figure 10:
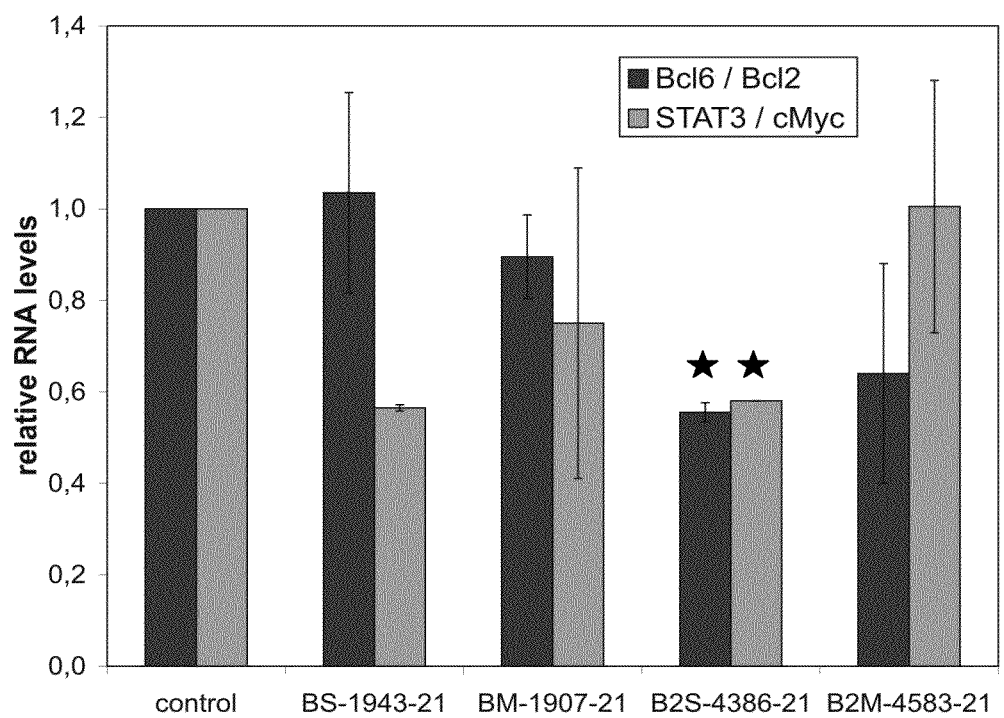
FIG. 10 is a bar graph illustrating the results of real-time PCT performed for siRNAs against Bcl6, Bcl2, STAT3 and c-myc mRNA, respectively, extracted from HEK293 cells 48 hours after transfection of 50 mM synthetic 21 mer siRNAs.

For the second generation of bifunctional siRNAs the same computer algorithm was used as for the first generation, but allowing only the minimum number of mismatches. Additionally, thermodynamic end stabilities of the last 4-5 nucleotides and the target accessibility were taken into account. Bcl2 and c-myc were also considered as target genes. HEK293 cells were transfected with 50 mM synthetic 21mer bifunctional siRNAs BS-1943-21 (against STAT3 and Bcl6), BM 1907-21 (against c-myc and Bcl6), B2S-4386-21 (against c-myc and Bcl2) and B2M-4583-21 (against STAT3 and Bcl2). After 48 hours, real-time PCR was performed for the bifunctional siRNAs. The second generation bifunctional siRNA, B2S-4386-21, was able to effectively silence both targeted oncogenes (FIG. 10, stars).

Table 1 explains the experimental results for the first and second generations of bifunctional siRNA. The results are described above by a combination of various prediction parameters by different computer algorithms for first and second generation of bifunctional siRNA design.

TABLE 1

First and Second Generation bifunctional siRNAs

| | siRNA ID | Target | Refseq | Relative RNA levels | Sfold acc. | Diff Thermo ends [5] | efficacy | RISC entry [5] | Eff + RISC entry [5] | miRNA score | miRNA score + eff + RISC entry [5] |
|---|---|---|---|---|---|---|---|---|---|---|---|
| 1st Generation | BS-1027 | STAT3 BCL6 | NM_003150 NM_001706 | 0.51 1.08 | 0.45 0.30 | 3.90 -3.90 | -0.14 -0.49 | 1.00 -1.00 | 0.86 -1.49 | 0.00 0.00 | 0.86 -1.49 |
| | BS-1100 | STAT3 BCL6 | NM_003150 NM_001706 | 0.18 0.72 | 0.40 0.57 | 2.50 -2.50 | 0.11 0.06 | 1.00 -1.00 | 1.11 -0.94 | 1.50 0.00 | 2.61 -0.94 |
| | BS-2755 | BCL6 STAT3 | NM_001706 NM_003150 | 0.68 0.15 | 0.42 0.33 | -8.70 8.70 | -0.09 0.49 | -1.00 1.00 | -1.09 1.49 | 1.00 2.23 | -0.09 3.72 |
| 2nd Generation | BS-1943 | STAT3 BCL6 | NM_003150 NM_001706 | 0.57 1.05 | 0.34 0.53 | -0.40 0.40 | 0.03 -0.26 | 0.00 0.00 | 0.03 -0.26 | 1.00 0.00 | 1.03 -0.26 |
| | BM-1907 | MYC BCL6 | NM_002467 NM_001706 | 0.77 0.90 | 0.31 0.47 | -0.50 0.50 | -0.26 0.00 | 0.00 0.00 | -0.26 0.00 | 0.00 0.00 | -0.26 0.00 |
| | B2M-4583 | MYC BCL2 | NM_002467 NM_000633 | 1.02 0.63 | 0.37 0.60 | -0.90 0.90 | 0.15 -0.11 | 0.00 0.00 | 0.15 -0.11 | 0.00 2.00 | 0.15 1.89 |

TABLE 1-continued

First and Second Generation bifunctional siRNAs

| siRNA ID | Target | Refseq | Relative RNA levels | Sfold acc. | Diff Thermo ends [5] | efficacy | RISC entry [5] | Eff + RISC entry [5] | miRNA score | miRNA score + eff + RISC entry [5] |
|---|---|---|---|---|---|---|---|---|---|---|
| B2S-4386 | STAT3 | NM_003150 | 0.57 | 0.30 | 4.5 | 0.82 | 1.00 | 0.82 | 1.50 | 2.32 |
| | BCL2 | NM_000633 | 0.57 | 0.50 | -4.5 | -1.44 | -1.00 | -1.44 | 2.00 | 0.56 |
| | | R | | 0.11 | -0.52 | -0.52 | -0.56 | -0.61 | -0.73 | -0.84 |
| | | $R^2$ | | 0.01 | 0.27 | 0.27 | 0.31 | 0.38 | 0.53 | 0.70 |
| | | p-value | | 0.696 | .057 | 0.055 | 0.037 | 0.020 | 0.003 | 0.000 |

"Sfold acc." shows the average target accessibility as predicted by Sfold. "Diff. thermo ends" shows the difference in predicted thermodynamic end stability in the duplex considering 5 nucleotides at the ends. "Efficacy" is the predicted cleavage efficacy for a conventional siRNA designed against the same target. "RISC entry" indicates whether the strand is favored (1), unfavored (-1) or undecided (0) for RISC uptake. "miRNA score" predicts the likelihood of the strand causing miRNA-like translation inhibition. Considering these parameters, a third generation of bifunctional siRNAs were designed and shown in Table 2 below.

TABLE 2

Third Generation bifunctional siRNAs.

| siRNA ID | Target | Refseq | Relative RNA levels | Sfold acc. | Diff Thermo Ends [5] | Efficacy | RISC entry [5] | miRNA score | miRNA score + eff + RISC entry [5] |
|---|---|---|---|---|---|---|---|---|---|
| B2S-4543-1490 | Bcl2 | NM_000633 | 0.85 | 0.46 | -1.3 | 0.16 | -1 | 1.5 | 0.66 |
| | STAT3 | NM_003150 | 0.33 | 0.48 | 1.3 | 0.34 | 1 | 2 | 3.34 |
| MB2-2019-2086 | cmyc | NM_002467 | 0.40 | 0.62 | 0.3 | 0.35 | 0 | 1 | 1.35 |
| | Bcl2 | NM_000633 | 0.31 | 0.42 | -0.3 | 0.26 | 0 | 1.5 | 1.76 |
| sykB2-700-4626 | syk | NM_003177 | 0.25 | 0.58 | -0.2 | 0.25 | 0 | 1 | 1.25 |
| | Bcl2 | NM_000633 | 0.10 | 0.41 | 0.2 | 0.31 | 0 | 2 | 2.31 |

Figure 11:
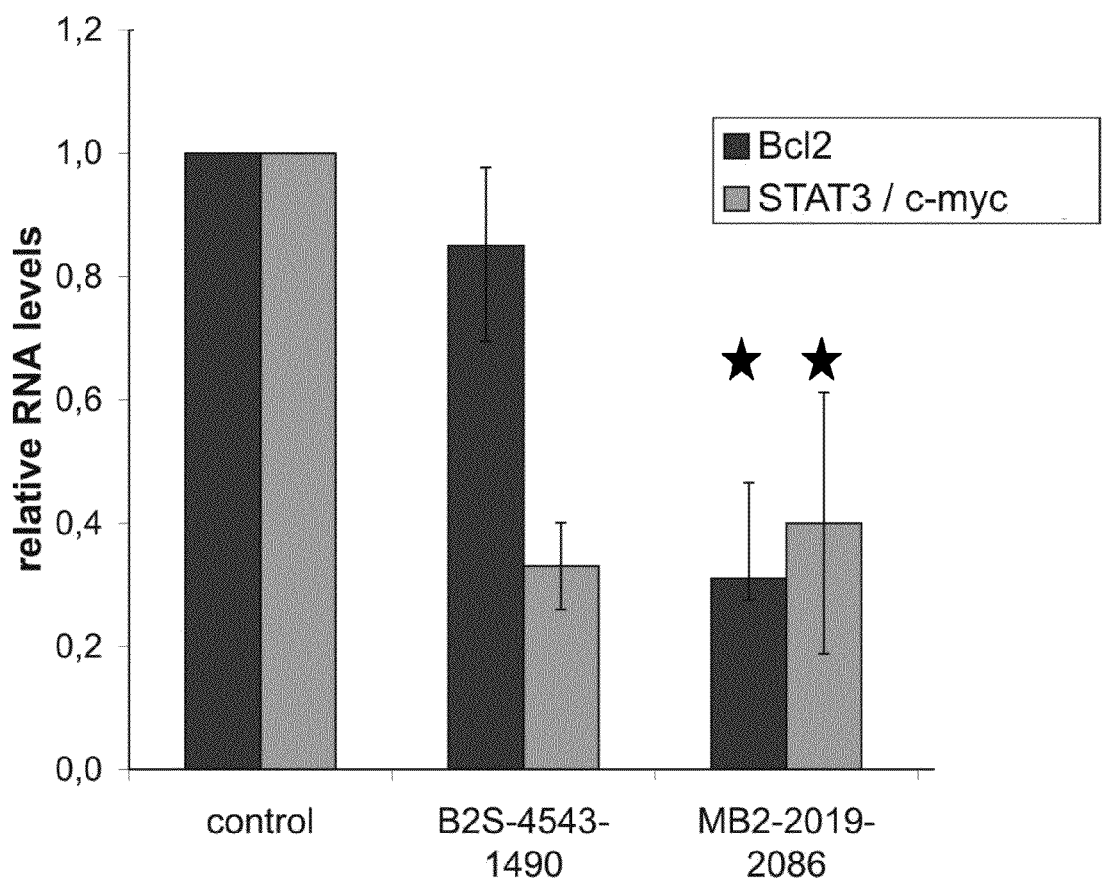
FIG. 11 is a bar graph illustrating the results of real-time PCR performed for siRNAs against Bcl2 and c-myc mRNA, respectively, extracted from HEK293 cells 48 h after transfection of 50 nM synthetic 27mer bifunctional siRNAs.
Figure 12:
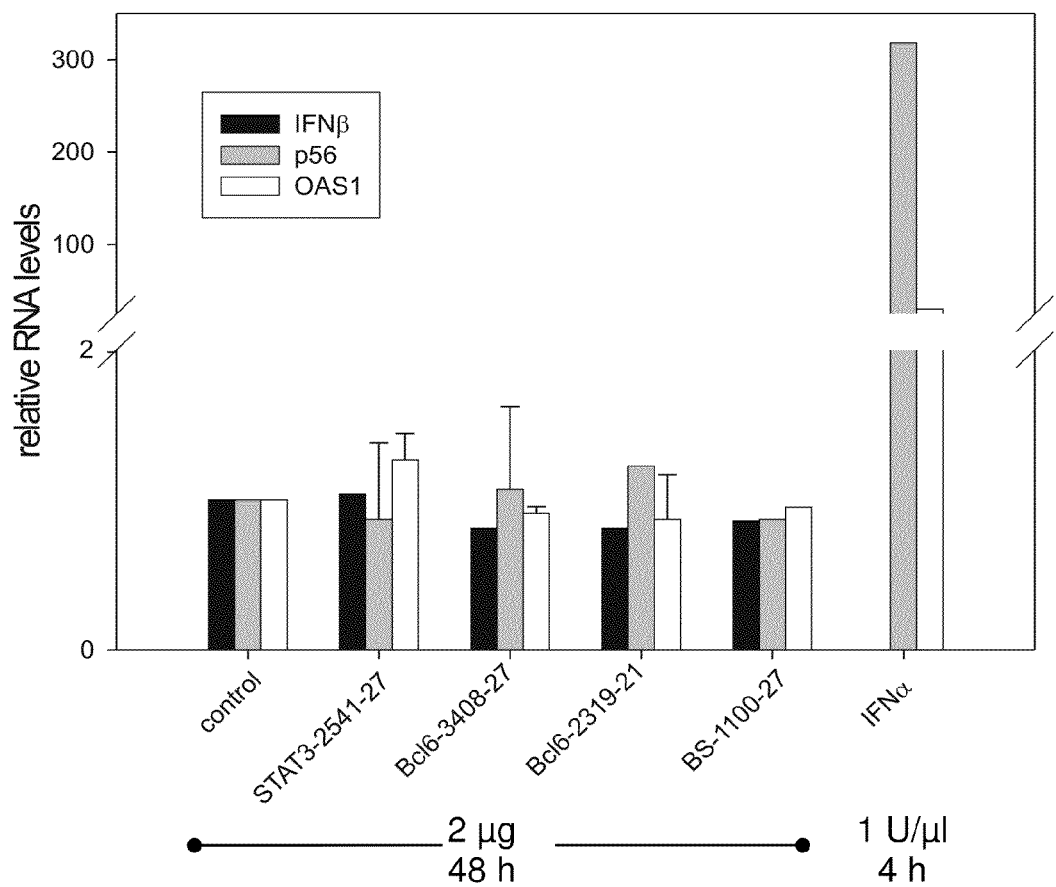
FIG. 12 is a bar graph illustrating the results of real-time PCR performed for IFNγ, p56 and OAS1 mRNAs extracted from Raji cells 48 h after electroporation of 2 µg siRNA following the Amaxa protocol. As positive control, Raji cells were incubated with 1 U/µl IFNα for 4 h. Data was normalized to RPLP0 and is shown relative to the mock transfected control. Experiments were done in duplicate. Similar results were obtained for Daudi, Su-DHL-4 and Su-DHL-6 cell lines.

In an experiment to test the efficacy of the bifunctional siRNAs described above, HEK293 cells were transfected with 50 nM synthetic 27mer bifunctional siRNAs B2S-4543-1490 (against Bcl2 and STAT3) and MB2-2019-2086 (c-myc and Bcl2). After, 48 hours, real-time PCR was performed for the bifunctional siRNAs. The third generation bifunctional siRNA MB2-2019-2086 was able to effectively silence both targeted oncogenes (FIG. 11, stars). None of the bifunctional siRNAs had an influence on the interferon response (FIG. 12), which can sometimes be a concern when using RNAi pathways.

Figure 33:
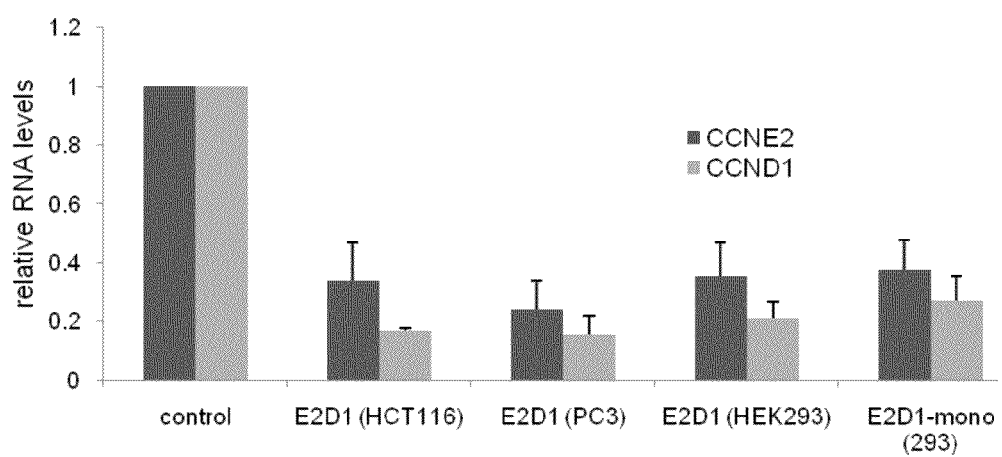
FIG. 33 is a bar graph illustrating relative RNA levels of CCNE2 and CCND1 in HCT116, PC3 and HEK293 cells transfected with E2D1 bifunctional siRNA and with 2 monofunctional siRNAs (E2D1-mono). Evaluation of relative RNA levels was by quantitative PCR (qPCR). Experiments were performed in triplicate.

In a second experiment, an additional bifunctional siRNA was designed using the method described above. The E2D1 siRNA targets Cyclin E2 (CCNE2) and Cyclin D1 (CCND1) simultaneously. In addition, the monofunctional equivalents that target the same sequences in the two target genes (CCNE2 and CCND1) were designed. The monofunctional and bifunctional siRNAs were then transfected into HEK293, PC3 and HCT116 cells to determine whether the bifunctional siRNAs are as efficient as traditional monofunctional siRNAs in knocking down each target gene. As shown in FIG. 33, the bifunctional siRNAs (E2D1) achieve similar gene knockdown in all three cell lines. Further, the knock-down achieved by the bifunctional siRNAs is comparable to the knock-down achieved by the monofunctional siRNAs (E2D1-mono).

The bifunctional siRNAs described above may be combined with a suitable aptamer including, but not limited to, an RNA aptamer (described below) or BAFF ligand aptamer (described above) for specific delivery to B cells.

Example 3

Selection and Function of B Cell Specific Aptamers

Materials and Methods

In addition to applicable materials and methods discussed above and below, the following additional materials and methods were used.

Materials.

Unless otherwise noted, all chemicals were purchased from Sigma-Aldrich, all restriction enzymes were obtained from New England BioLabs (NEB) and all cell culture products were purchased from GIBCO (Gibco BRL/Life Technologies, a division of Invitrogen.). Sources for the other reagents were: DuraScribe T7 transcription Kit (EPICENTRE Biotechnologies); Silencer siRNA Labeling Kit (Ambion); Random primers (Invitrogen); Bio-Spin 30 Columns (Bio-Rad); Microcon YM-30 column (Millipore); Recombinant Human Dicer Enzyme Kit (Ambion); Jeko-1 and CCRF- CEM cells (ATCC); the BAFF-R protein (B-cell Activating Factor Receptor Human Recombinant) obtained from ProSpect (Israel).

Generation of Aptamer RNAs by In Vitro Transcription.

Aptamer RNAs were prepared as previously described (Zhou et al. 2008). For the BAFF aptamers (SEQ ID NO: 7-9), the aptamer core sequences as shown in FIG. 14 are in bold.

```
BAFF-R-1 aptamer:
                                        (SEQ ID NO: 9)
5'-GGGAGGACGAUGCGGGAGGCUCAACAAUGAUAGAGCCCGCAAUGUUGA

UAGUUGUGCCCAGUCUGCAGACGACUCGCCCGA-3'

BAFF-R-14 aptamer:
                                        (SEQ ID NO: 10)
5'-GGGAGGACGAUGCGGAUAACUAUUGUGCUAGAGGGCUUAUUUAUGUGA

GCCGGUUGAUAGUUGCGCAGACGACUCGCCCGA-3'

BAFF-R-22 aptamer:
                                        (SEQ ID NO: 11)
5'-GGGAGGACGAUGCGGAUCCUCCGAAGGUCGCGCCAACGUCACACAUUA

AGCUUUUGUUCGUCUGCAGACGACUCGCCCGA-3'
```

Cell Culture.

Rec-1 cells were purchased from ATCC and cultured in RPMI 1640 supplemented with 10% FBS and 1% Glutamine. OEM cells were purchased from ATCC and cultured in DMEM supplemented with 10% FBS. Jeko-1, Z138 and Grant-519 cells were sustained in RPMI 1640 medium supplemented with 20% FBS (Jeko-1) or 10% FBS and 1% Glutamine. OEM cells were purchased from ATCC and cultured in DMEM and RPMI 1640 supplemented with 10% FBS. CHO-WT and CHO-EE cells were obtained through the AIDS Research and Reference Reagent Program and were grown in GMEM-S. Cells were cultured in a humidified 5% $CO_2$ incubator at 37° C.

Cell-Surface Binding of Experimental RNAs (Flow Cytometry Analysis).

Jeko-1 or CCRF-CEM cells were pelleted and washed with prewarmed binding buffer. $1*10^5$ cells were then resuspended in 50 μL of prewarmed binding buffer containing 400 nM Cy3-labeled experimental RNAs. After incubation at 37° C. for 40 min, cells were washed three times with 500 μL of prewarmed binding buffer, and finally resuspended in 350 μL of binding buffer prewarmed to 37° C. and analyzed by flow cytometry.

Internalization Studies (Live-Cell Confocal Microscopy Analyses).

On the day of the experiments, the Jeko-1, Z138 or CCEF-CEM cells were seeded in the polylysine-coated 35 mm plate (Glass Bottom Dish, MatTek, Ashland, Mass.) with seeding at $8\times10^5$ in the pre-warmed RPMI-1460 medium. Cells were incubated for 0.5-2 hours in a humidified 5% $CO_2$ incubator at 37° C. for attaching on the dish surface. Cy3-labeled RNAs at a 66 nM final concentration were added to media and incubated for live-cell confocal microscopy in a 5% $CO_2$ microscopy incubator at 37° C. The images were collected every 15 min using a Zeiss LSM 510 Meta Inverted 2 photon confocal microscopy system under water immersion at 40× magnification. After 5 hours of incubation and imaging, the cells were stained by treatment with 0.15 mg/mL Hoechst 33342 (nuclear dye for live cells, Molecular Probes, Invitrogen, CA) according to the manufacturer's instructions. The images were collected as described previously.

qRT-PCR Analysis.

Jeko-1 cells were treated directly with the experimental RNA (400 nM). After 2~6 days of incubation, total RNAs were isolated with STAT-60 (TEL-TEST "B", Friendswood, Tex.). Expression of the CCND1 coding RNAs was analyzed by quantitative RT-PCR using 2×iQ SyberGreen Mastermix (B10-RAD) and specific primer sets at a final concentration of 400 nM. Primers were as follows:

CCND1 1173-Forward: 5'-CTC CTC TCC GGA GCA TTT TGA TA-3' (SEQ ID NO:50)
CCND1 1284-Reverse: 5'-TTA AAG ACA GTT TTT GGG TAA TCT-3' (SEQ ID NO:51)
RPLP0-Forward: 5'-GGC GAO CTG GAA GTC CAA-3' (SEQ ID NO:52)
RPLP0-Reverse: 5'-CCA TCA GCA CCA CAG CCT TC-3' (SEQ ID NO:53).

RNA-Stat60 was used to extract total RNA according to the manufacturer's instructions (Tel-Test). Residual DNA was digested using the DNA-free kit per the manufacturer's instructions (Ambion, CA). cDNA was produced using 2 μg of total RNA Moloney murine leukemia virus reverse transcriptase and random primers in a 15 μL reaction according to the manufacturer's instructions (Invitrogen, CA). RPLP0 expression was used for normalization of the qPCR data.

Figures 34A, 34B:
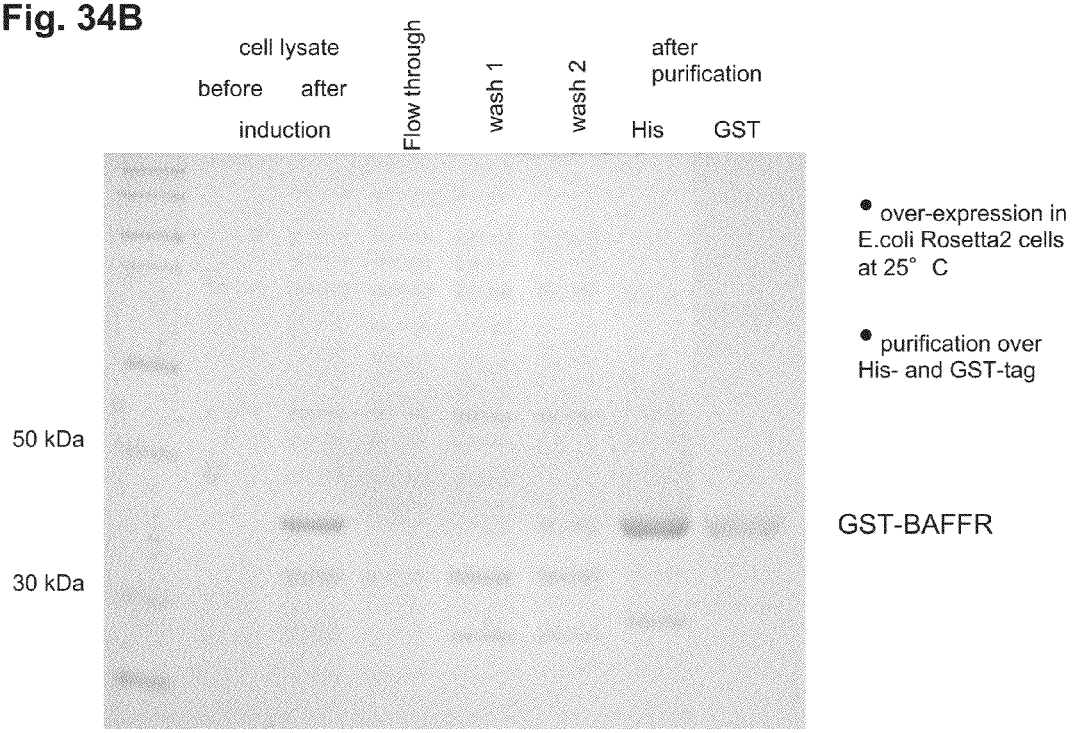
FIG. 34A illustrates the construction of the BAFF-R-6× His-GST construct according to some embodiments. The schematic diagram of the BAFF-R-6×His-GST construct contains a GST tag at the N-terminus and a 6×His tag at the C-terminus.
FIG. 34B illustrates the purification of the BAFF-R-6×His-GST construct according to some embodiments. The SDS-Page gel shows the MBP-His-BAFF-9R fusion protein construct at different stages of purification.

BAFF-R Fusion Protein not Suitable for In Vitro Selection of RNA Aptamers Against BAFF-R In a first attempt to select aptamers against BAFF-R, a BAFF-R fusion protein, BAFF-R-6×His-GST, was used to carry out an in vitro SELEX procedure. To generate the BAFF-R-6×His-GST fusion protein, the extracellular part of the cell-surface marker BAFF-R was expressed as His-tagged (at the C-terminal end) Glutathione S-Transferase (GST, at the N-terminal end) fusion proteins using a recombinant bacterial system (FIG. 34A). The fusion protein was then purified by targeting the His-tag and/or the GST (see FIG. 34B). It was thought that use the BAFF-R-6×His-GST fusion protein for selection of aptamers would be advantageous because the target protein (BAFF-R) could be easily immobilized by exposing the GST affinity tag to appropriate or complementary beads or matrix during each selection step.

Preparation of the RNA Library.

To stabilize the aptamers in vivo, a 2'-Fluoropyrimidine RNA library was produced by in vitro transcription in the presence of 2'-Fluorouridine-Triphosphate and 2'-Fluorocytosine-Triphosphate using a modified T7-RNA-Polymerase that includes the modified nucleotides with high efficiency. The T7-Transcription protocol is illustrated as follows. First, the following components were combined at room temperature to make a 20 μl sample solution (Table 3):

TABLE 3

Components in T7 transcription protocol

| Component | Stock Concentration | End Concentration | Volume (μl) |
|---|---|---|---|
| dsDNA | | 2 μg/31 pmol | |
| Buffer | 10× | 1× | 2 |
| ATP | 50 mM | 2.5 mM | 1 |
| GTP | 50 mM | 2.5 mM | 1 |
| CTP | 50 mM | 2.5 mM | 1 |
| UTP | 50 mM | 2.5 mM | 1 |
| DTT | 100 mM | 10 mM | 2 |
| Enzymemix | | | 1 |
| H2O | | | |
| | | | 20 |

The sample solution above was then incubated at 37° C. for 4 hours, followed by DNAse treatment. Briefly, 1 μl of DNAse was added per 1 μg DNA, incubated at 37° C. for 30 min.

Figure 35:
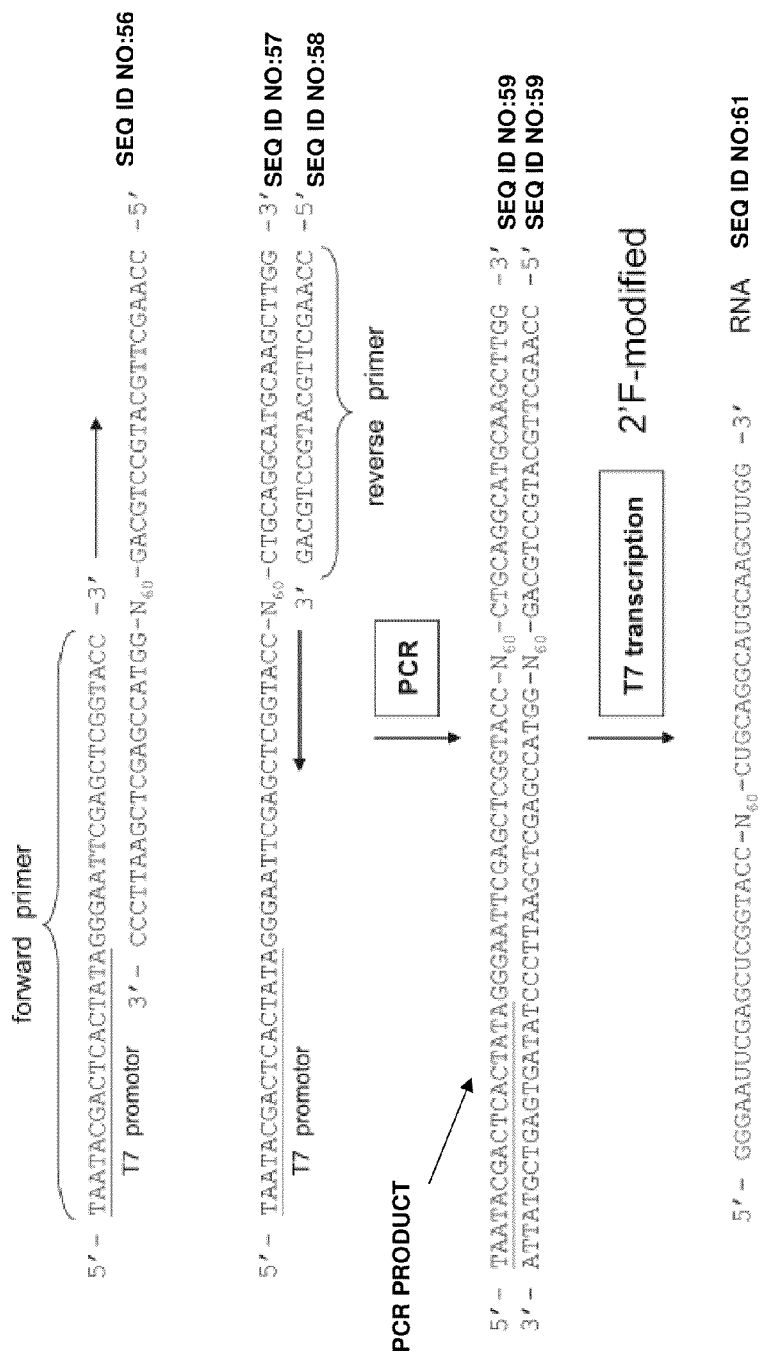
FIG. 35 illustrates the process of generating an RNA library to be used with the SELEX process according to some embodiments.

The RNA library was also radioactively labeled with γ-$^{32}$P-ATP by T4 polynucleotide kinase to follow the binding to the target molecule. The process of producing the RNA library, as well as the forward and reverse primers used, is shown in FIG. 35.

In Vitro Selection of RNA Aptamers.

Selection of RNA aptamers by the SELEX process is performed using a series of selection "rounds," each round including a pre-selection step (a), a selection step (b), a filter assay step (c), and a reverse transcriptase and amplification step (d). The gel-purified RNA molecules were refolded in their unique structure and during the pre-selection step, incubated with the matrix (GST-resin) without the target molecule to remove unspecific binders. After the pre-selection step, the reduced RNA library was incubated with the immobilized target molecule for the selection step. The best binders were recovered, reverse transcribed and amplified to generate a new enriched RNA pool for the next round of selection. The protocol for each round of SELEX selection against BAFF-R-6xHis-GST (dsDNA:64680; RNA: 25069) was as follows.

Preselection: RNA from the RNA library generated above was suspended in 1× Selection buffer, followed by heating to 75° C. for 2 minutes and then cooled down to room temperature for 45 minutes. Scintillation was counted. The gel-purified RNA molecules were then incubated with the GST-resin at a ratio of GST:RNA of 2:1. (GST: 26.3 kDa; 38 μM; 1 μg/μl) The 20 μl RNA sample above was thus added to 40 μl GST-resin (80 μl slurry) (200 μg binding capacity), resulting in 5 mg protein per 1 ml resin. The resin was washed 2 times with 200 μl PBS, and the GST was allowed to bind for 0.5 hours in in 200 μl PBS, followed by washing 3 times with 500 μl of 1× selection buffer. Next, 100 μl RNA was added and incubated for 0.5-1 hour. The flow-through was collected and was washed 1 time with 100 μl 1× selection buffer and scintillation counter was used to court radioactivity. The level of resin-bound radioactivity compared to the total amount of radioactivity applied to the resin is the % binding.

Selection: The preselected RNA pool was incubated with BAFF-R: RNA (BAFF-R: 33.8 μM, 17.4 μM (calculate with 16 μM), 0.6 μg/μl; t-RNA: 3 μg/μl, 114 μM) The resin was washed 2 times with 200 μl of PBS. BAFF-R was allowed to bind for 0.5 hours in 200 μl PBS, then was (i) washed 4 times with 500 μl 1× washing buffer, (ii) washed 1 time with 500 μl 1× washing buffer for 0.5 hour and (iii) washed 2 times with 500 μl 1× selection buffer. The flow through was then added after preselection, incubated for 1 hour and then washed 3 times with 500 μl 1× selection buffer. Next, the BAFF-R was eluted 2 times with 100 μl elution buffer, 95° C., 5 min and a scintillation count was taken. A phenol/chloroform extraction was then performed, followed by EtOH precipitation.

Reverse transcription: The following components were combined to make a 20 μl sample solution (Table 4).

TABLE 4

Components in sample solution.

|  | Stock concentration | End concentration | Volume (μl) |
|---|---|---|---|
| RNA (10 pg-5 μg) |  |  | 9 |
| dNTPs | 10 mM | 1 mM | 2 |
| Reverse Primer | 20 μM | 20 pmol | 1 |
| Buffer | 5× | 1× | 4 |

TABLE 4-continued

Components in sample solution.

|  | Stock concentration | End concentration | Volume (μl) |
|---|---|---|---|
| DTT | 0.1M | 5 mM | 1 |
| RNase Out | 40 u/μl | 40 U | 1 |
| RT | 15 U/μl | 15 U | 1 |
| H2O |  |  | 1 |
|  |  |  | 20 |

The sample solution was incubated at 65° C. for 5 min, 55° C. for 50 min, and 85° C. for 10 min.

Amplification by polymerase chain reaction (PCR): The following components were combined at room temperature to make a 20 μl sample solution (Table 5).

TABLE 5

Components of sample solution

|  | Stock concentration | End concentration | Volume (μl) |
|---|---|---|---|
| cDNA |  |  | X |
| dNTPs | 10 mM | 0.2 mM | 1 |
| Forward Primer | 100 μM | 0.5 μM | 0.25 |
| Reverse Primer | 100 μM | 0.5 μM | 0.25 |
| Buffer | 10× | 1× | 5 |
| Taq | 5 U/μl | 2.5 U | 0.4 |
| H2O |  |  |  |
|  |  |  | 50 |

The sample solution was incubated at 94° C. for 5 minutes, followed by 94° C. for 30 seconds, 63° C. for 30 seconds and 72° C. for 30 seconds for 15 cycles. Finally, the sample solution was incubated at 72° C. for 5 minutes.

Unspecific binding of RNA molecules was reduced by introducing increasing amounts of tRNAs, decreasing amounts of BAFF-R and more stringent buffer and washing conditions to select only the RNA molecules with the highest affinity to the target molecule. The selection was carried out at room temperature (FIG. 36, SELEX-1 (25° C.)) to test selection conditions and at 37° C. (FIG. 36, SELEX-2 (37° C.)) to enrich binders with highest affinity at physiological temperature. Binding affinity of enriched RNA pools after certain rounds were determined by a filter assay, the protocol of which is as follows.

The RNA was suspended in 1× selection buffer with BSA followed by a T-program which heats the suspension to 75° C., then cools to room temperature. The filter is then washed 3 times with 1× selection buffer without BSA (300 μl). Next, the suspension is dripped onto the filter to allow slow flow through the filter (Millipore, HAWP01300 MF membrane 0.45 μm, 13 mm). Wash with 100-200 μl 1× selection buffer without BSA. The radioactivity retained on the filter was counted by a multi-purpose scintillation counter. Next, tRNA and BAFFR was added and incubated for 1 hour at 37° C. The filter is then washed 3 times with 20 μM tRNA in 1× selection buffer w/o BSA 300 μl. Flow through was performed again, followed by washing 5 times in 1× selection buffer w/o BSA (300 μl). The filter was then cut and elution was performed 2 times with 7M urea 150 μl, 95° C. for 5 min. A phenol/chloroform extraction was then performed, followed by EtOH precipitation.

The level of the filter-bound radioactivity compared to the total amount of radioactivity applied to the membrane represents the % binding. The % binding represents binding enrichment as SELEX progresses.

Figure 37:
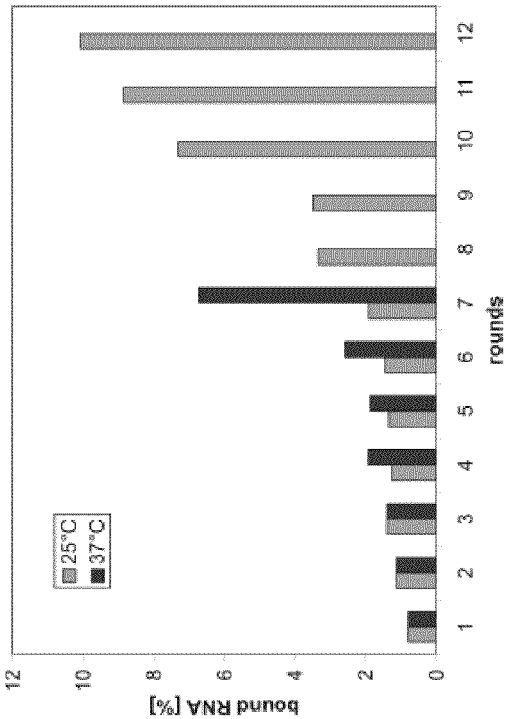
FIG. 37 is a bar graph illustrating the results of a SELEX aptamer selection process for the BAFF-R-6×His-GST construct according to the results shown in FIG. 37.

Monitoring the selection after each round revealed an enrichment of binders starting at round 8, and the enrichment saturated at approximately round 12. An overview of the selection process and a graph of the results of this selection protocol is illustrated in FIG. 37. Subsequent measurement of the binding affinity to the target showed only unspecific binding to the resin and/or GST even though a preselection was performed against the matrix prior to each selection round. Thus, the GST-resin was not suitable for the selection process for BAFF-R aptamers because the nucleic acid molecules were unspecifically bound to this matrix. A different approach, as described below, that uses nitrocellulose filters to separate bound RNA-BAFF-R complexes from unbound RNA molecules, was successful for selection of RNA aptamers against BAFF-R.

Successful Selection and Identification of RNA Aptamers Against Human BAFF-R Protein.

An in vitro SELEX procedure was used to select 2'-fluoropyrimidine modified RNA aptamers which selectively bind the human recombinant BAFF-R protein. To carry out the SELEX an RNA library containing a central stretch of 50 random nucleotides was synthesized by in vitro T7 transcription.

Preparation of the RNA Library.

The starting DNA library contained 50 nucleotides of random sequences and was synthesized by Integrated DNA Technologies (Coralville, Iowa). The random region is flanked by constant regions, which include the T7 promoter (underlined below) for in vitro transcription and a 3' tag for RT-PCR. The 5' and 3' constant sequences are 5'-TAATAOGAOTCACTATAGGGA GGA CGA TGC GG—3' (32 mer) (SEQ ID NO:54) and 5'-TCG GGC GAG TCG TCT G—3' (16 mer) (SEQ ID NO:55), respectively. The DNA random library (0.4 µM) was amplified by PCR using 3 µM each of 5'- and 3'-primers, along with 2 mM MgCl$_2$ and 200 µM of each dNTP. In order to preserve the abundance of the original DNA library, PCR was limited to ten cycles.

After the PCR reactions (10 reactions, 100 µL per reaction), the amplified dsDNA pool was recovered using a QIAquick Gel purification Kit. The resulting dsDNA was converted to an RNA library using the DuraScription Kit (Epicentre, Madison, Wis.) according to the manufacturer's instructions. In the transcription reaction mixture, CTP and UTP were replaced with 2'-F-CTP and 2'-F-UTP to produce ribonuclease resistant RNA. The reactions were incubated at 37° C. for 6 h, and subsequently the template DNA was removed by DNase I digestion. The transcribed RNA pool was purified in an 8% polyacrylamide/7 M urea gel. The purified RNA library was quantified by UV spectrophotometry.

In Vitro Selection of RNA Aptamers.

The SELEX process includes several steps as described above and was performed principally as previously described (Tuerk and Gold 1990). In every selection round, the RNA pools were refolded in HBS buffer (10 mM HEPES pH 7.4, 150 mM NaCl, 1 mM CaCl$_2$, 1 mM MgCl$_2$, 2.7 mM KCl), heated to 95° C. for 3 min and then slowly cooled to 37° C. Incubation was continued at 37° C. for 10 min.

Generally, in order to minimize and remove nonspecific binding with the nitrocellulose filters, the refolded RNA pools were pre-adsorbed to a nitrocellulose filter (HAWP filter, 0.22 µm) for 30 min, prior to incubation with the human BAFF-R protein. The pre-cleared RNA pool was incubated with the target protein in low-salt RNA binding buffer (10 mM HEPES pH 7.4, 50 mM NaCl, 1 mM CaCl$_2$, 1 mM MgCl$_2$, 2.7 mM KCl, 10 mM DTT, 0.01% BSA and tRNA) for 30 min for SELEX rounds 1 to 4. After the fourth round of SELEX, a high-salt RNA binding buffer (10 mM HEPES pH 7.4, 150 mM NaCl, 1 mM CaCl$_2$, 1 mM MgCl$_2$, 2.7 mM KCl, 10 mM DTT, 0.01% BSA and tRNA) was used. With the SELEX progress, the amount of BAFF-R protein was reduced and competitor tRNA was increased in order to increase the stringency of aptamer selection.

For the first cycle of selection, the pre-cleared random RNA pool (73 µg, 2.7 nmol, 1.6×10$^{15}$ molecules) and BAFF-R protein (0.65 nmol, RNA/Protein ratio 4/1) were incubated in 200 µL low-salt RNA binding buffer on a rotating platform at room temperature for 30 min. The reaction was passed through a pre-wetted nitrocellulose filter and washed with 1 mL binding buffer. The bound RNA was eluted from the filter with 200 µL elution buffer (7 M urea and 5 mM EDTA) at 95° C. for 5 min, followed by phenol/chloroform extraction and concentration with a Microcon YM-30 column (Millipore). The recovered RNA pool was reversed transcribed using the ThermoScript RT-PCR system (Invitrogen) and the cDNA was amplified by PCR for 15 cycles. After the amplified dsDNA pool was purified using a QIAquick Gel purification Kit, it was transcribed as described above and was used for the next round of selection.

After 11 and 12 rounds of SELEX, the resulting cDNAs were amplified by PCR cloned into the TOPO TA cloning vector pCR®2.1-TOPO (Invitrogen). Individual clones were identified by DNA sequencing.

Filter Binding Assays and Determination of Dissociation Constants.

Filter binding assays were used to detect the binding affinity of the individual aptamers. The RNA pool was treated with Calf Intestinal Phosphatase (CIP) to remove the initiating 5'-triphosphate and labeled with γ-$^{32}$P-ATP by T4 polynucleotide kinase and the end-labeled RNA pool (10 nM) was incubated with BAFF-R protein (100 nM) and a 10-fold molar excess of nonspecific competitor tRNA (100 nM) in the high-salt RNA binding buffer for 30 min. A 50 µL of binding reaction was separated by a pre-wet nitrocellulose filter. After the filter was washed with 2 mL binding buffer, the radioactivity retained on the filter was counted by a multi-purpose scintillation counter (Beckman Coulter).

Figure 13:
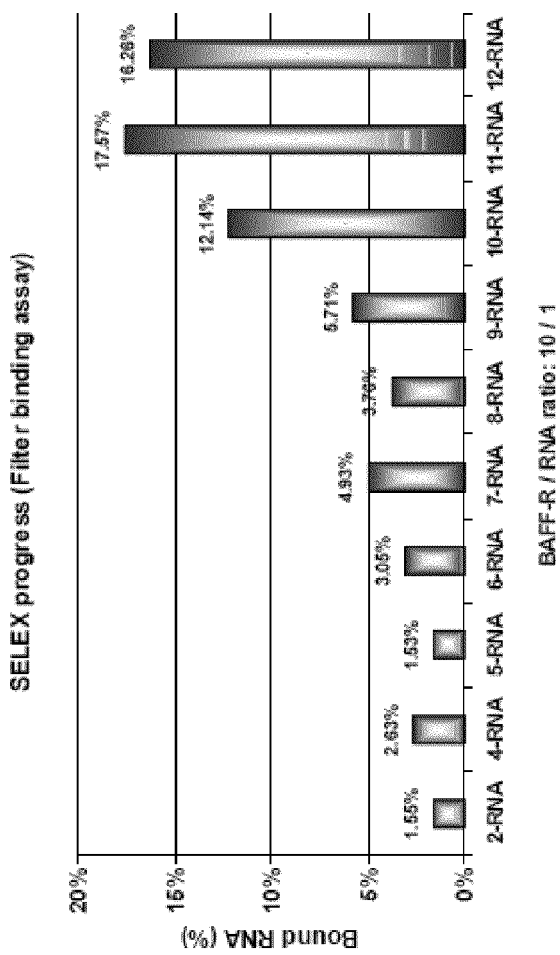
FIG. 13 is a bar graph illustrating the binding affinity for each round of RNA library selection (2-RNA to 12-RNA). RNA libraries were monitored by filter binding assay. At the 11$^{th}$ round of selection (11-RNA), the binding affinity of RNA library reached saturation.
Figure 45:
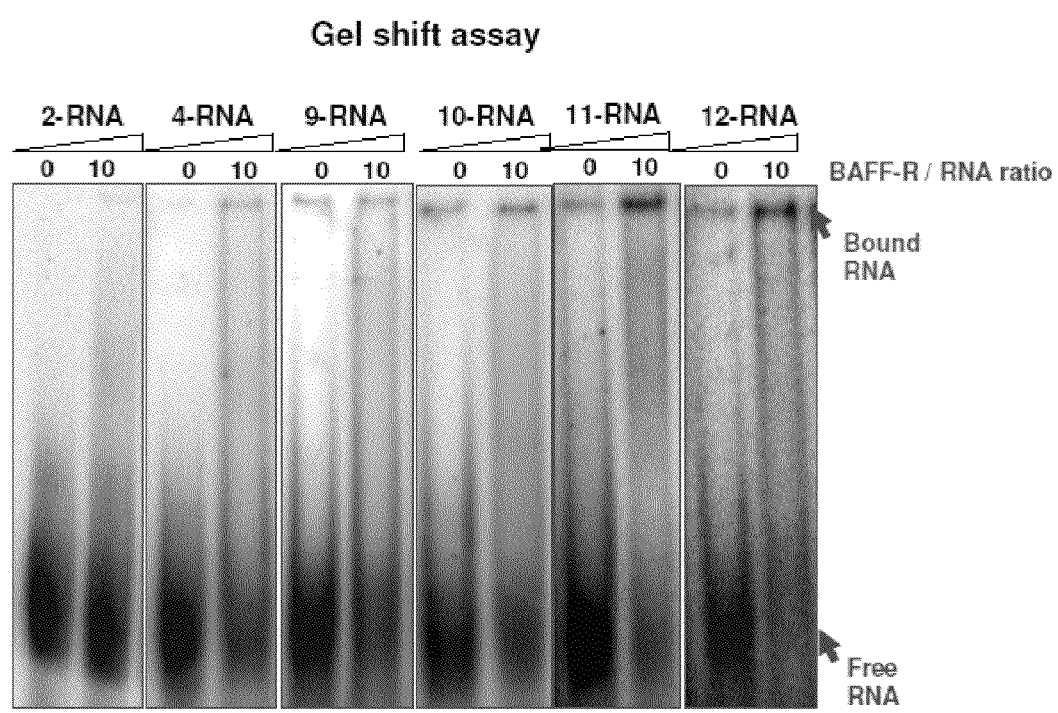
FIG. 45 is a gel shift assay illustrating binding activities of RNA pools generated by SELEX.

The binding affinity was obtained by calculating the percent of the RNA retained on the filter in the total input RNA pool. In order to determine dissociation constants, the BAFF-R protein was serially diluted to the desired concentrations (0~1280 nM). A constant amount of P$^{32}$ end-labeled RNA (2 nM) was used. The 50 µL binding reaction was performed as described above. The binding affinity was obtained by calculating the percent of the RNA retained on the filter in the input RNA. The dissociation constants were calculated using non-linear curve regression with a Graph Pad Prism. Selection and identification of RNA aptamers against human BAFF-R protein 2'-Fluoropyrimidine modified RNA aptamers that selectively bind to recombinant human BAFF-R protein were selected using an in vitro SELEX procedure as previously described[37], which selectively bind the human recombinant BAFF-R protein. Filter binding assays monitored the progress of selection after each SELEX cycle (FIG. 13). The binding affinity was evaluated as the percent of the RNA retained on the filter in the total RNA pool. When compared with the second round RNA pool (2-RNA) where 1.55% of the input RNAs was retained on the membrane, the 10$^{th}$ RNA library (10-RNA) had 12.14% of the input RNA bound. After the 11$^{th}$ round of selection, no further enrichment could be detected (FIG. 13), indicating that maximal binding of the RNA pool had been reached. The binding activities of the RNA pools were further confirmed by gel shift assays (FIG. 45). These results indicated that the RNA pool was successively enriched in aptamers with high binding specificity for the target protein.

Figure 15:
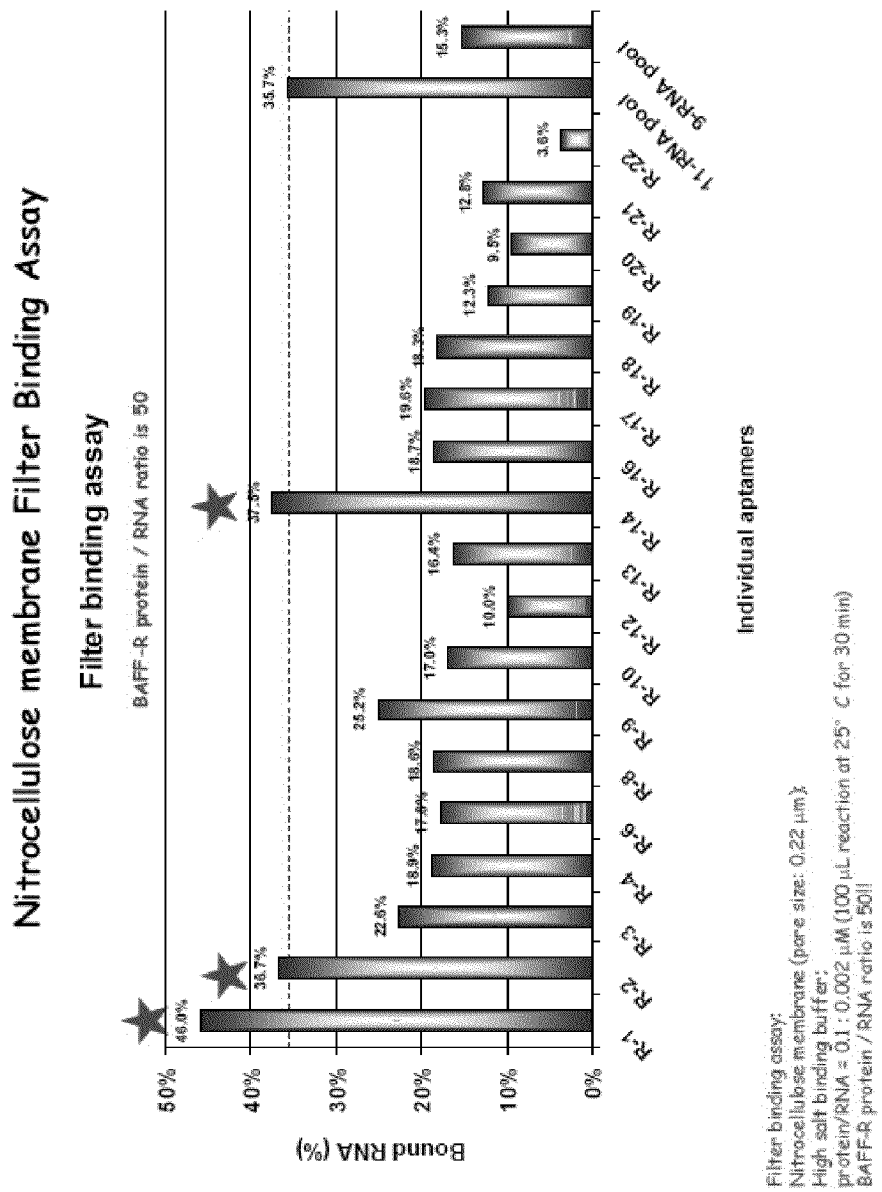
FIG. 15 is a bar graph illustrating the binding activity of selected individual aptamers against human BAFF-R protein using a nitrocellulose membrane filter binding assay. The 5'-end P$^{32}$ labeled individual aptamers were incubated with the BAFF-R protein. The binding reaction mixtures were analyzed by a filter binding assay. Aptamer R-1, R-2 and R-14 showed the best binding affinity with the target protein. The bound RNA (y-axis) is illustrated in %.

The highly enriched aptamer pools (11-RNA and 12-RNA) were cloned and sequenced. The individual clones were classified into eleven different groups based on the alignments of individual aptamer sequences (FIG. 14). About twenty-eight percent of the clones (Group 1 aptamers) included a conserved sequence, which is comprised of 7 nucleotides GAG-GCUC (SEQ ID NO:36), which are all underlined in FIG. 14. No common secondary structural motifs in these groups were found using secondary structure predictions based upon the RNA folding algorithms Mfold and 0 because of their relative abundance within their group. The filter binding assay confirmed the binding activity of the individual aptamers, wherein R-1, R-2 and R-14 showed the strongest binding affinities of above 36% comparable to SELEX round 11, while R-22 illustrated the lowest binding affinity (3.5%) (FIG. 15, stars).

Gel Shift Assays and Determination of Dissociation Constants.

The binding activities of the RNA pools were further confirmed by gel shift assays. Briefly, the BAFF-R protein was serially diluted to the desired concentrations (0-2560 nM). A constant amount of $P^{32}$ end-labeled RNA (2 nM) was used. The binding reaction was performed as described above. After incubation, 25 µL of binding reaction was loaded into a 5% non-denaturing polyacrylamide gel. Following electrophoresis the gel was exposed to a Phosphor image screen and the radioactivity was quantified using a Typhoon scanner. The dissociation constants were calculated using non-linear curve regression with a Graph Pad Prism. The results of the gel-shift assays indicated that the RNA pool was successively enriched in ligands with high binding specificity for the target protein. The dissociation constants ($K_d$) for selected aptamers (R-1, R-2 and R-14) with the target protein were calculated from a native gel mobility shift assay (FIG. 16A). Three of the aptamers showed good binding kinetics to gp120. The apparent $K_d$ values of R-1, R-2 and R-14 were about 47 nM, 95 nM and 96 nM (FIG. 16B), respectively.

Anti-BAFF-R Aptamer Specifically Binds and is Internalized by Cells Expressing BAFF-R Protein Jeko-1 cells (B-cell line) stably expressing BAFF-R proteins were used to test for binding and internalization of selected anti-BAFF-R aptamers (R-1 and R-14). As a negative control, CCRF-CEM cells (a human T-cell lymphoblast-like cell line) were used, which do not express BAFF-R. The anti-BAFF-R aptamers were labeled with Cy3 to follow their binding and uptake. Cy3-labeled BAFF-R aptamers were used to follow their binding and uptake.

Figure 17:
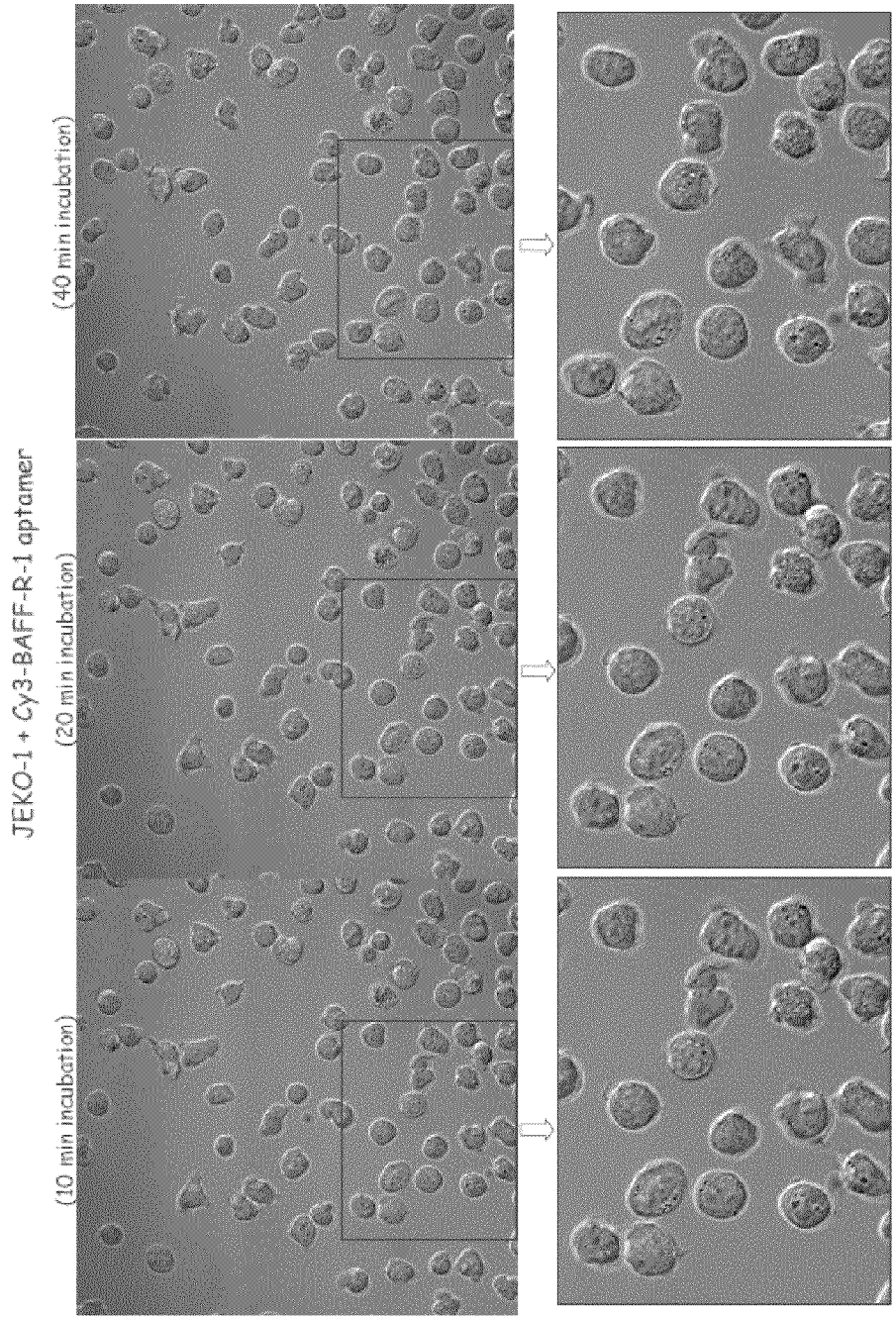
FIG. 17 is a series of confocal microscope pictures during an internalization analysis showing cell-type specific binding and uptake studies of aptamers. Cy3-labeled RNAs were tested for binding to Jeko-1 cells. Aptamer R-1 showed cell-type specific binding affinity. Cells were grown in 35 mm plates and incubated with a 60 nM concentration of Cy3-labeled aptamers in culture media for real-time live-cell-confocal microscopy analysis. The representative images were collected after 10, 20 and 40 minutes of incubation using 40× magnification.
Figure 18:
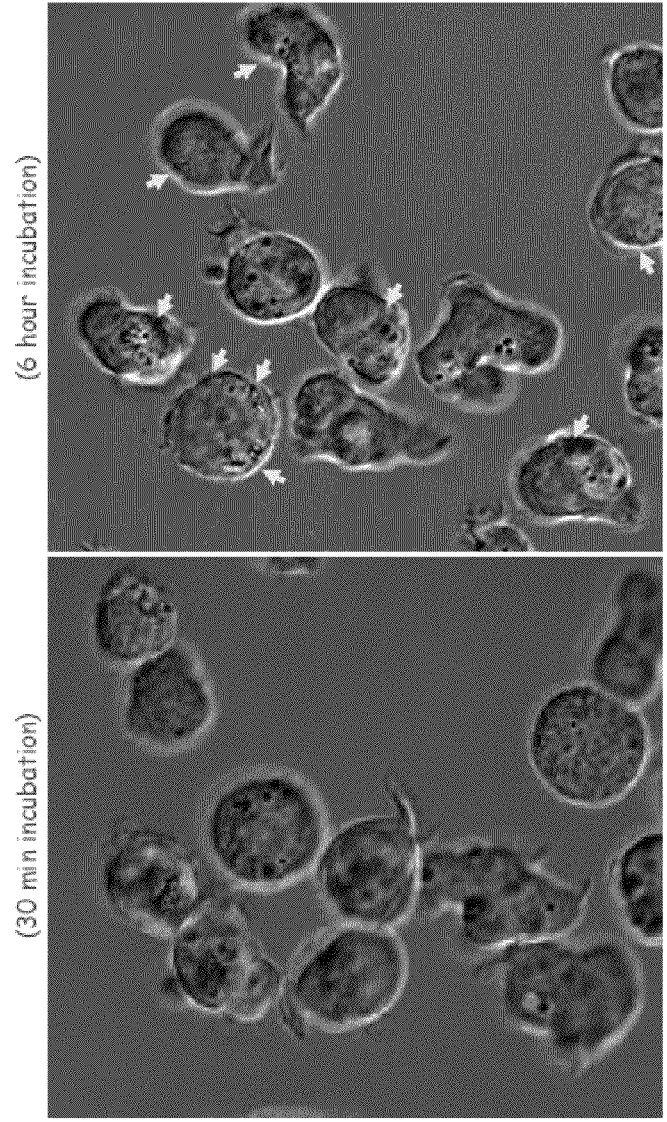
FIG. 18 is a series of confocal microscope pictures during an internalization analysis showing cell-type specific binding and uptake studies of aptamers. Cy3-labeled RNAs were tested for binding to Jeko-1 cells. Aptamer R-14 showed cell-type specific binding affinity. Cells were grown in 35 mm plates and incubated with a 60 nM concentration of Cy3-labeled aptamers in culture media for real-time live-cell-confocal microscopy analysis. The representative images were collected after 30 minutes and 6 hours of incubation using 40× magnification.
Figure 19:
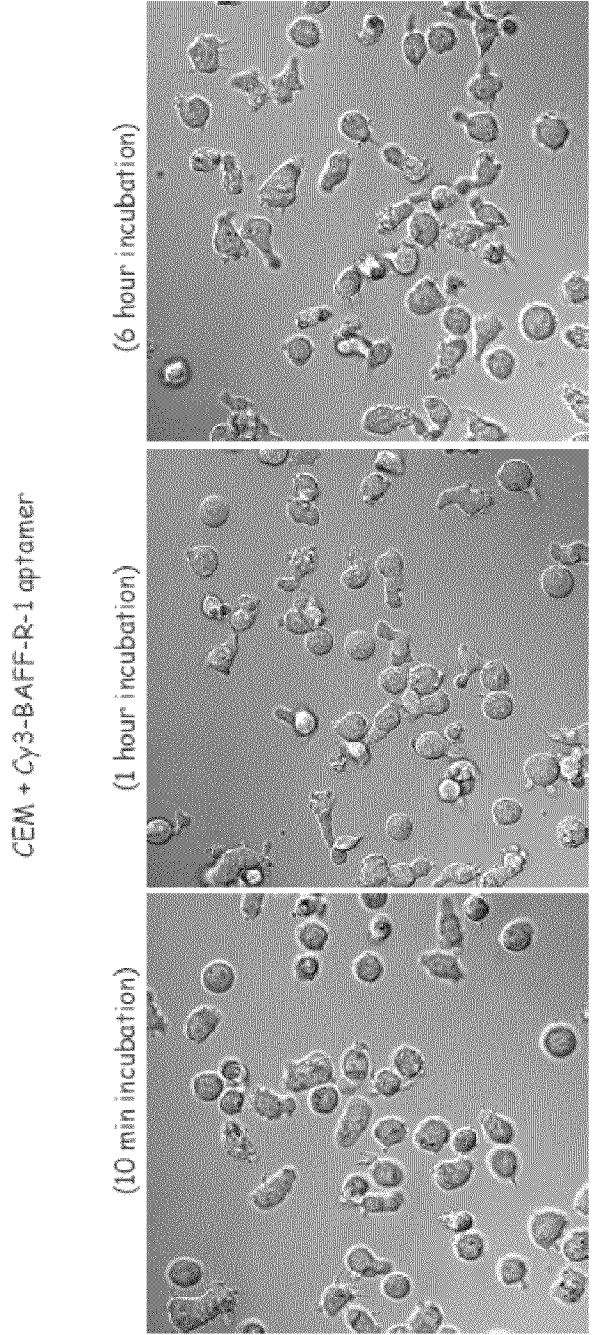
FIG. 19 is a series of confocal microscope pictures during an internalization analysis showing cell-type specific binding and uptake studies of aptamers. Cy3-labeled RNAs were tested for binding to OEM control cells. Aptamer R-1 showed cell-type specific binding affinity. Cells were grown in 35 mm plates and incubated with a 60 nM concentration of Cy3-labeled aptamers in culture media for real-time live-cell-confocal microscopy analysis. The representative images were collected after 10 minutes, 1 hour and 6 hours of incubation using 40× magnification.
Figure 20:
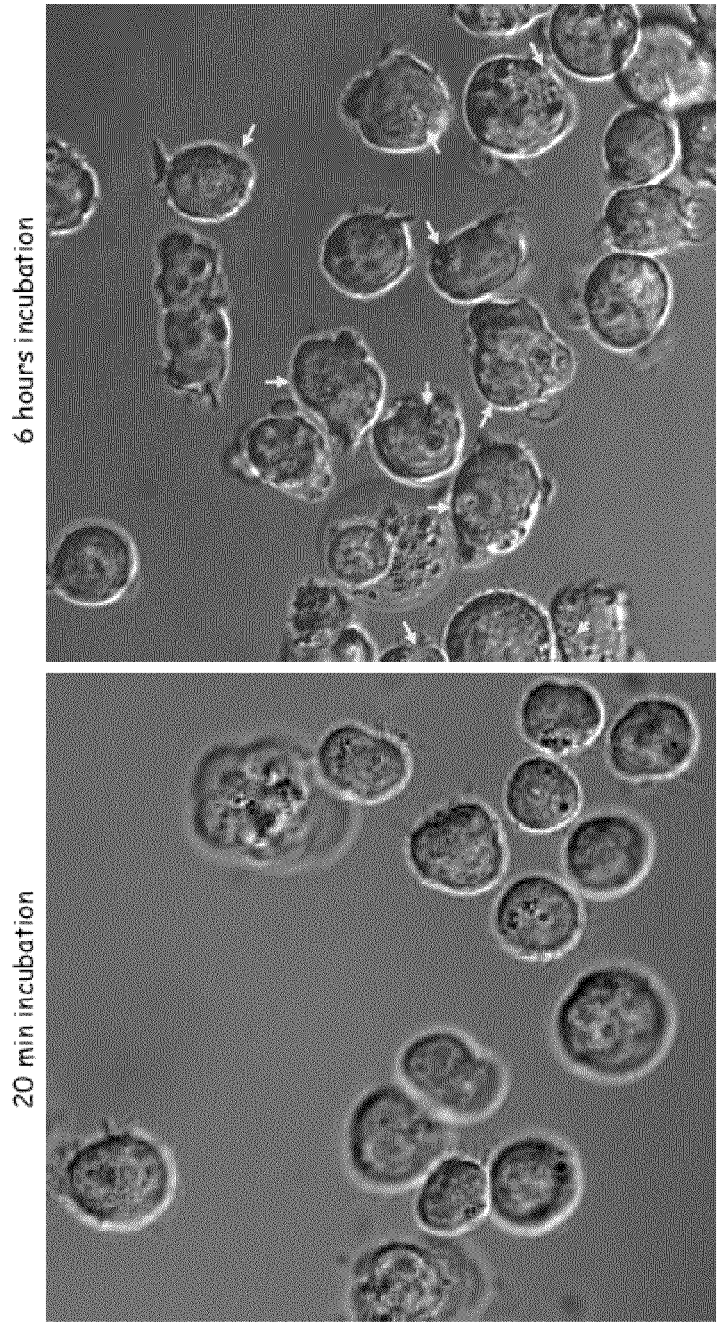
FIG. 20 is a series of confocal microscope pictures during a localization analysis. Jeko-1 cells were grown in 35 mm plates. Before incubation with 60 nM of Cy3-labeled A-1, cells were stained with Hoechst 33342 (nuclear dye for live cells) and then analyzed using real-time confocal microscopy.

To determine if the bound aptamers were internalized in the BAFF-R protein expressing cells, real-time live-cell Z-axis confocal microscopy was carried out in Jeko-1 cells incubated with the Cy3-labeled R-1 (FIG. 17) and R14 (FIG. 18) transcripts. After 20 minutes of incubation, the Cy3-labeled aptamers were selectively internalized within Jeko-1 cells, but not the CCRF-CEM control cells (FIG. 19). To visualize the nucleus, the cells were stained with the nuclear dye Hoechst 33342 before incubation with the Cy3 labeled-aptamer. FIG. 20 showed that the aptamer aggregated within the cytoplasm suggesting that the BAFF-R aptamers enter cells via receptor-mediated endocytosis.

Anti-BAFF-R Aptamers Compete with BAFF Ligand for the Binding of BAFF-R Protein and Block BAFF Ligand Mediated Cells Proliferation MTT and MTS Proliferation Assays.

Figure 21A:
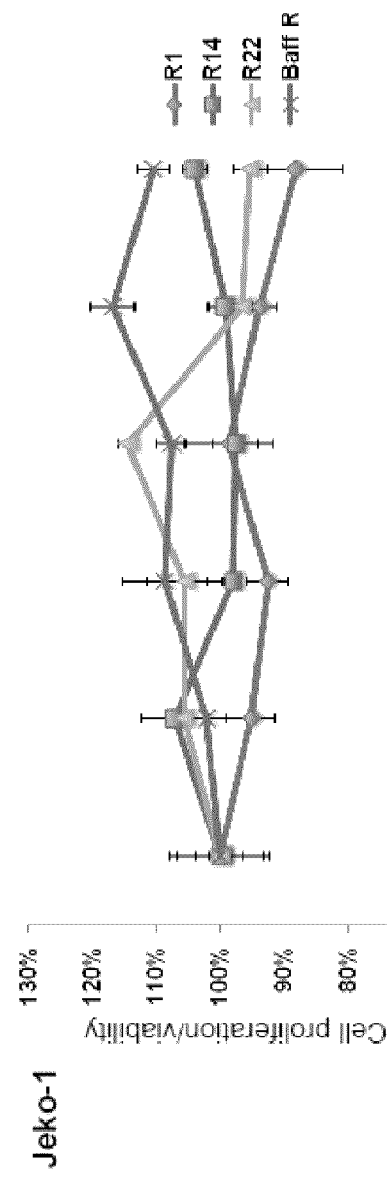
FIG. 21A is a graph illustrating cell proliferation in Jeko-1 cells detected by an MTT assay. The results showed that BAFF ligand triggered cell proliferation, but aptamers did not.
Figure 21B:
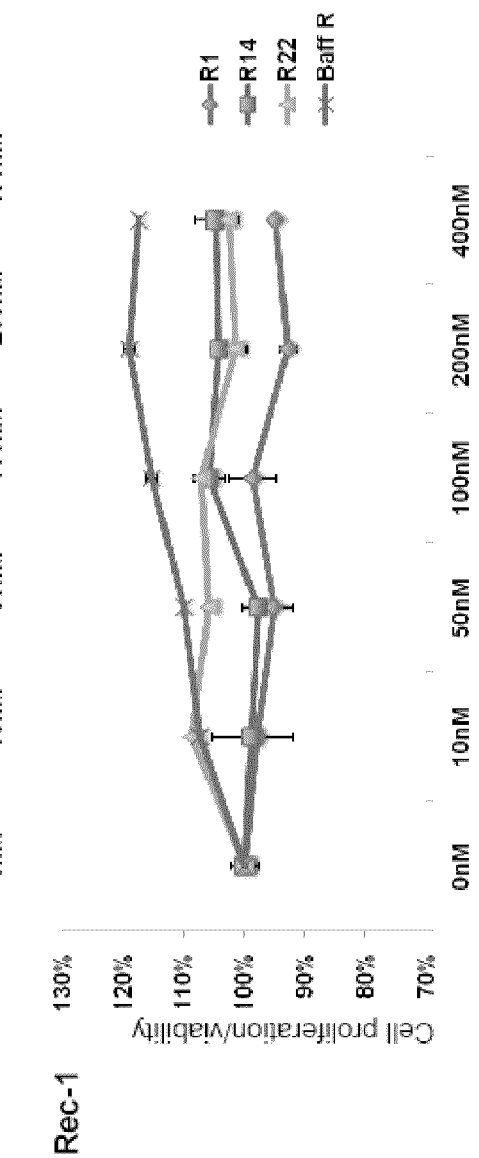
FIG. 21B is a graph illustrating cell proliferation in Rec-1 cells detected by an MTT assay. The results showed that BAFF ligand triggered cell proliferation, but aptamers did not.
Figure 38A:
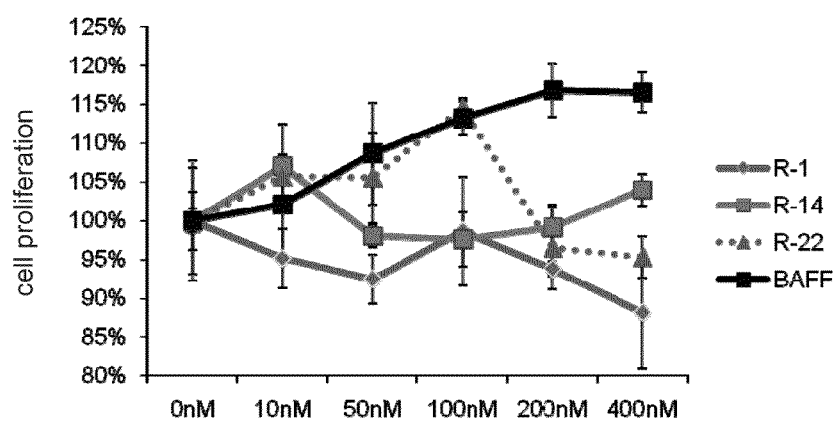
FIG. 38A shows the proliferation and competition of aptamer treated NHL cell lines. BAFF ligand can increase cell proliferation upon binding to BAFF-R on B-cells. MTS assays were performed to measure cell proliferation. Jeko-1 cells were treated with increasing amounts of BAFF-R aptamers R-1, R-14 and R-22 or BAFF. 48 h post incubation MTS assays were performed and cell proliferation was calculated in % and displayed.
Figure 38B:
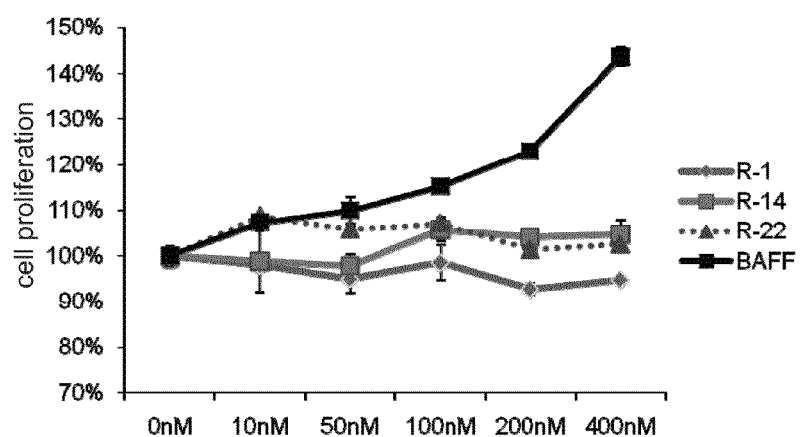
FIG. 38B shows the proliferation and competition of aptamer treated NHL cell lines. BAFF ligand can increase cell proliferation upon binding to BAFF-R on B-cells. MTS assays were performed to measure cell proliferation. Rec-1 cells were treated with increasing amounts of BAFF-R aptamers R-1, R-14 and R-22 or BAFF. 48 h post incubation MTS assays were performed and cell proliferation was calculated in % and displayed.
Figure 38C:
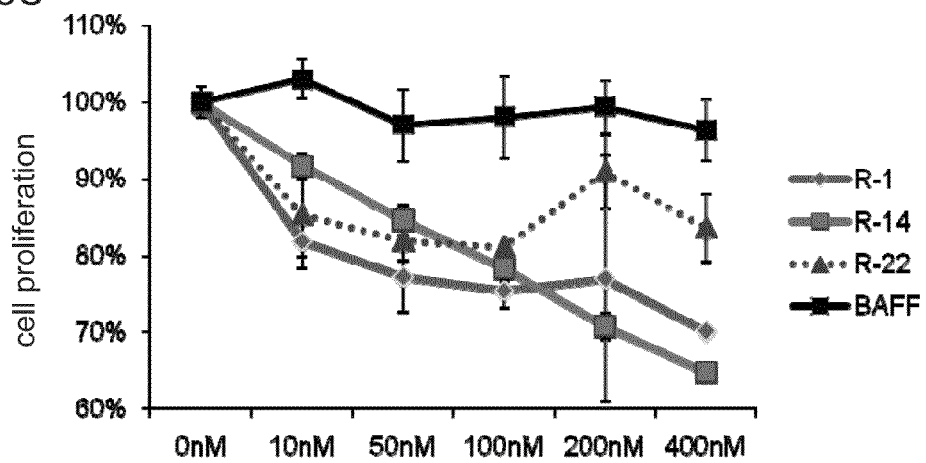
FIG. 38C shows the proliferation and competition of aptamer treated NHL cell lines. BAFF ligand can increase cell proliferation upon binding to BAFF-R on B-cells. MTS assays were performed to measure cell proliferation. Z138 cells were treated with increasing amounts of BAFF-R aptamers R-1, R-14 and R-22 or BAFF. 48 h post incubation MTS assays were performed and cell proliferation was calculated in % and displayed.
Figure 38D:
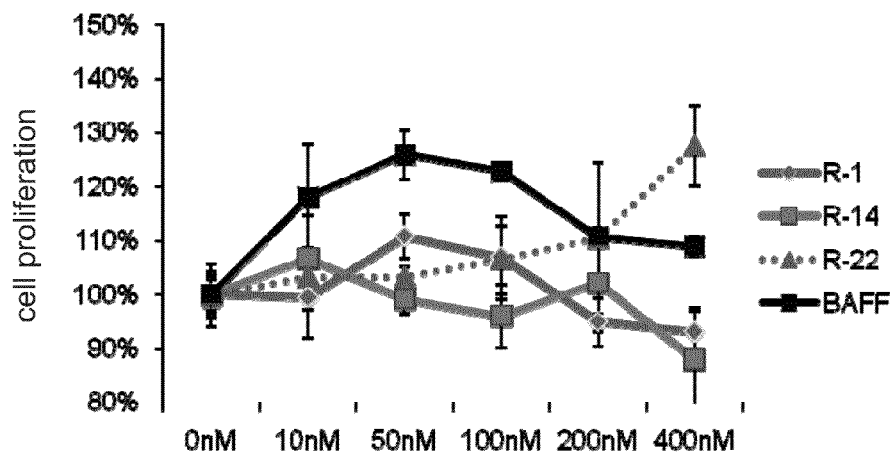
FIG. 38D shows the proliferation and competition of aptamer treated NHL cell lines. BAFF ligand can increase cell proliferation upon binding to BAFF-R on B-cells. MTS assays were performed to measure cell proliferation. Granta-519 cells were treated with increasing amounts of BAFF-R aptamers R-1, R-14 and R-22 or BAFF. 48 h post incubation MTS assays were performed and cell proliferation was calculated in % and displayed.

Previous studies have demonstrated that BAFF trimerizes and binds to the BAFF-R on the cell surface where it is internalized by receptor mediated endocytosis. The binding of BAFF to BAFF-R also enhances proliferation of cells and triggers severe autoimmune disease and cancer. MTT and MTS assays were performed to determine if the anti-BAFF-R aptamers would enhance cell proliferation in B-cell culture. In this assay, various B cells, such as Jeko-1, Z138, Rec-1 or Granta-519 cells were incubated with increasing concentrations of anti-BAFF-R aptamers (R-1, R-14 and R-22) or BAFF ligand. After 48 hours, the cells were subjected to MTS assays (FIG. 38A-D). BAFF ligand enhanced cell proliferation by 40% in Rec-1 cells with BAFF (FIG. 3B). In Jeko-1 and Granta-519 cells, the increase in proliferation with BAFF was less prevalent (FIG. 38A, 38D). In Z138 cells, BAFF ligand did not induce a proliferation increase (FIG. 38C). However, all cell lines treated with R-1 and R-14 reduced proliferation. Briefly, $6 \times 10^4$ Jeko-1, Z138, Granta 519 or and Rec-1 cells were seeded into 96 well plates. Cells were incubated with increasing concentrations (0, 50, 100, 200 and 400 nM) of BAFF-R aptamers (R-1, R-14, R-22), Chimeras (R-1-STAT3 27mer-OVH and R-1-STAT3 27-mer SWAP chimeras) or BAFF ligand (Prosbec-Tany TechnoGene Ltd.). 48 h post treatment, CellTiter 96® Non-Radioactive Cell Proliferation (Promega) assays (MTT assays) were performed according the manufacturer's protocol. Experiments were performed in triplicate. Results of the MTT assay are shown in FIG. 21. Although BAFF ligand triggered proliferation, the selected aptamers did not enhance proliferation.

MTS Competition Assay.

Figure 23:
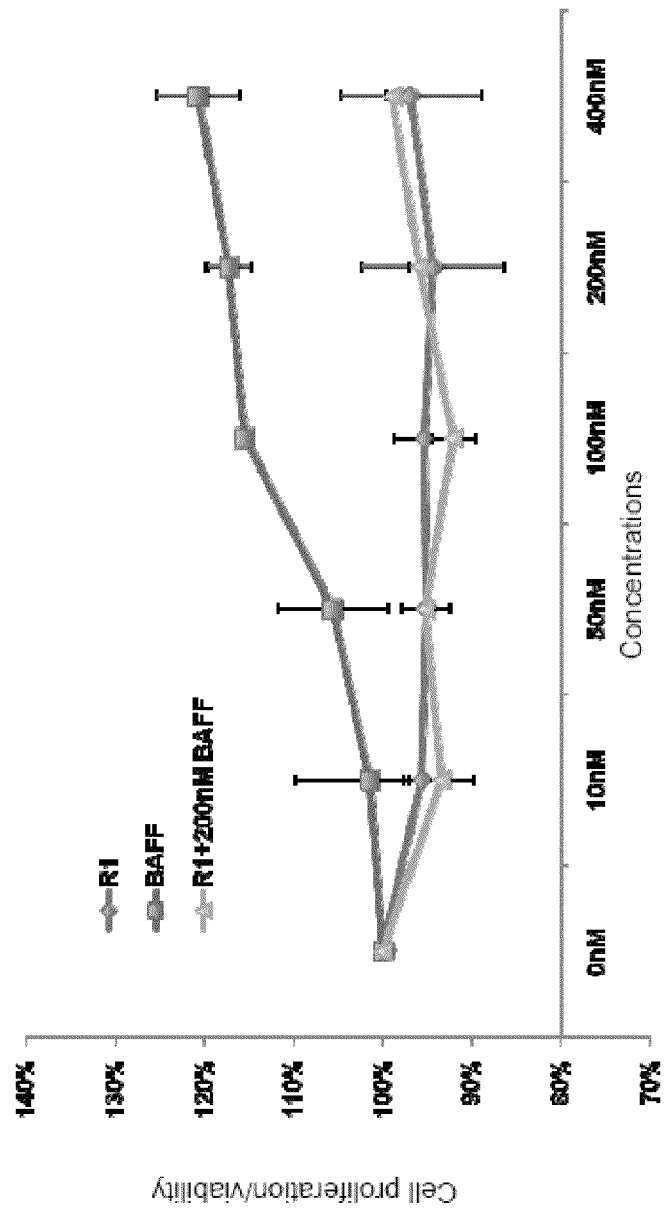
FIG. 23 is a graph illustrating cell proliferation that was detected by an MTS assay. Aptamer R-1 competed with BAFF ligand for binding to BAFF-R protein and blocked cell proliferation induced by BAFF ligand.

An MTS competition assay was also performed to determine whether the selected aptamers blocked BAFF ligand mediated cell proliferation. Briefly, $6 \times 10^4$ Rec-1 or Z138 cells were seeded into 96 well plates. Cells were incubated either with BAFF-R aptamers or BAFF-ligand in increasing concentrations (50, 100, 200 and 400 nM) as controls or with 200 nM BAFF 1-ligand (Prosbec-Tany TechnoGene Ltd.) and increasing concentrations of BAFF-R1 or BAFF-R14 aptamer (50, 100, 200, and 400 nM). The MTS was performed with CellTiter 96® Aqueous Non-Radioactive Cell Proliferation Assay (Promega) according to manufacturer's protocol. The results showed that these aptamers blocked cell proliferation mediated by BAFF ligand (FIG. 23), further confirming their ability to compete with BAFF-ligand for BAFF-R.

Figure 38E:
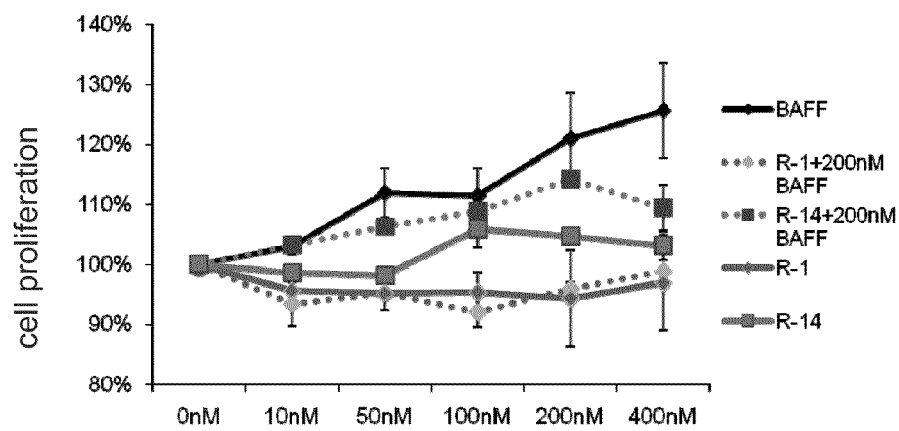
FIG. 38E shows the proliferation and competition of aptamer treated NHL cell lines. BAFF ligand can increase cell proliferation upon binding to BAFF-R on B-cells. MTS assays were performed to measure cell proliferation. Cell proliferation was measured by MTS in Rec-1 cells when treated with BAFF and increasing amounts of either R-1 or R-14 aptamers to investigate the potential of aptamers to block ligand-mediated proliferation.
Figure 38F:
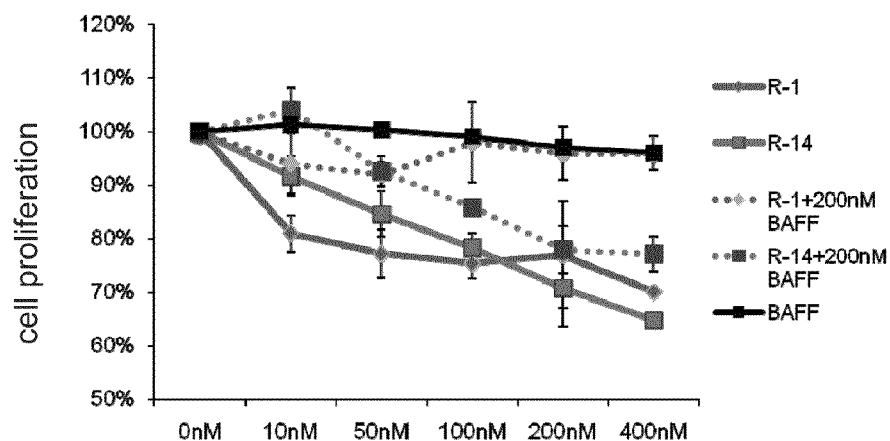
FIG. 38F shows the proliferation and competition of aptamer treated NHL cell lines. BAFF ligand can increase cell proliferation upon binding to BAFF-R on B-cells. MTS assays were performed to measure cell proliferation. Cell proliferation was measured by MTS in Z138 cells when treated with BAFF and increasing amounts of either R-1 or R-14 aptamers to investigate the potential of aptamers to block ligand-mediated proliferation.

In addition, an MTS competition assay was performed by treating Rec-1 cells (highest increase in proliferation with BAFF) and Z138 (lowest/no increase in proliferation) with a constant concentration of BAFF and increasing concentrations of R-1 and R-14 aptamers (FIG. 38E-F). R-1 aptamer efficiently blocked BAFF ligand-mediated proliferation in Rec-1 cells while R-14 was less potent (FIG. 38E). In Z138 cells, the opposed effect was observed (FIG. 38F). But no further increase in proliferation than BAFF ligand alone could be detected in both cell lines treated with BAFF-R aptamers.

Gel Shift Competition Assay.

Figure 22:
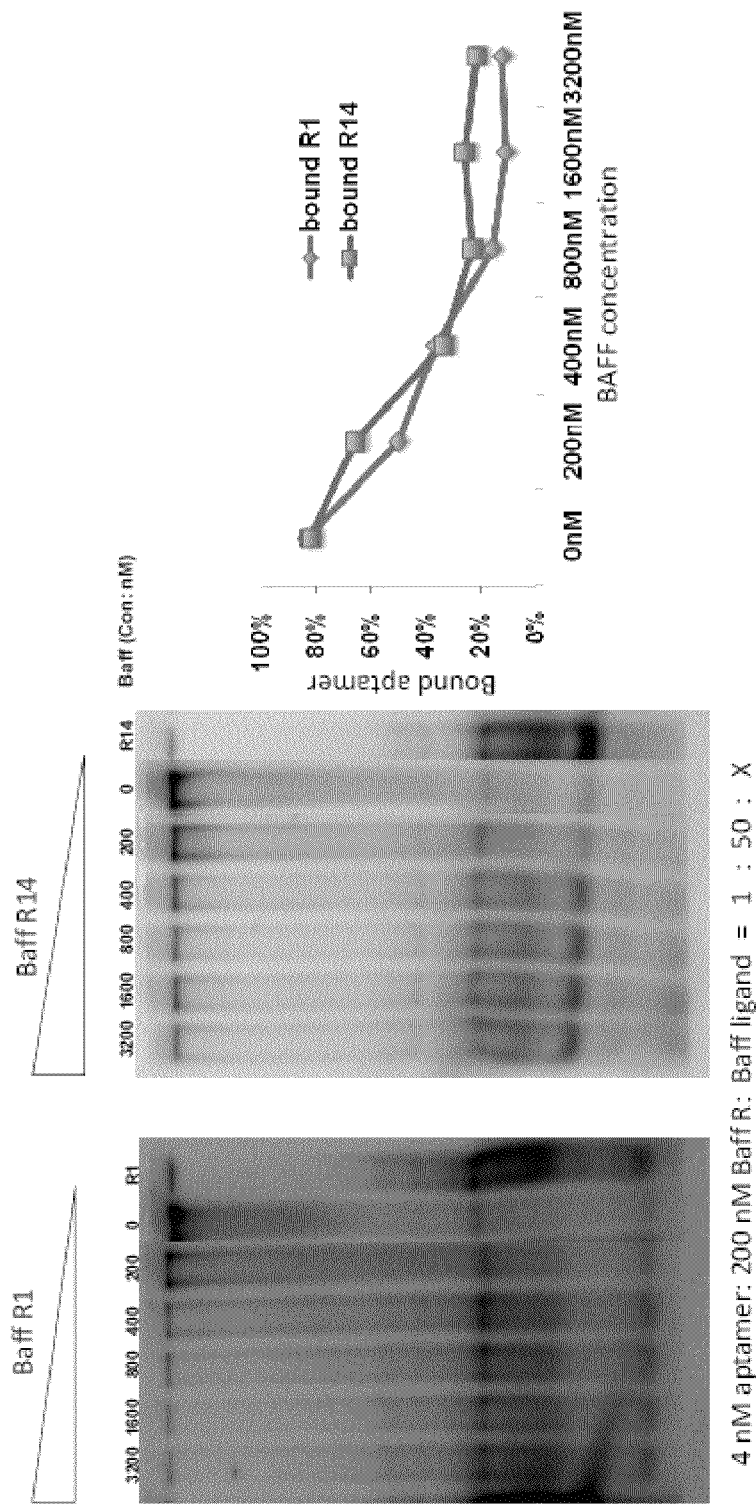
FIG. 22 illustrates a competition analysis of aptamers with BAFF ligand by a gel shift assay. The 4 nM of 5'-end P$^{32}$ labeled individual aptamers were incubated with 200 nM of the BAFF-R protein to form complexes. Then, increasing amounts of BAFF ligand were added. The reaction mixtures were analyzed by a gel shift assay (left). Aptamer competed with the BAFF ligand for binding to BAFF-R protein. The results were quantified in a graph (right).
Figure 46A:
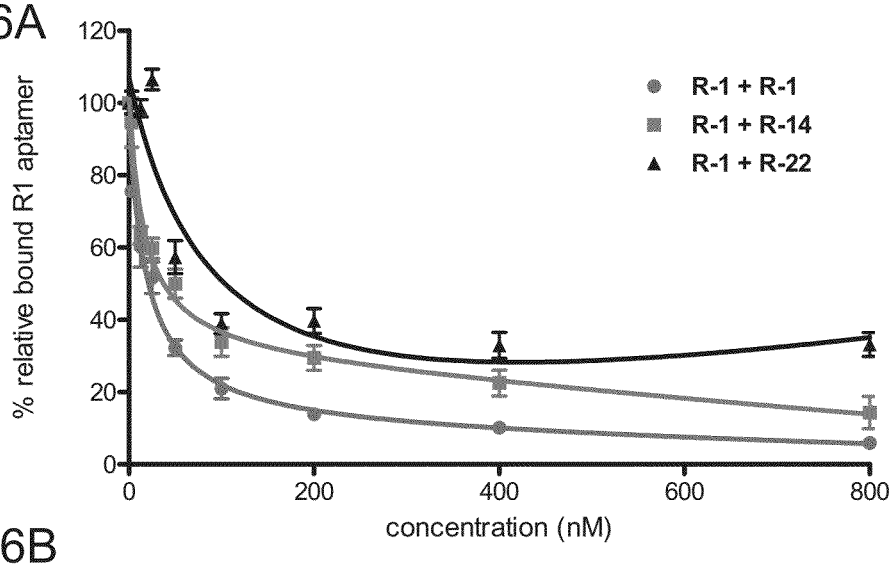
FIG. 46A is a graph illustrating the results of gel shift competition assays with cold aptamers for R-1 aptamers.
Figure 46B:
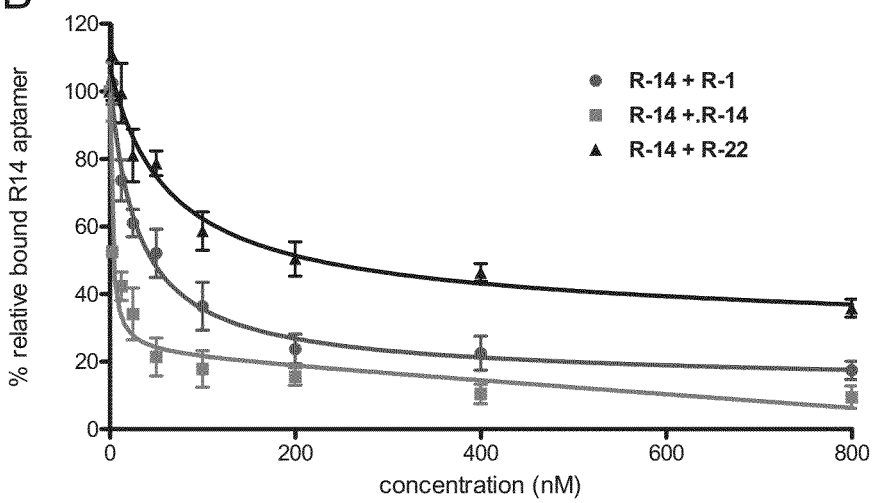
FIG. 46B is a graph illustrating the results of gel shift competition assays with cold aptamers for R14 aptamers.
Figure 46C:
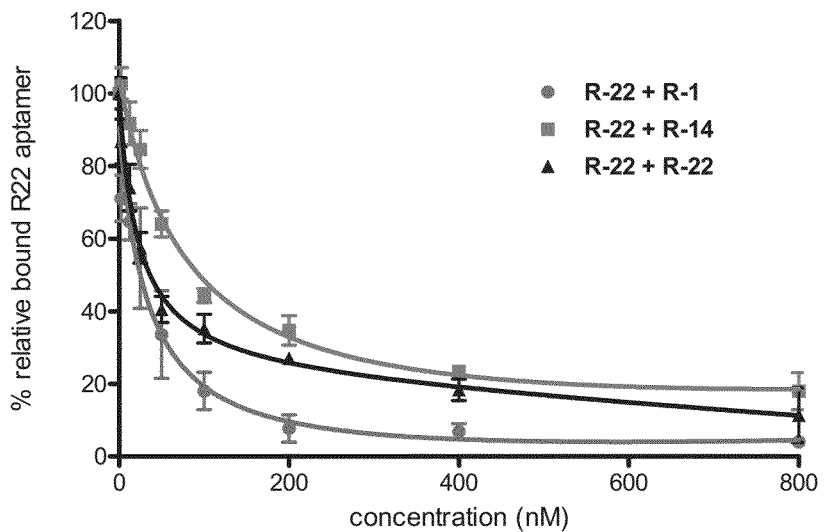
FIG. 46C is a graph illustrating the results of gel shift competition assays with cold aptamers for R-22 aptamers.

A gel shift assay showed that anti-BAFF-R aptamers are able to compete with BAFF ligand for BAFF-R protein (FIG. 22). For BAFF 1 ligand: 4 nM labeled aptamer BAFF-R-1 or BAFF-R-14 were incubated with a constant amount of BAFF-R protein (200 nM) in a 1:50 ratio and increasing concentration (200, 400, 800, 1600 nM) of BAFF 1 protein to assess the compatibility of the aptamers. The samples were incubated for 30 min at room temperature and loaded onto a 5% native Polyacrylamide gel. The gel was run at 4 degrees for approximately 2 h. It was then exposed to the phosphoimager for 3 h before measuring. For cold competitor: 4 nM labeled aptamer BAFF-R-1, BAFF-R-14 or BAFF-R-22 were incubated with a constant amount of BAFF-R protein (200 nM) in a 1:50 ratio and increasing concentration (2.5, 12.5, 25, 50, 100, 200, 400, 800 and 1600 nM) of cold competitor to assess the compatibility of our aptamers. The samples were incubated for 30 min at room temperature and assessed by phosphoimaging of a 5% native poly-acylamide gel. Experiments were performed in triplicate. In these gel shift competition assays with cold aptamers, the inhibition of all three aptamers was dose dependent, suggesting the binding affinity of aptamers is specific to their target protein (FIG. 46). The R-1 aptamer having the highest binding affinity had the strongest inhibition potential followed by the R-14 aptamer for all three tested aptamers (FIG. 46).

Figure 47:
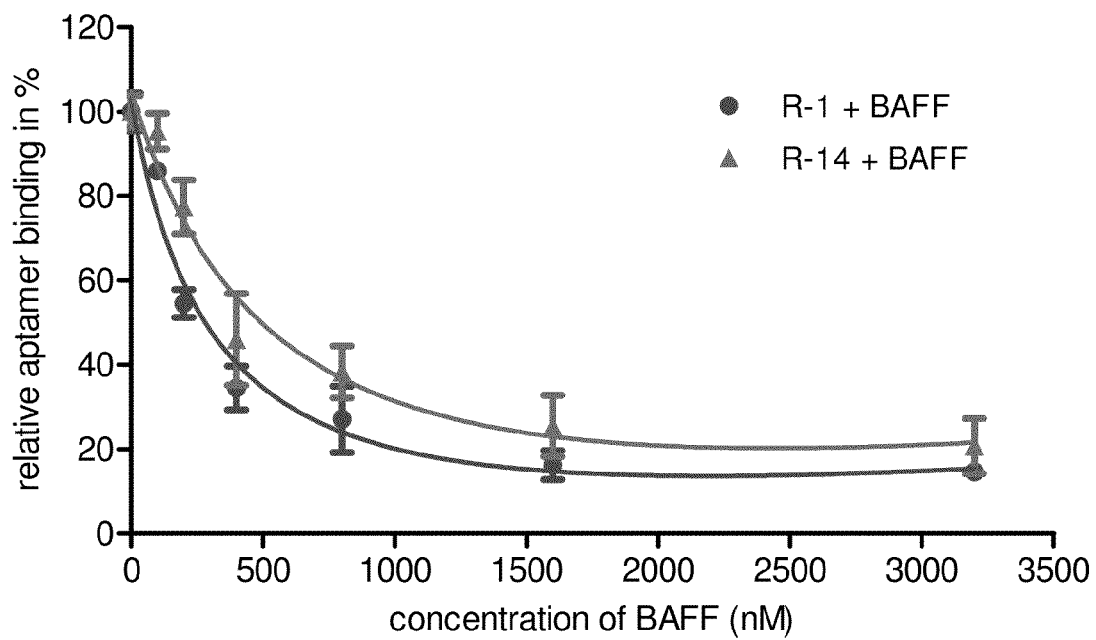
FIG. 47 is a graph illustrating the results of a competitive gel shift assay that shows that R-1 and R-14 aptamers are able to compete with BAFF ligand for BAFF-R protein in a dose-dependent manner.
Figure 50:
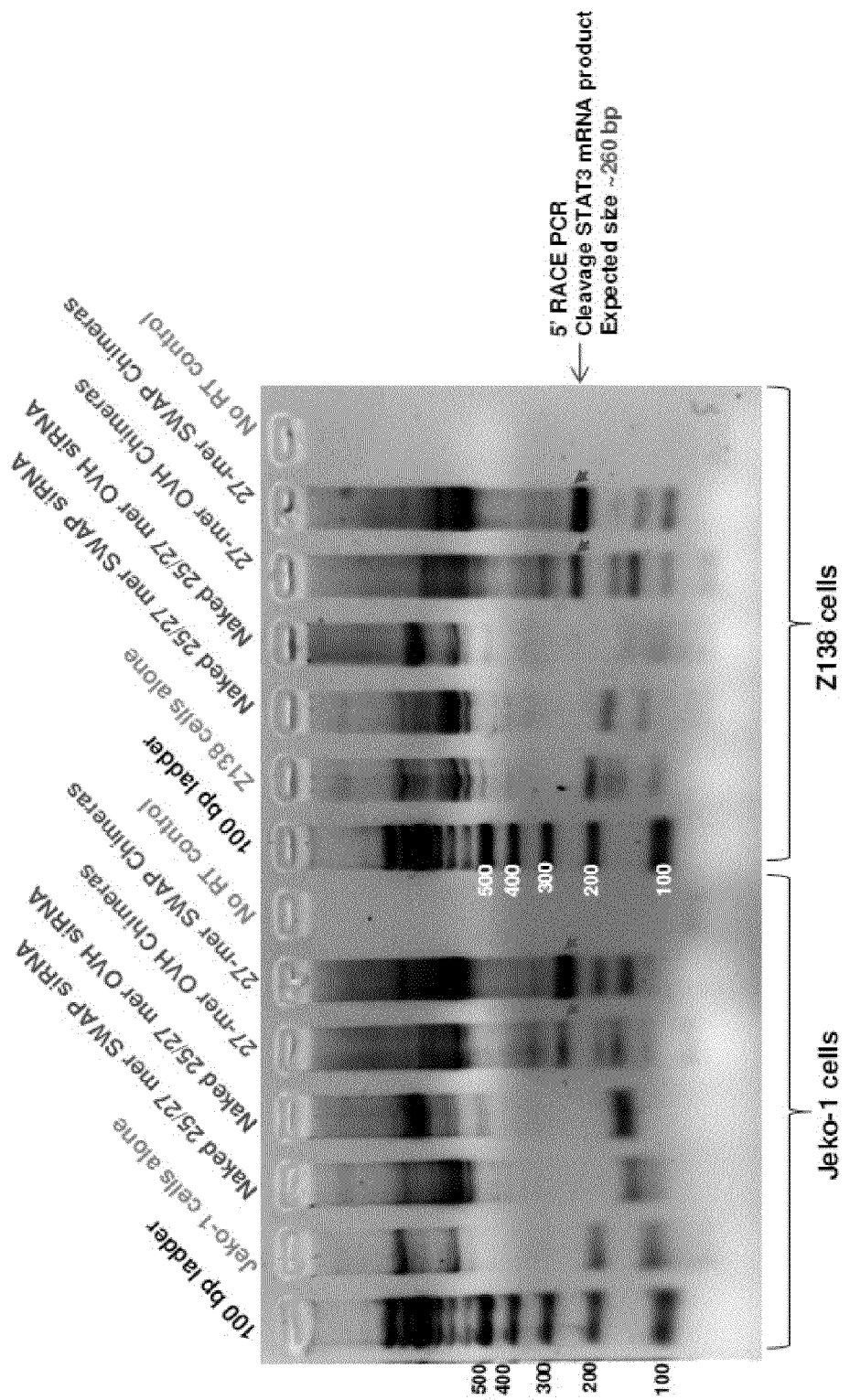
FIG. 50 illustrates the results of a modified 5'-RACE (rapid amplification of cDNA ends) PCR for the identified siRNA and chimeras in Jeko-1 and Z138 cells.

Further, a competitive gel shift assay was also performed to confirm the competition of aptamer and BAFF ligand to BAFF-R protein (FIG. 50). The results displayed that BAFF-R aptamers R-1 and R-14 were able to compete with BAFF ligand for BAFF-R protein (FIG. 47) in a dose dependent manner.

BAFF-R Aptamers do not Increase Survival of B-Cells by Up-Regulating Anti-Apoptotic Protein Bcl-2

Figure 39A:
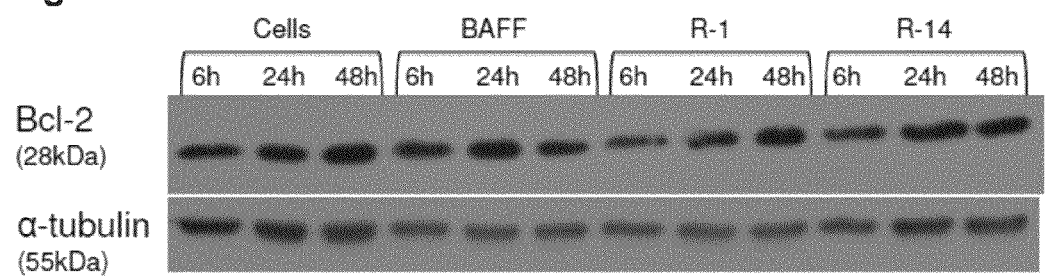
FIG. 39A shows Western Blot analysis for pro-survival Bcl-2 protein in aptamers treated Jeko-1 cells. Jeko-1 cells were treated with individual aptamers, BAFF or TNFα for 6, 24 and 48 hours. Protein was extracted and Immunoblotting illustrated Bcl-2 and α-tubulin levels. Results show Jeko-1 cells non treated (Cells), BAFF, R-1 or R-14 treated cells.
Figure 39B:
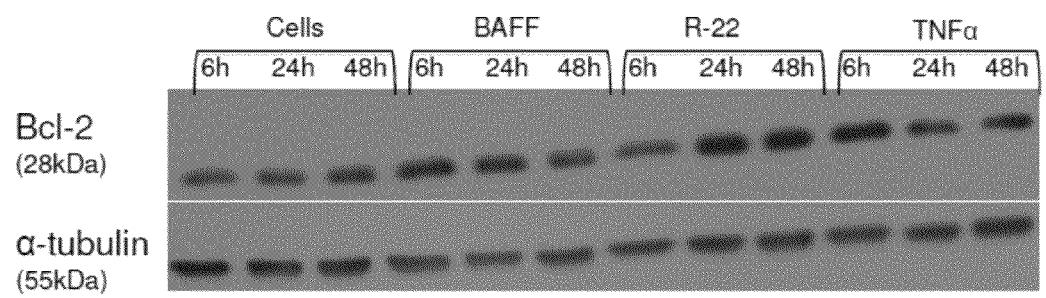
FIG. 39B shows Western Blot analysis for pro-survival Bcl-2 protein in aptamers treated Jeko-1 cells. Jeko-1 cells were treated with individual aptamers, BAFF or TNFα for 6, 24 and 48 hours. Protein was extracted and Immunoblotting illustrated Bcl-2 and α-tubulin levels. Results show non treated (Cells) Jeko-1 cells, BAFF, R-22 or TNF a treated cells.

It was previously shown that BAFF increases Bcl-2 levels in NHL via the NF-κB pathway, which leads to survival of the cancerous cells (He et al. 2004). Hence it was determined whether the BAFF-R aptamers described herein cause the same effect. Jeko-1 cells were incubated with BAFF-R aptamer, BAFF or TNF-α for different lengths of time. Protein was extracted and Western blot analysis was performed for Bcl-2 protein (FIG. 39). α-tubulin was used as loading control. While R-22 aptamer with the lowest binding affinity showed increase in Bcl-2 levels 24 h and 48 hours post treatment (FIG. 39B), aptamers R-1 and R-14 did not enhance Bcl-2 levels (FIG. 39A) as compared to control. Therefore, cancerous cells did not show increased survival as detected by BAFF-R aptamers R-1 and R-14 compared to BAFF-R ligand.

In summary, the aptamers generated and described herein are potential dual-function inhibitory agents for treatment of B-cell malignancies in which the BAFF-R is highly expressed on the cell surface. They can competitively inhibit BAFF 1 ligand mediated stimulation of proliferation and simultaneously deliver siRNAs that will down regulate transcripts encoding cell proliferation factors.

Example 4

Generation and Function of Aptamer-siRNA Chimeras

In addition to applicable materials and methods discussed above, the following additional materials and methods were used.

siRNAs.

siRNAs and antisense strand RNAs were purchased from Integrated DNA Technologies (IDT).

CCND1 siRNA Design 1:
D-1 Sense:
(SEQ ID NO: 1)
5'-CCACAGAUGUGAAGUUCAUUCCAA-3'

D-1 Antisense:
(SEQ ID NO: 2)
5'-UUGGAAAUGAACUUCACAUCUGUGGCA-3'

CCND1 siRNA Design 2:
D-2 Sense:
(SEQ ID NO: 3)
5'-UGUGCCACAGAUGUGAAGUUCAUUUCC-3'

D-2 Antisense:
(SEQ ID NO: 4)
5'-AAAUGAACUUCACAUCUGUGGCACA-3'

CCND1 siRNA Mutated Design 1: (the mutated bases are underlined)
Mutated D-1 Sense:
(SEQ ID NO: 5)
5'-CUCCAGAUUCCAAGCACAUUGUGAA-3'

Mutated D-1 Antisense:
(SEQ ID NO: 6)
5'-UUCACAAUGUGCUUGGAAUCUGGAGCA-3'

STAT3 siRNA
Sense:
(SEQ ID NO: 7)
5'-GAGAACGGAAGCUGCAGAAAGAUACGA-3'
Antisense:
(SEQ ID NO: 8)
3'-_CUCUUGCCUUCGACGUCUUUCUAUG-5'

Generation of Aptamer and Chimera RNAs by In Vitro Transcription.

Aptamer and chimera RNAs were prepared as previously described (Zhou et al. 2008). For the BAFF aptamers (SEQ ID NO: 7-9), the aptamer core sequences as shown in FIG. 14 are in bold. The sense strands of the chimeras are underlined. The uracil linker between the aptamer and siRNA portions is represented by one or more italic U.

BAFF-R-1 aptamer:
(SEQ ID NO: 9)
5'-GGGAGGACGAUGCGGGAGGCUCAACAAUGAUAGAGCCCGCAAUGUUGA UAGUUGUGCCCAGUCUGCAGACGACUCGCCCGA-3'

BAFF-R-14 aptamer:
(SEQ ID NO: 10)
5'-GGGAGGACGAUGCGGAUAACUAUUGUGCUAGAGGGCUUAUUUAUGUGA GCCGGUUGAUAGUUGCGCAGACGACUCGCCCGA-3'

BAFF-R-22 aptamer:
(SEQ ID NO: 11)
5'-GGGAGGACGAUGCGGAUCCUCCGAAGGUCGCGCCAACGUCACACAUUA AGCUUUUGUUCGUCUGCAGACGACUCGCCCGA-3'

Chimera BAFF-R-1-CCDN1 Design 1 (R-1 D-1) sense strand:
(SEQ ID NO: 37)
5'-GGGAGGACGAUGCGGGAGGCUCAACAAUGAUAGAGCCCGCAAUGUUGA UAGUUGUGCCCAGUCUGCAGACGACUCGCCCGA *UU* CCACAGAUGUGAAG UUCAUUUCCAA-3'

Chimera BAFF-R-14-CCDN1 Design 1 (R-14 D-1) sense strand:
(SEQ ID NO: 38)
5'-GGGAGGACGAUGCGGAUAACUAUUGUGCUAGAGGGCUUAUUUAUGUGA GCCGGUUGAUAGUUGCGCAGACGACUCGCCCGA *UU* CCACAGAUGUGAAG UUCAUUUCCAA-3'

-continued

```
Chimera BAFF-R-22-CCDN1 Design 1 (R-22 D-1) sense
strand:
                                      (SEQ ID NO: 39)
5'-GGAGGACGAUGCGGAUCCUCCGAAGGUCGCGCCAACGUCACACAUUAA

GCUUUUGUUCGUCUGCAGACGACUCGCCCGA UU CCACAGAUGUGAAGUU

CAUUUCCAA-3'

CCND1 Design 1 antisense strand:
                                      (SEQ ID NO: 40)
5'-UUGGAAAUGAACUUCACAUCUGUGGCA-3'

Chimera BAFF-R-1-CCDN1 Design 2 (R-1 D-2) sense
strand:
                                      (SEQ ID NO: 41)
5'-GGGAGGACGAUGCGGGAGGCUCAACAAUGAUAGAGCCCGCAAUGUUGA

UAGUUGUGCCCAGUCUGCAGACGACUCGCCCGA UU UGUGCCACAGAUGU

GAAGUUCAUUUCC-3'

Chimera BAFF-R-14-CCDN1 Design 2 (R-14 D-2) sense
strand:
                                      (SEQ ID NO: 42)
5'-GGGAGGACGAUGCGGAUAACUAUUGUGCUAGAGGGCUUAUUUAUGUGA

GCCGGUUGAUAGUUGCGCAGACGACUCGCCCGA UU UGUGCCACAGAUGU

GAAGUUCAUUUCC-3'

CCND1 Design 2 antisense stand:
                                      (SEQ ID NO: 43)
5'-AAAUGAACUUCACAUCUGUGGCACA-3'

Chimera BAFF-R-1-CCDN1 Mutated Design 1 (R-1
D-1-Mutated) sense strand:
                                      (SEQ ID NO: 44)
5'-GGGAGGACGAUGCGGGAGGCUCAACAAUGAUAGAGCCCGCAAUGUUGA

UAGUUGUGCCCAGUCUGCAGACGACUCGCCCGA UU CUCCAGAUUCCAAG

CACAUUGUGAA-3'

CCND 1 Mutated Design 1 antisense strand:
                                      (SEQ ID NO: 45)
5'-UUCACAAUGUGCUUGGAAUCUGGAGCA-3'

R-1-STAT3 27-mer OVH Chimera sense strand:
                                      (SEQ ID NO: 46)
5'-GGGAGGACGAUGCGGGAGGCUCAACAAUGAUAGAGCCCGCAAUGUUGA

UAGUUGUGCCCAGUCUGCAGACGACUCGCCCGA UUUUUUU

GAGAACGGAAGCUGCAGAAAGAUACGA-3'

STAT3 27-mer OVH Chimera antisense strand:
                                      (SEQ ID NO: 47)
3'-CUCUUGCCUUCGACGUCUUUCUAUG-5'

R-1-STAT3 27-mer SWAP Chimera antisense strand:
                                      (SEQ ID NO: 48)
5'-GGGAGGACGAUGCGGGAGGCUCAACAAUGAUAGAGCCCGCAAUGUUGA

UAGUUGUGCCCAGUCUGCAGACGACUCGCCCGA UUUUUUU

UCAGUCGUAUCUUUCUGCAGCUUCCGU-3'

STAT3 27-mer SWAP Chimera sense strand:
                                      (SEQ ID NO: 49)
3'-AGUCAGCAUAGAAAGACGUCGAAGG-5'
```

Design of Anti-BAFF-R Aptamer-CCND1 siRNA Chimera Delivery Systems that Bind and are Internalized by Cells Expressing BAFF-R Next, it was determined whether or not the selected aptamers could be used as cell-specific delivery vehicles for siRNA. The aptamer-siRNA chimeras (FIG. 24) were generated as previously described and a two nucleotide linker (UU) was inserted between the aptamer and the Dicer substrate anti-CCND1 siRNA portion to increase molecular flexibility. Aptamer R-22 with a low affinity was used as a negative control.

Figure 25:
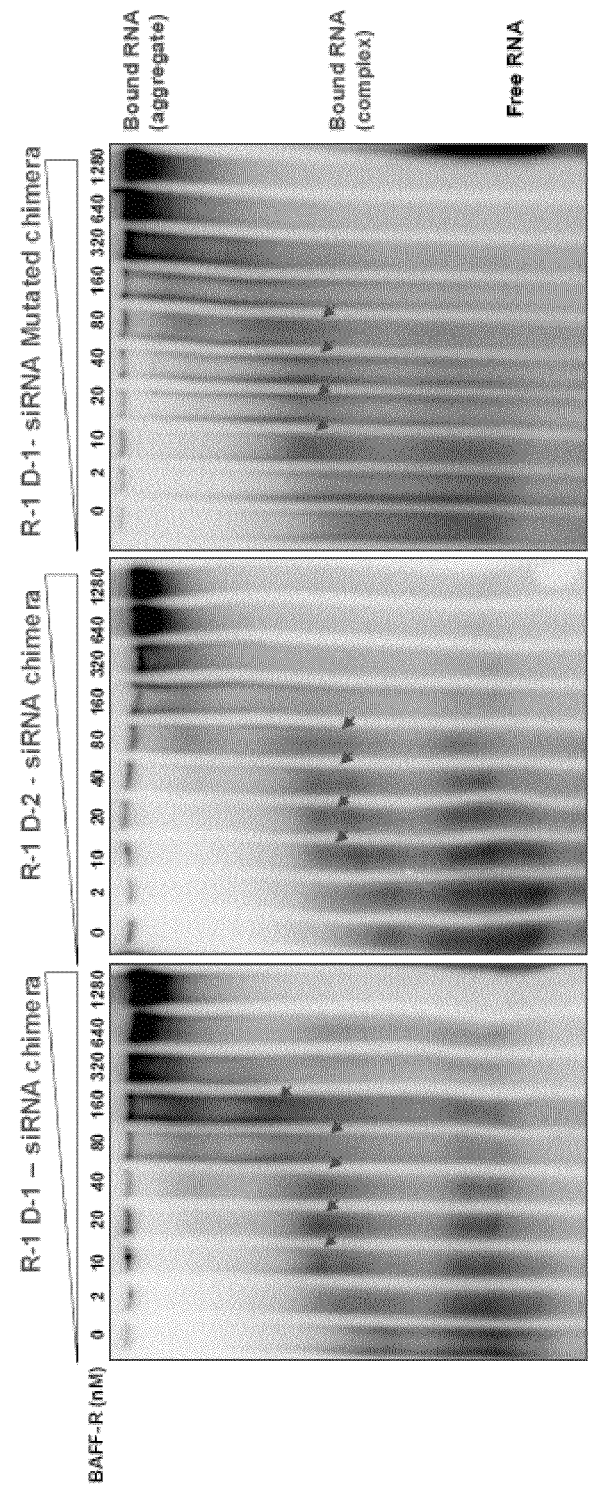
FIG. 25 is a series of representative gel shift assays to determine the binding activity of representative BAFF-R aptamer-siRNA chimeras (R-1 D-1, R-1 D-2, and R1-D-1-Mutated). Bound RNA (aggregate), bound RNA (complex) and free RNA are shown.
Figure 26:
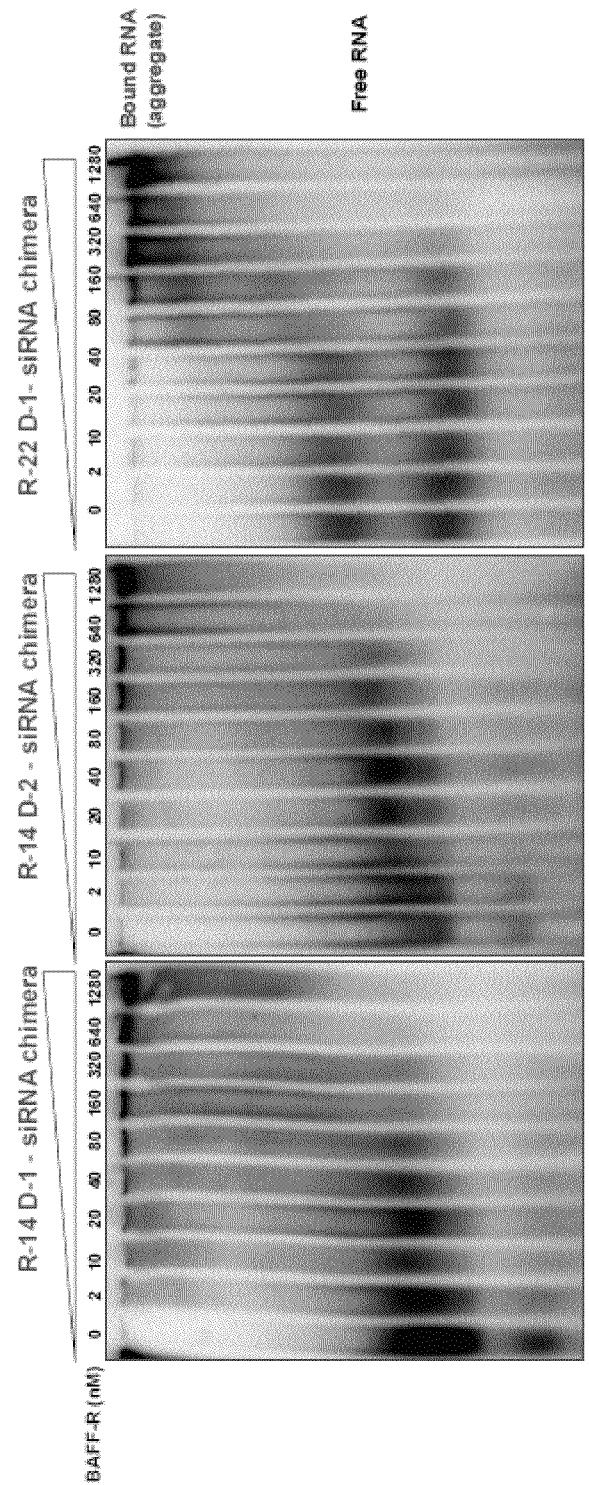
FIG. 26 is a series of representative gel shift assays to determine the binding activity of representative BAFF-R aptamer-siRNA chimeras (R-14 D-1, R-14 D-2 and R-22 D-1). Bound RNA (aggregate) and free RNA are shown.
Figure 27:
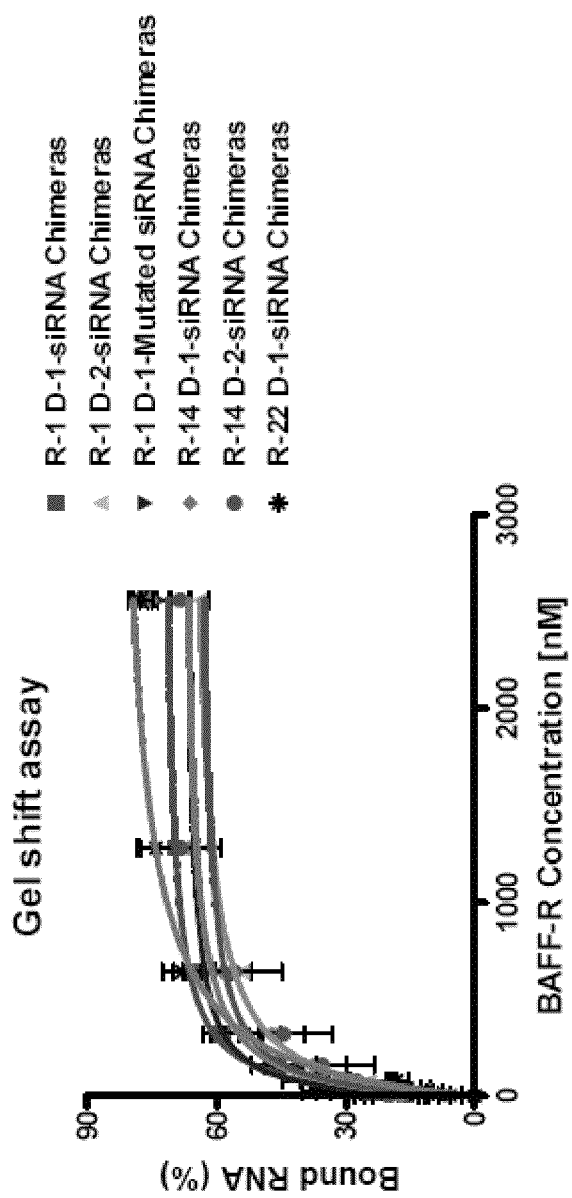
FIG. 27 is a binding curve from the results of the gel shift assays shown in FIGS. 25 and 26. The aptamer-siRNA chimeric RNAs that have comparable K$_d$ values as well as parental aptamers specifically bind the human BAFF-R protein. Data represent the average of three replicates.
Figure 28:
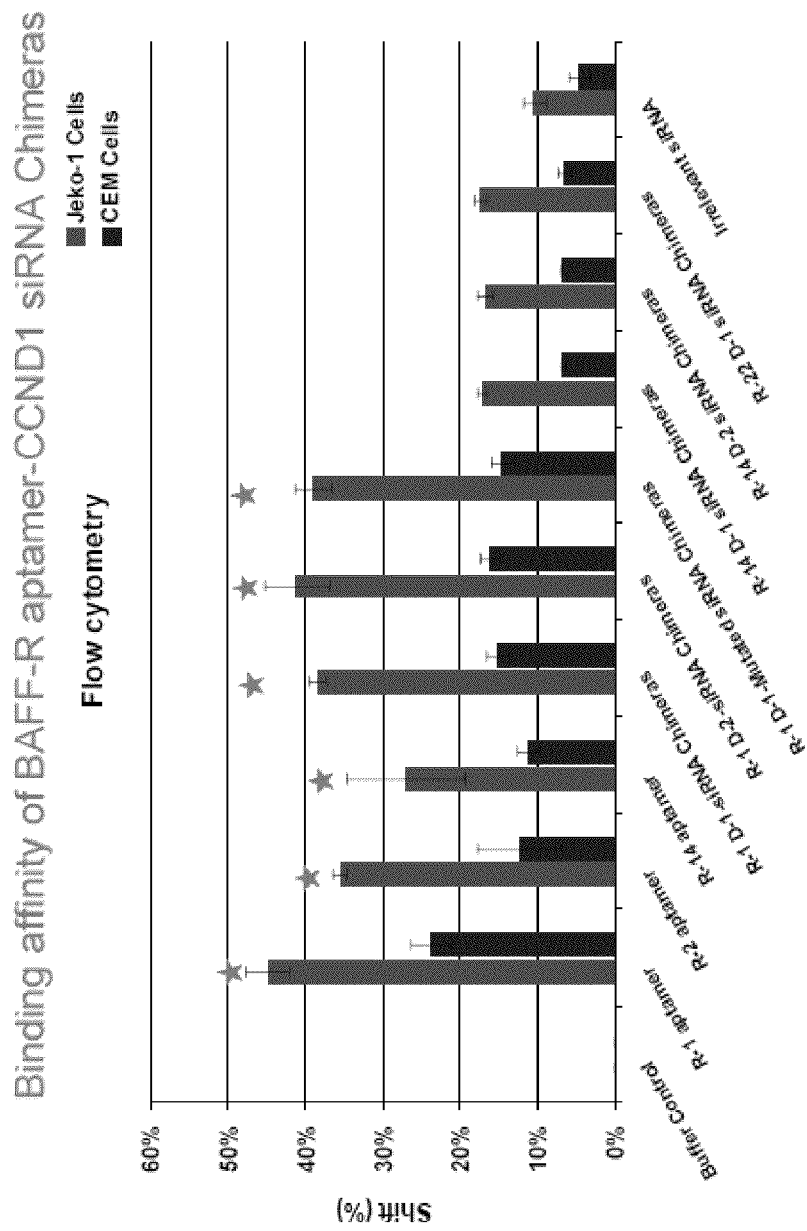
FIG. 28 is a bar graph illustrating cell-type specific binding studies of aptamers. Cy3-labeled RNAs were tested for binding to Jeko-1 cells and OEM control cells. Cell surface bindings of Cy3-labeled RNAs were assessed by flow cytometry. The selected aptamers showed cell-type specific binding affinity.
Figure 29:
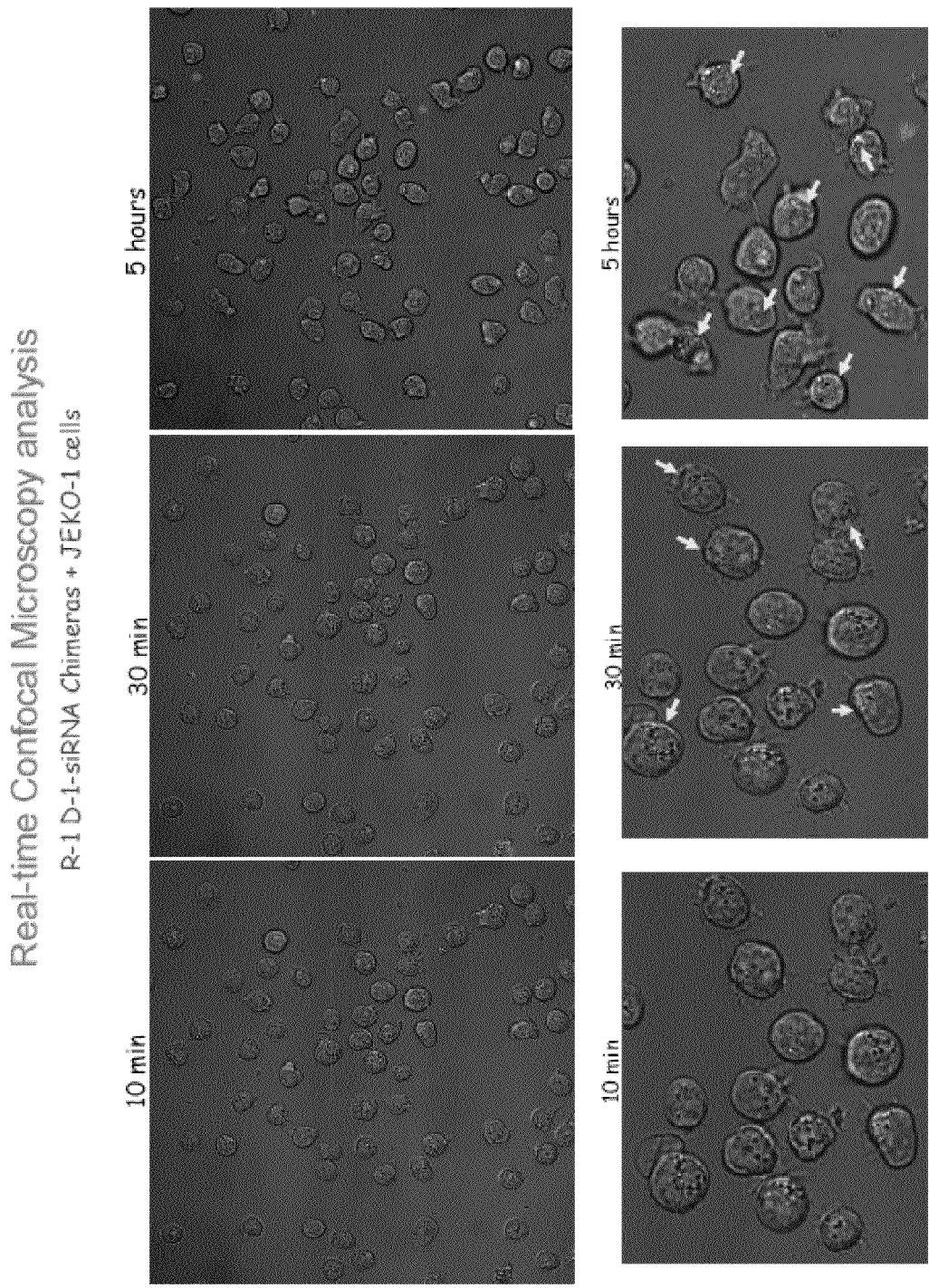
FIG. 29 is a series of confocal microscope pictures showing internalization and intracellular localization analyses for the R-1 D-1-siRNA chimeras. Jeko-1 cells were grown in 35 mm plates and incubated in culture medium with a 60 nM concentration of chimeras containing a 5'-Cy3-labeled sense strand for real-time live-cell confocal microscopy analysis as previously described. After overnight incubation, cells were stained with Hoechst 33342 (nuclear dye for live cells) and then analyzed by confocal microscopy. The chimeras showed cell-type specific binding affinity and localized in the cytoplasm of cells.
Figure 30:
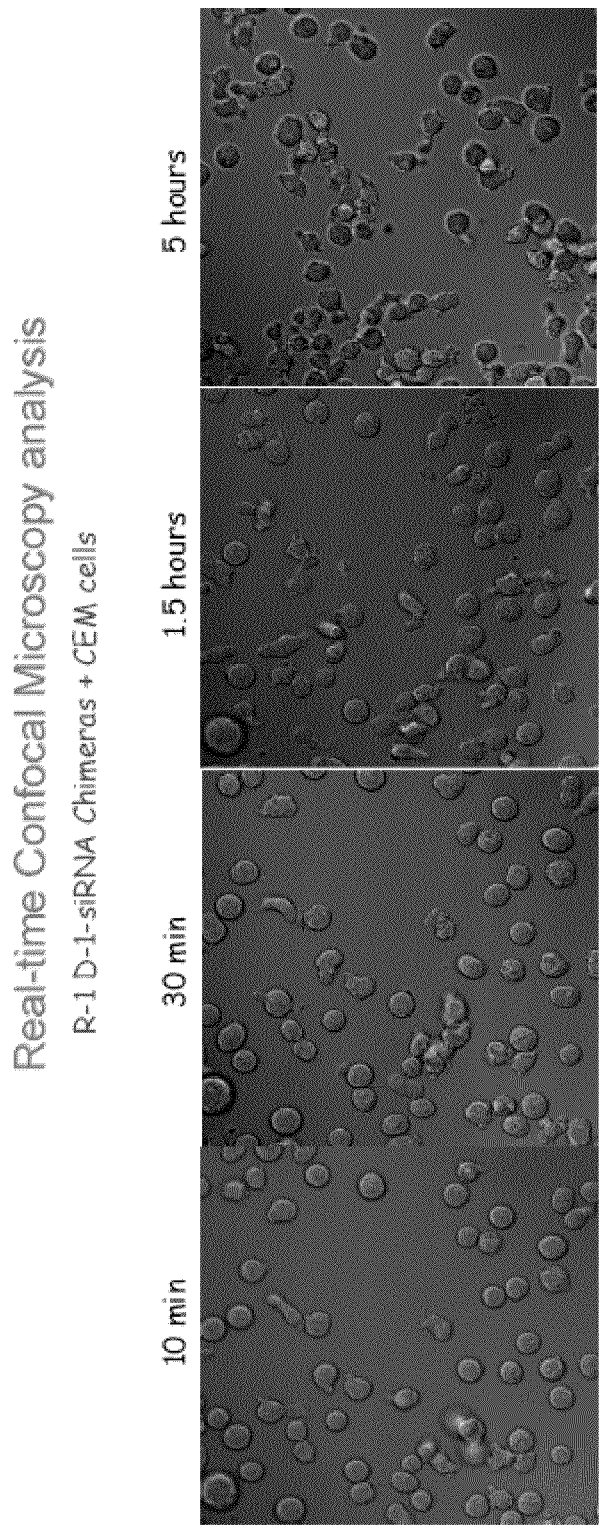
FIG. 30 is a series of confocal microscope pictures showing internalization and intracellular localization analyses for the R-1 D-1-siRNA chimeras. OEM control cells were grown in 35 mm plates and incubated in culture medium with a 60 nM concentration of chimeras containing a 5'-Cy3-labeled sense strand for real-time live-cell confocal microscopy analysis as previously described. After overnight incubation, cells were stained with Hoechst 33342 (nuclear dye for live cells) and then analyzed by confocal microscopy. The chimeras showed cell-type specific binding affinity and localized in the cytoplasm of cells.
Figure 31:
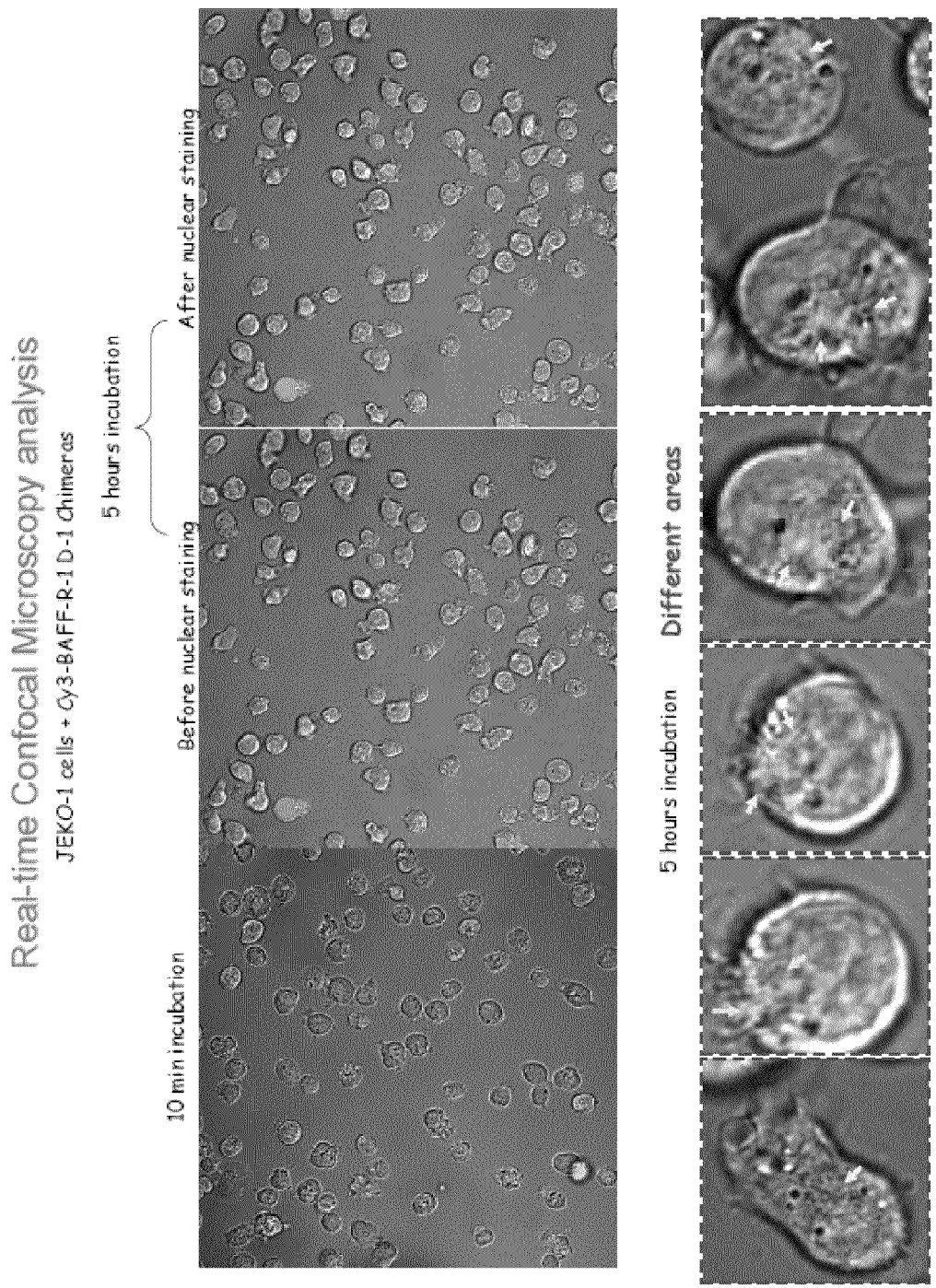
FIG. 31 is a series of confocal microscope pictures showing internalization and intracellular localization analyses for the R-1 D-1-siRNA chimeras. Jeko-1 cells were grown in 35 mm plates and incubated in culture medium with a 60 nM concentration of chimeras containing a 5'-Cy3-labeled sense strand for real-time live-cell confocal microscopy analysis as previously described. After overnight incubation, cells were stained with Hoechst 33342 (nuclear dye for live cells) and then analyzed by confocal microscopy. The chimeras did not show cell-type specific binding affinity and localized in the cytoplasm of cells.

The binding affinities of the chimeras for BAFF-R were assessed by using a gel shift assay (FIGS. 25 and 26), The apparent $K_d$ values of the R-1 D-1, R-1 D-2, R-1 D-1-Mutated, R-14 D-1, R-14 D-2, and R-22 D-1 chimeras were about 66 nM, 126 nM, 51 nM, 80 nM, 73 nM and 191 nM, respectively (FIG. 27). Binding affinities were also assessed by flow cytometry (FIG. 28). These data indicate that the chimeras maintain approximately the same binding affinities as the aptamers alone. To determine if the bound chimeras were internalized in the BAFF-R expressing cells, out Z-axis confocal microscopy was performed with Jeko-1 cells and OEM control cells incubated with Cy3-labeled transcripts as described above. The time-course images showed that Cy3-labeled chimera R-1 D-1-siRNA chimeras were successfully internalized into the cytoplasm of Jeko-1 cells (FIGS. 29 and 31). To visualize the nucleus, the cells were stained with the nuclear dye Hoechst 33342 after incubation with Cy3-RNA. No uptake of the chimera was observed with the OEM control cells (FIG. 30).

Figure 24:
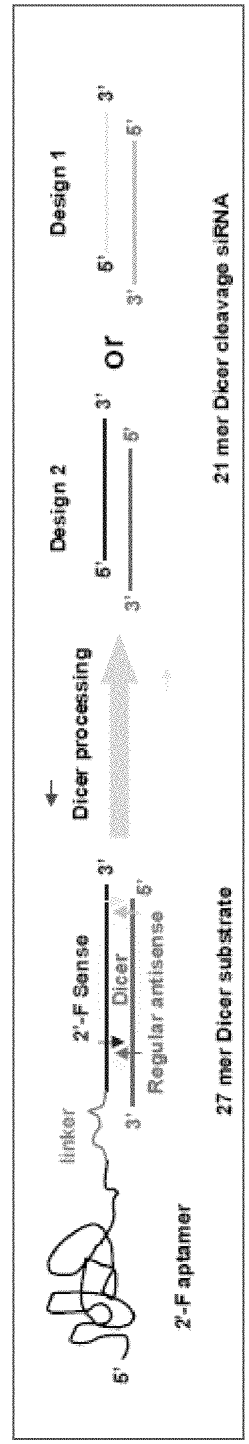
FIG. 24 is a schematic illustration of aptamer-siRNA chimeric RNAs according to some embodiments: the region of the anti-BAFF-R aptamer is responsible for binding to BAFF-R and the siRNA is targeting CCND1 gene. A linker (UU) between the aptamer and siRNA is indicated in green.

To determine whether or not human Dicer can process the siRNA portion of these chimeras, antisense strands were end-labeled with $\gamma$-$^{32}$P-ATP and subsequently used in formation of the chimeras (FIG. 24).

The antisense strands were end-labeled with T4 polynucleotide kinase and $\gamma$-$^{32}$P-ATP. Subsequently, corresponding antisense or sense strands were annealed with equimolar amounts of 5'-end-labeled sense strands in HBS buffer to form the chimeras. The experimental RNAs (1 pmol) were incubated at 37° C. for 40 min in the presence or in the absence of 1 U of human recombinant Dicer enzyme following the manufacturer's recommendations (Genlantis). Reactions were stopped by phenol/chloroform extraction and the resulting solutions were electrophoresed in a denaturing 20% polyacrylamide gel. The gels were subsequently exposed to X-ray film.

Figure 32:
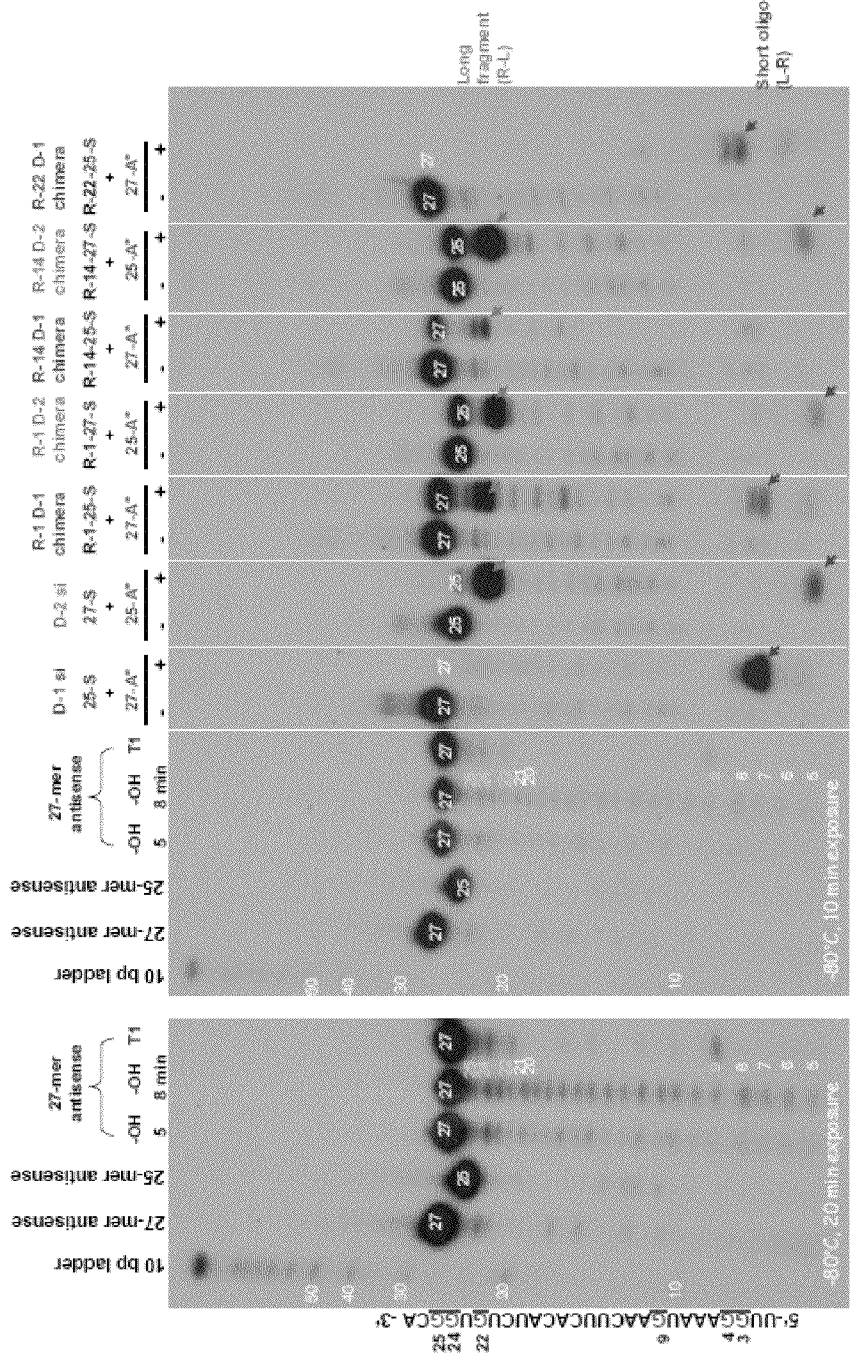
FIG. 32 is a gel illustrating the results of in vitro Dicer processing. Dicer cleavage of 5'-end $P^{32}$ antisense labeled RNAs. The RNA strands were annealed with equal molar equivalents of 5'-end $P^{32}$-labeled complementary RNA strands. The cleavage products or uncleaved, denatured strands were visualized following 20% denaturing polyacrylamide-gel electrophoresis. According to path of Dicer entry different cleavage products were observed.

The chimeras were incubated with recombinant human Dicer and the cleavage products were analyzed by denaturing gel electrophoresis. The size of the $P^{32}$ labeled cleavage product(s) indicates from which direction Dicer enters the siRNA and cleaves (FIG. 24 and FIG. 32). When chimera was incubated with the human Dicer and the $^{32}$P-label was placed on the 5' end of the antisense strand (FIG. 32), it was observed that the primary processing takes place via Dicer entry from the opposite side of the aptamer since the majority of the $^{32}$P-labelled resides in the 21-23 mer sized product as opposed to the shorter 6 nt product, which derives from Dicer entry on the aptamer side of the duplex.

Design of BAFF-R Aptamer-STAT3 siRNA Chimera Delivery Systems that Bind and are Internalized by Cells Expressing BAFF-R Further, it was determined whether the selected aptamers were effective as cell-specific delivery vehicles for an siRNA target gene. In this example, human STAT3 was selected as the siRNA target gene, however, any target gene may be used. The signal transducer and activator of transcription (STAT) proteins comprise of a family of transcription factors that regulate diverse cellular events such as differentiation, proliferation and cell survival (Yu et al. 2009). The transcriptional targets of STAT proteins play roles in cell cycle progression and also cell survival (Kortylewski & Yu 2008). Constitutively active STATs such as STAT3 and STAT5 contribute to a malignant phenotype in human cancer cell lines and primary tumors (Bowman et al. 2000).

Figure 40A:
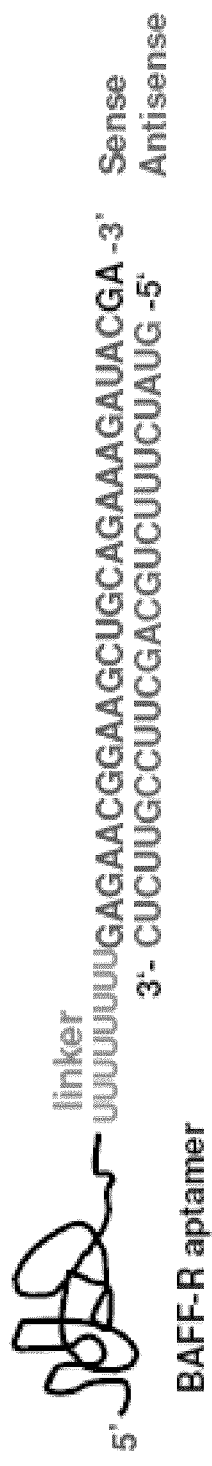
FIG. 40A shows the design and binding affinity of aptamer-siRNA chimera, R-1-STAT3 27-mer OVH. Schematic aptamer-siRNA chimeric RNAs: the region of the anti-BAFF-R aptamer is responsible for binding to BAFF-R and the siRNA is targeting STAT3 gene. A linker (8Us) between the aptamer and siRNA is indicated in green. Two versions, the R-1-STAT3 27-mer OVH chimera and the aptamer-siRNA chimera R-1-STAT3 27-mer SWAP shown in FIG. 40B, were designed, in which dsiRNA orientation is different.
Figure 40B:
FIG. 40B shows the design and binding affinity of aptamer-siRNA chimera, R-1-STAT3 27-mer SWAP. Schematic aptamer-siRNA chimeric RNAs: the region of the anti-BAFF-R aptamer is responsible for binding to BAFF-R and the siRNA is targeting STAT3 gene. A linker (8Us) between the aptamer and siRNA is indicated in green. Two versions, the R-1-STAT3 27-mer SWAP chimera and the aptamer-siRNA chimera R-1-STAT3 27-mer OVH shown in FIG. 40A, were designed, in which dsiRNA orientation is different.

Two aptamer-siRNA chimeras (R-1-STAT3 27-mer OVH chimera and 27-mer SWAP chimera) were designed and prepared as previously described (Zhou et al. 2009; Dassie et al. 2009) (FIGS. 40A and 40B). An eight nucleotide linker (8Us) was inserted between the aptamer portion and the Dicer substrate siRNA (dsiRNA) against human STAT3 portion to increase molecular flexibility for aptamer's correct folding and Dicer processing of dsiRNA, in case of sterical Dicer inhibition by the aptamer portion of the chimeras. A 2-nt 3' overhang was designed in the dsiRNA portion to facilitate Dicer binding and entry. The antisense and sense strand of the dsiRNA were swapped in the 27-mer SWAP design (FIG. 40B), which is expected to readily hand-off of antisense strand to the RISC (RNA-induced silencing complex).

Several B-cell lines were screened for their BAFF-R, STAT3 and Bcl-2 expression level by western blot analysis to select the most appropriate cell line for the function studies of BAFF-R aptamer-siRNA chimeras, such as binding, internalization, STAT3 knock-down and possible Bcl-2 increase assays.

RNA Extraction and qRT-PCR Analysis.

$2 \times 10^5$ cells (Jeko-1, Z138 and CCRF-CEM) were treated directly with the experimental RNA (400 nM). After 2 days of incubation, total RNA was isolated with STAT-60 (TEL-TEST, Friendswood, Tex.). Expression of the STAT3 coding RNA was analyzed by quantitative RT-PCR using 2x iQ SyberGreen Mastermix (BIO-RAD) and specific primer sets at a final concentration of 400 nM. Primers were as follows: STAT3 forward Primer: 5'-GCA GGA GGG CAG TTT GAG-3'; STAT3 reserved Primer: 5'-CGC CTC AGT CGT ATC TTT CTG-3'; GAPDH forward primer: 5'-CAT TGA CCT CAA CTA CAT G-3'; GAPDH reverse primer: 5'-TCT CCA TGG TGG TGA AGA C-3'.

RNA-Stat60 was used to extract total RNA according to the manufacturer's instructions (Tel-Test). Residual DNA was digested using the DNA-free kit per the manufacturer's instructions (Ambion, CA). cDNA was produced using 2 μg of total RNA Moloney murine leukemia virus reverse transcriptase and random primers in a 154 reaction according to the manufacturer's instructions (Invitrogen, CA). GAPDH expression was used for normalization of the qPCR data.

Protein Extraction and Western Blot Analysis.

Protein extraction was performed 48 h post incubation, by adding 50~100 μL M-Per® Mammalian Protein Extraction Reagent lysis buffer (Thermo Scientific), containing Complete, Mini Protease Inhibitor Cocktail (Roche). Samples were frozen in an ethanol bath for 30 seconds and thawed for 30 seconds in a 37° C. water bath, repeating freeze thaw cycles twice followed by centrifugation at 13,000 rpm for 10 min at 4° C. The concentration of the samples was determined with the Bio-Rad Protein Assay according to manufacturer's instructions. Samples were stored at −80° C. until assay.

Proteins (25 μg) were separated on a 12% SDS-PAGE. Immunoblotting identified Bcl-2, STAT3 and alpha-tubulin proteins. Bcl-2 (28 kDa) was detected with mouse anti-Bcl-2 IgG from Santa Cruz Biotechnology, STAT3 (89 kDa) with rabbit anti-STAT3 IgG from Santa Cruz Biotechnology and the loading control α-tubulin (55 kDa) was detected with mouse anti-alpha tubulin IgG from Sigma-Aldrich and goat anti-mouse IgG-HRP or anti-rabbit-IgG-HRP (Santa Cruz Biotechnology) as secondary antibodies.

Figure 48:
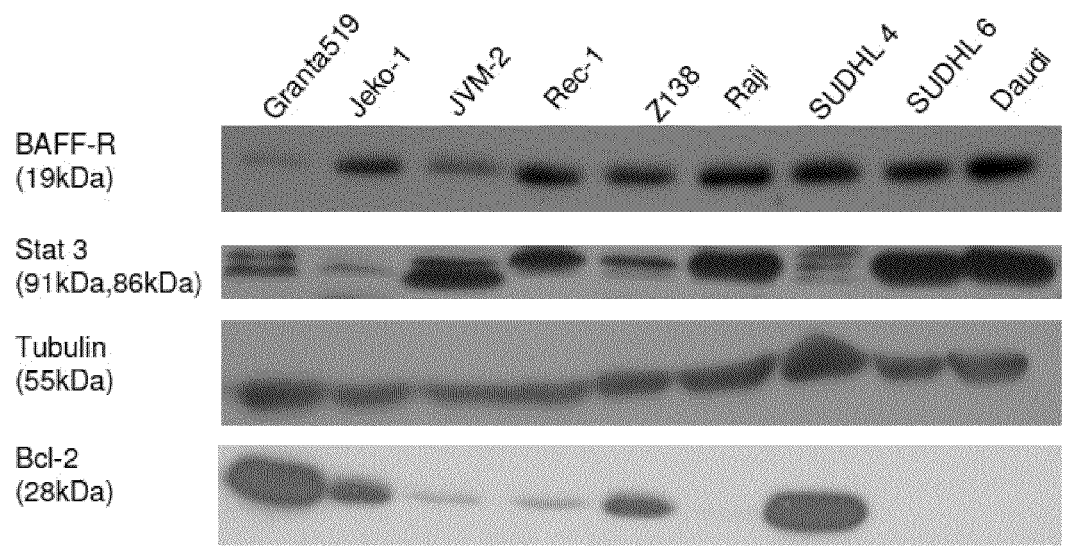
FIG. 48 is a Western blot, illustrating the expression of STAT3, Bcl-2 and BAFF-R in several cell lines (Granta519, Jeko-1, JVM-2, Rec-1, Z138, Raji, SUDHL 4, SUDHL 6, and Daudi).

As shown in FIG. 48, Jeko-1 and Z138 expressed all STAT3 and Bcl-2 at easily detectable levels and also showed high BAFF-R levels. Hence the studies described herein were conducted with these two cell lines.

Gel Shift Assay.

Figure 40C:
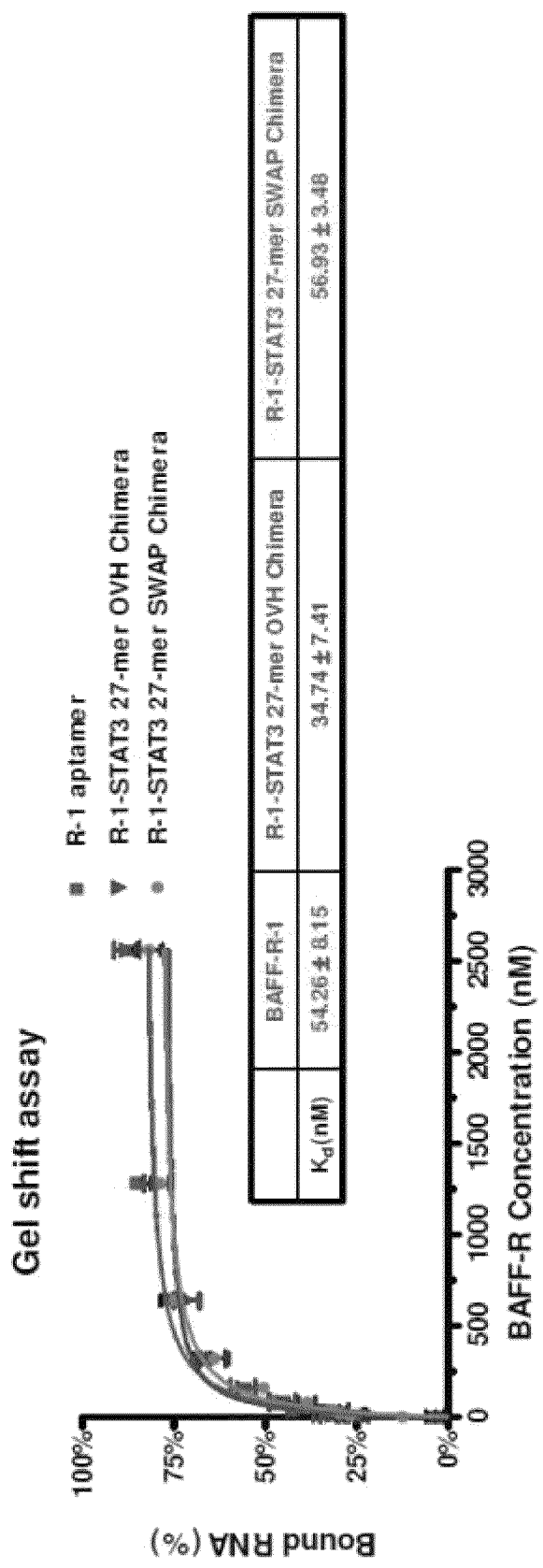
FIG. 40C shows a binding curve from a gel shift assay. The aptamer-siRNA chimeric RNAs that have comparable $K_d$ values as well as parental aptamers specifically bind the human BAFF-R protein. Data represent the average of three replicates.
Figure 49A:
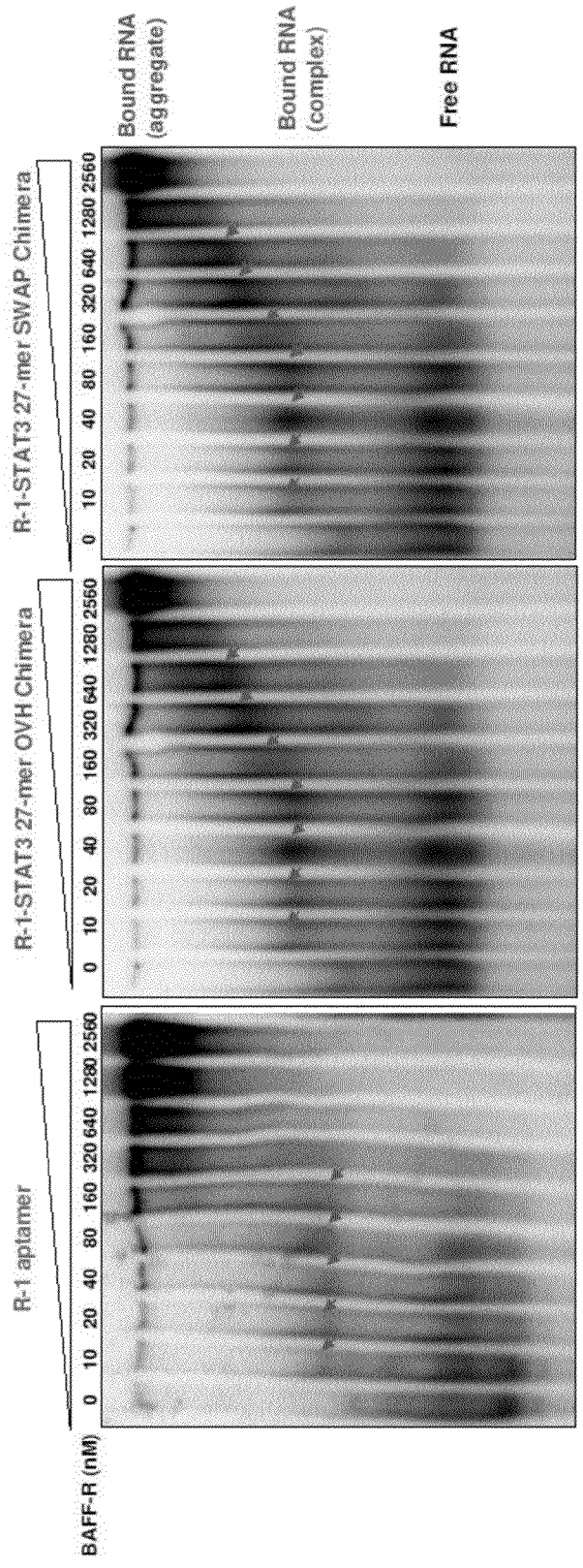
FIG. 49A illustrates the binding affinity of the R-1-STAT3 27mer OVH chimera and the R-1-STAT3 27-mer SWAP chimera by gel shift assay.
Figure 49B:
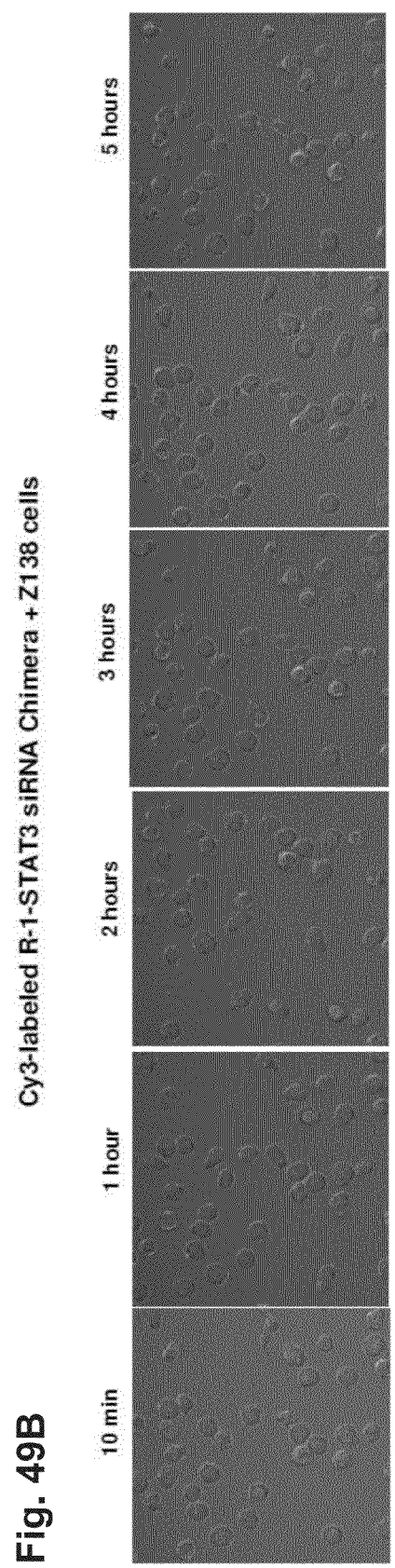
FIG. 49B illustrates the successful internalization of the R-1-STAT3 27mer OVH chimera and the R-1-sTAT3 27-mer SWAP chimera by Cy3-labeled chimera in Z138 cells.

The binding affinities of the chimeras for BAFF-R protein were assessed by gel shift assay (FIG. 40C and FIG. 49A). These data indicate that the two chimeras (27-mer OVH chimera: 35 nM of $K_d$; 27-mer SWAP chimera: 56 nM of $K_d$) maintain approximately the same binding affinities as parental R-1 aptamer (54 nM of $K_d$). To determine whether the bound chimera is internalized by BAFF-R expressing cells, real-time Z-axis confocal microscopy was performed (FIG. 41A-C and FIG. 49B). The Cy3-labeled chimeras were successfully internalized into BAFF-R expressing cells (Jeko-1 and Z138) after 5 h post treatment. Similar with their parental aptamer R-1, FIG. 41C showed that aptamer-siRNA chimeras also were internalized into the cytoplasm of cells (FIG. 41C).

Figure 42A:
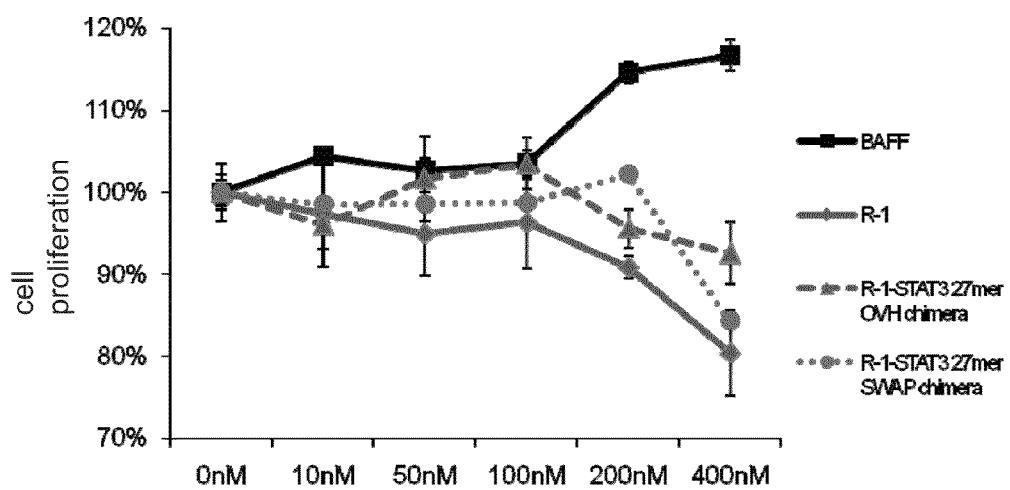
FIG. 42A shows cellular proliferation of aptamer-siRNA chimera treated NHL cell line. BAFF ligand can increase cell proliferation upon binding to BAFF-R on B-cells. Chimeras showed no increase in cell proliferation in Jeko-1 cells 48 h post treatment in MTS assays as described above.
Figure 42B:
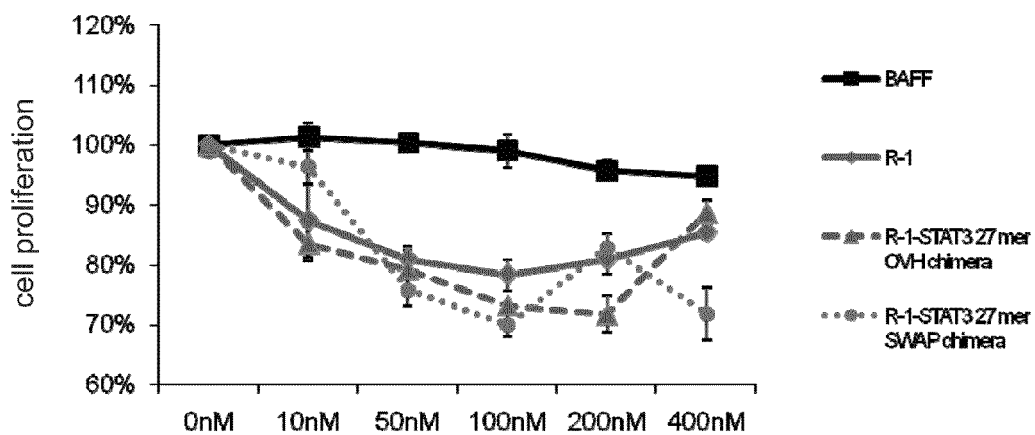
FIG. 42B shows cellular proliferation of aptamer-siRNA chimera treated NHL cell line. BAFF ligand can increase cell proliferation upon binding to BAFF-R on B-cells. Chimeras showed no increase in cell proliferation in Z138 cells 48 h post treatment in MTS assays as described above.

Moreover, MTS assays were performed to determine whether the chimeras enhance cell proliferation in B-cell lines. As shown in FIG. 42, both chimeras behaved similar to the parental R-1 aptamer in both Jeko-1 (FIG. 42A) and Z138 (FIG. 42B) cell lines and showed no increase in cell proliferation.

Figure 43:
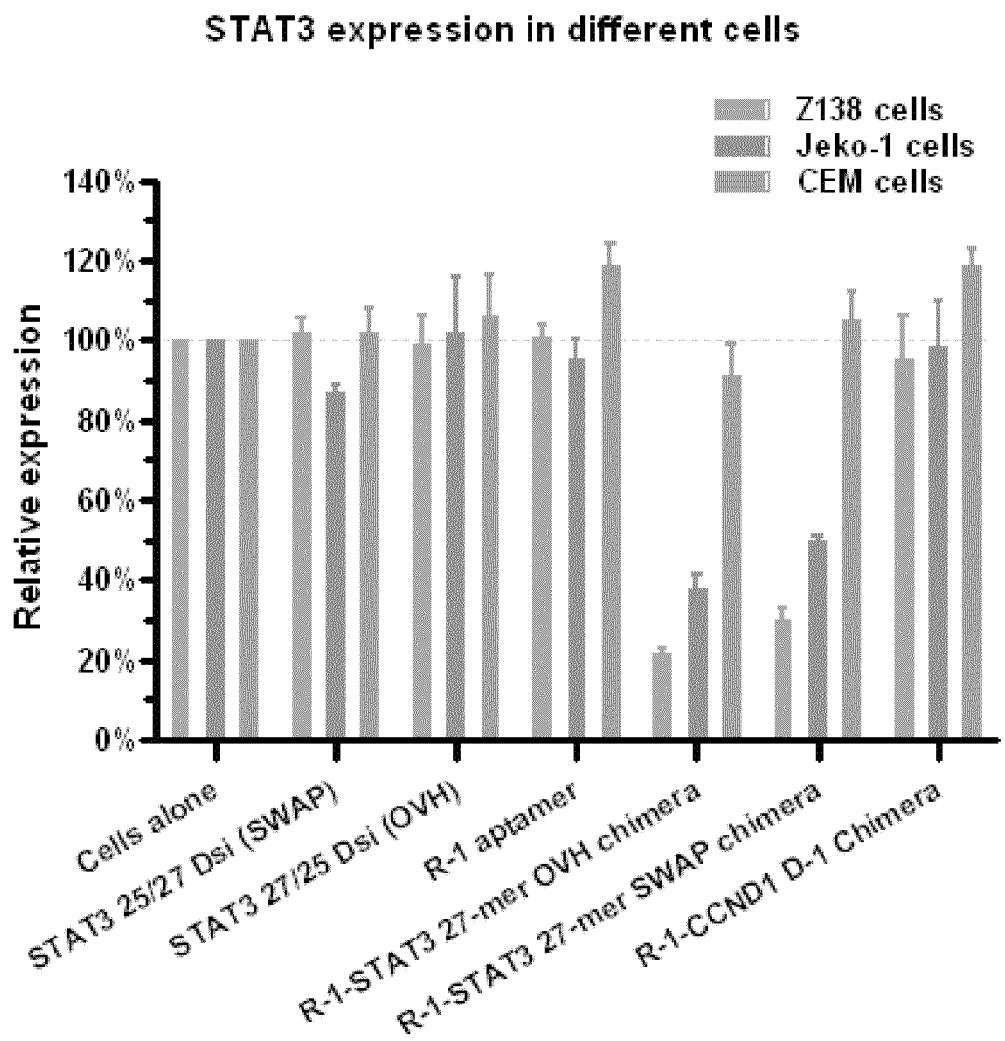
FIG. 43: Aptamer delivered siRNAs specifically knockdown STAT3 expression. Relative STAT3 mRNA levels were detected by real-time PCR, with GAPDH as internal control. Jeko-1, Z138 and OEM cells were incubated with BAFF-R aptamers and chimeras. As control siRNA alone, R-1 aptamer, irrelevant aptamer (gp120) and BAFF-R aptamer-Cyclin D1 siRNA chimeras were employed. Experiments were performed in triplicate.

BAFF-R Aptamer-STAT3 siRNA Chimeras Specifically Knockdown STAT3 Expression Levels Via RNAi Pathway To confirm that the siRNA component was functioning along with the aptamer, following internalization of the BAFF-R aptamer-siRNA chimeras in BAFF-R expressing cells, the relative levels of inhibition of STAT3 expression was also evaluated. Cells were incubated with R-1-STAT3 siRNA chimeras, siRNAs alone, R-1 aptamer and as further controls a non-functional R-1-CCND1 siRNA chimera. After 2 days of post-treatment, treated cells were harvested, the total RNA was extracted and the expression level of STAT3 mRNA was determined by quantitative RT-PCR (qRT-PCR) (FIG. 43). Only R-1-STAT3 siRNA chimeras (27-mer OVH and 27-mer SWAP) were able to knockdown STAT3 mRNA expression while the siRNA and the R-1 aptamer samples alone did not have an effect. The 27-mer OVH chimera was slightly more potent than the 27-mer SWAP chimera. The ability of the aptamer-siRNA chimeras to knockdown STAT3 was B-cell specific. As shown in FIG. 43, control cells (OEM T-cells) treated with either of the R-1-STAT3 siRNA chimeras showed no STAT3 mRNA reduction.

Figure 44A:
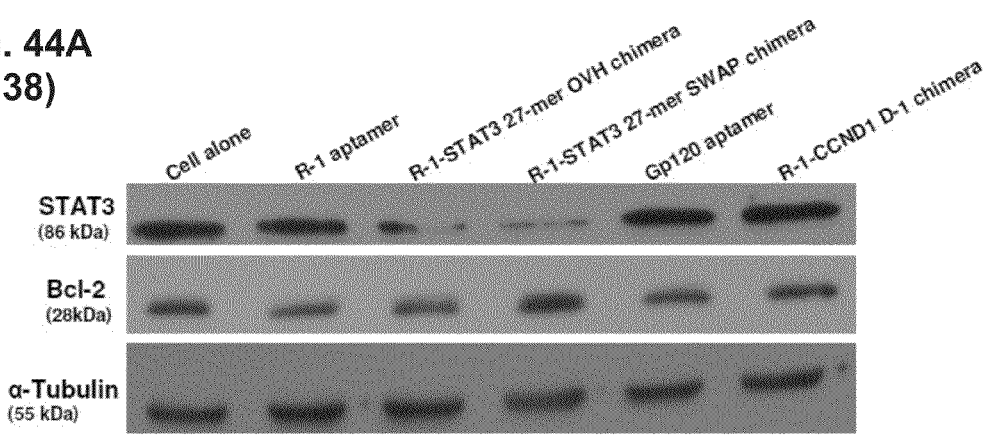
FIG. 44A shows STAT3 protein reduction and Bcl-2 protein levels measured by Western blot analysis in Z138 cells. Gp120 aptamer and untreated cells served as controls. As loading control α-tubulin was used.
Figure 44B:
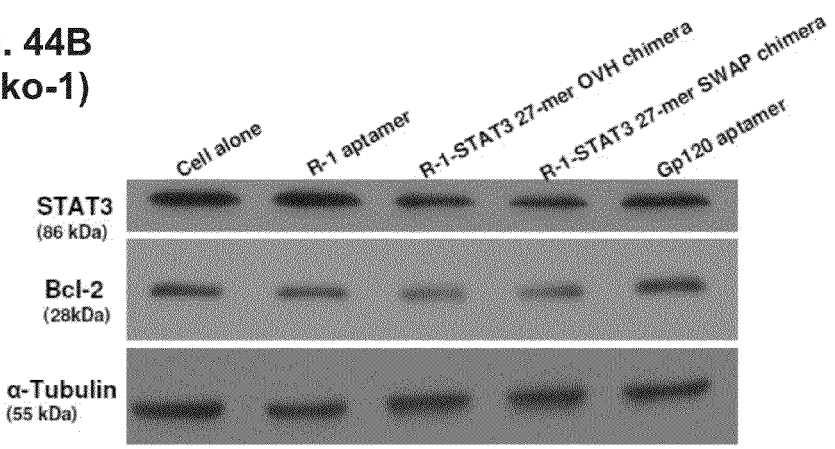
FIG. 44B shows STAT3 protein reduction and Bcl-2 protein levels measured by Western blot analysis in Jeko-1 cells. Gp120 aptamer and untreated cells served as controls. As loading control α-tubulin was used.

Furthermore, STAT3 and Bcl-2 protein levels were detected in Z138 (FIG. 44A) and Jeko-1 (FIG. 44B) cells by Western blot as described above. As controls, the R-1 aptamer alone and the unspecific gp120 apatmer were used for both cell lines. To ensure the specificity of the STAT3 siRNA, a non-functional R-1-CCND1 siRNA chimera (targeting Cyclin D1) were also tested in Z138 cells. Consistent with the qRT-PCR data of mRNA expression (FIG. 43), only the R-1-STAT3 siRNA chimeras showed STAT3 protein reduction in both cell lines (FIG. 44A, B). The tested aptamers or chimeras did not show a Bcl-2 increase. In Jeko-1 cells, the R-1 aptamer and the R-1-siRNA chimeras showed a decrease in Bcl-2.

Figure 51:
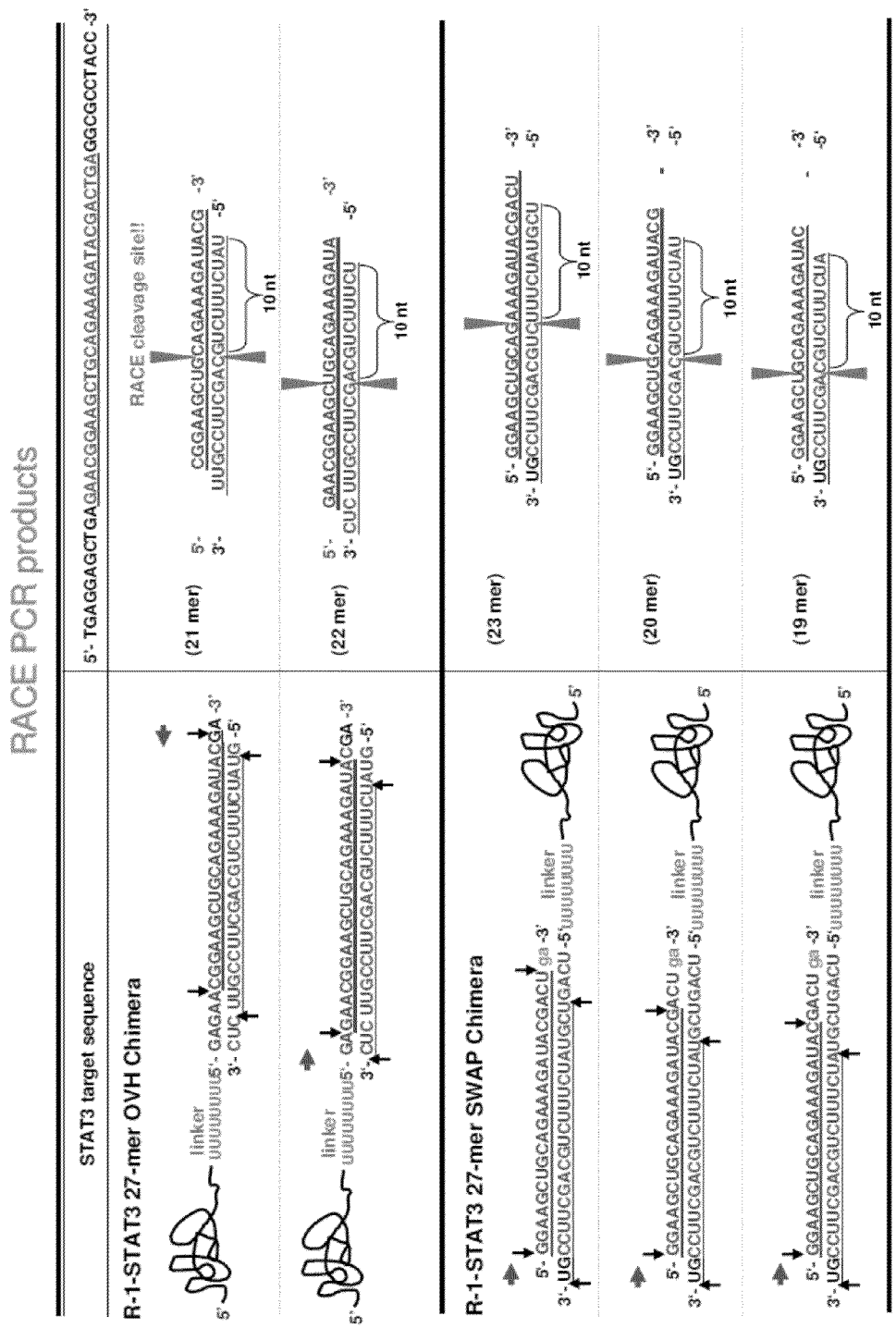
FIG. 51 illustrates the Ago2 cleavage sites and proposed direction of Dicing in the 27-mer OVH chimera and the 27-mer SWAP chimera.

Additionally, a modified 5'-RACE (rapid amplification of cDNA ends) PCR was performed to ensure RNAi-mediated STAT3 mRNA cleavage (FIGS. 50 and 51). Since it has been established that Ago2 mediated cleavage of mRNA between base 10 and 11 relative to the 5' end of the siRNA guide strand (Matranga et al. 2005; Meister et al. 2004) the RACE PCR product should display a linker addition at the base 10 nucleotides downstream from the 5' end of the siRNA guide strand. PCR bands of the predicted lengths were detected in the total RNAs from Jeko-1 or Z138 cells treated with the chimeras following two nested PCR reactions. No appropriate size products were observed in the non-treated cells or in the siRNA alone-treated cells (FIG. 50). The individual clones were sequenced to verify the expected PCR products. Several various cleavage sites were found in the samples from the two chimeras' treatment. FIG. 51 indicates the Ago2 cleavage sites and proposed direction of Dicing. For the 27-mer OVH chimera, two major cleavages take place, suggesting that Dicer might bi-directionally enter the dsiRNA to generate different 21 or 22 mer siRNA species. In the case of the 27-mer SWAP chimera, although different cleavage sites were generated, the same direction of Dicer entry was observed, in which Dicer always enter the dsiRNA from 3' end of antisense strand and generate different siRNA species of various length (19, 20 or 23 mer siRNAs). The results showed that the target cleavage sites correlated with Dicer produced siRNAs as revealed by Illumina sequencing (data not shown). These results indicate that the chimeras delivered siRNAs are processed intracellularly and trigger sequence specific degradation of the STAT3 target mRNA.

Example 5

Changes in Gene Expression in B Cell Lymphoma Cells after Treatment with B Cell Aptamers A microarray assay was performed to determine the effect of the BAFF-R aptamers on B cell gene expression levels. Briefly, Z138 cells were grown and maintained in RPMI1640 with 10% FBS for 48 hours. 24 hours prior to the microarray assay, the cell medium was replaced. After counting the cells, the Z138 cells were centrifuged and fresh medium was added. The cells were seeded in a 24-well plate, with $2\times10^5$ cells per well (400 µl). The cells were incubated for 20-30 minutes before adding the RNA sample. Samples were added to the wells, at an RNA work concentration of 400 nM (400 nM×0.4 mL=160 pmol) as shown in Table 6 below.

TABLE 6

RNA working concentration 400 nM; 400 µL per well (24 well); total 160 pmol

| Sample | Exp. RNA Stock[a] Concentration | Volume (µl) | Final 1 × 24-well (ng) | RNA or ligand 2.0 X Mixes |
|---|---|---|---|---|
| (1) Cells alone | 0 | 0 | 0 | 0 |
| (2) BAFF ligand[b] | 10 µM | 16 | 2721.12 | 32 |
| (3) R-1 aptamer | 20 µM | 8 | 4276.8 | 16 |
| (4) BAFF ligand and R-1 aptamer | 20 µM | 8 + 4 | 3498.96 | 24 |
| (5) R-22 aptamer | 20 µM | 8 | 4224 | 16 |

[a]Stock Solution: 20 µg powder, add 100 µl ddH2O to make 200 ng/µl stock solution. For the reaction solution, 170.07 ng/µl (10 µM) was made for the cell culture assay.
[b]B-cell Activating Factor Human Recombinant (BAFF Human)(Prosbec-Tany TechnoGene Ltd.: CYT-307) (Amino Acid Sequence: MAVQGPEETV TQDCLQLIAD SETPTIQKGS YTFVPWLLSF KRGSALEEKE NKILVKETGY FFIYGQVLYT DKTYAMGHLI QRKKVHVFGD ELSLVTLFRC IQNMPETLPN NSCYSAGIAK LEEGDELQLA IPRENAQISL DGDVTFFGAL KLL (MW: 17.007 kDa))

After adding the RNA samples, the cells were further incubated at 37 degrees for 48 hours. Total RNA was then isolated and collected with STAT-60 (TEL-TEST, Friendswood, Tex.) and a Microarray assay was performed to detect all human mRNA in a duplex assay. The results of the microarray assay files are summarized in Table 7 below.

TABLE 7

| File Name | BAFF ligand? | BAFF Aptamer? | Abbreviation |
|---|---|---|---|
| E509_(1_NoTreat).CEL | No (Control) | No (Control) | Group 1 |
| E510_(2_Treat.1).CEL | Yes | No | Group 2 |

TABLE 7-continued

| File Name | BAFF ligand? | BAFF Aptamer? | Abbreviation |
|---|---|---|---|
| E511_(3_Treat.2).CEL | No | Aptamer R-1 | Group 3 |
| E512_(4_Treat.3).CEL | Yes | Aptamer R-1 | Group 4 |
| E513_(5_Treat.4).CEL | No | Aptamer R-22 | Group 5 |
| E514_(6_NoTreat).CEL | No (Control) | No (Control) | Group 1 |
| E515_(7_Treat.1).CEL | Yes | No | Group 2 |
| E516_(8_Treat.2).CEL | No | Aptamer R-1 | Group 3 |
| E517_(9_Treat.3).CEL | Yes | Aptamer R-1 | Group 4 |
| E518_(10_Treat.4).CEL | No | Aptamer R-22 | Group 5 |

Several genes in the cells were differentially expressed when treated with the R-1 aptamer, the R-1 aptamer+BAFF ligand, BAFF ligand alone or the R-22 aptamer as compared to the cells alone (See Table 8 below).

TABLE 8

| Comparison | Up-regulated | Down-regulated |
|---|---|---|
| Group 2 vs. 1 (BAFF ligand vs. cell alone) | 361 probes (154 genes) | 358 probes (220 genes) |
| Group 3 vs. 1 (R-1 aptamer vs. cell alone) | 77 probes (36 genes) | 73 probes (38 genes) |
| Group 4 vs. 1 (BAFF ligand & R-1 aptamer vs. cell alone) | 103 probes (40 genes) | 88 probes (53 genes) |
| Group 5 vs. 1 R-22 aptamer vs. cell alone | 87 probes (43 genes) | 95 probes (49 genes) |

Many of the most common genes that were upregulated or downregulated upon treatment with the various aptamers or BAFF ligand are associated with networks and pathways associated with cellular proliferation and hematological development. The most common upregulated genes were Interleukin-10 (IL-10), Small nucleolar RNA U77 (SNORD77), Carbonic anhydrase 3 (CA3) and NOL7.

Interleukin-10 (IL-10 or IL10), also known as human cytokine synthesis inhibitory factor (CSIF), is an anti-inflammatory cytokine. In humans IL-10 is encoded by the IL10 gene. It also enhances B cell survival, proliferation, and antibody production. This cytokine can block NF-κB activity, and is involved in the regulation of the JAK-STAT signaling pathway. IL-10 is capable of inhibiting synthesis of pro-inflammatory cytokines like IFN-γ, IL-2, IL-3, TNFα and GM-CSF made by cells such as macrophages and regulatory T-cells. IL-10 also displays potent abilities to suppress the antigen presentation capacity of antigen presenting cells. However, it is also stimulatory towards certain T cells, mast cells and stimulates B cell maturation and antibody production. In addition, BAFF has been shown to regulate IL-10 by Yang et al.

Small nucleolar RNA SNORD77: U77 belongs to the C/D family of snoRNAs. It is predicted to guide 2'O-ribose methylation of large 28S rRNA subunit at position A1521. The C/D snoRNAs U44, U47, U74, U75, U76, U78, U79, U80 and U81 share the same host gene as U77 (non-coding).

Carbonic anhydrase 3 (CA3, CAIII) is an enzyme that in humans is encoded by the CA3 gene. CAIII is a member of a multigene family (at least six separate genes are known) that encode carbonic anhydrase isozymes. These carbonic anhydrases are a class of metalloenzymes that catalyze the reversible hydration of carbon dioxide and are differentially expressed in a number of cell types. The expression of the CA3 gene is strictly tissue-specific and present at high levels in skeletal muscle and much lower levels in cardiac and smooth muscle. A proportion of carriers of Duchenne muscle dystrophy have a higher CA3 level than normal. The gene spans 10.3 kb and contains seven exons and six introns.

The most common downregulated genes across the treatment groups were Homo sapiens gene BTBD11 (encodes BTB (POZ) domain containing 11), LOC158572 and MGC24103.

Several of the upregulated genes were represented and overlapped in at least one of the following categories: 1) Regulation of lymphocyte apoptosis, 2) Positive regulation of necrotic cell death, 3) Positive regulation of cell death, or 4) apoptotic nuclear changes (Table 9). Each cell in Table 9 contains fold-change, followed by a raw p-value. Bold cells represent genes found in the most commonly upregulated or downregulated genes in the gene list described above.

TABLE 9

|  | Group 2 | Group 3 | Group 4 | Group 5 |
| --- | --- | --- | --- | --- |
| IL10[1] | FC = 1.57 | FC = 1.01 | FC = 1.61 | FC = 1.46 |
|  | p = 0.0014 | p = 0.94 | p = 0.0011 | p = 0.0031 |
| FAS[2,3] | FC = 1.25 | FC = −1.01 | FC = 1.22 | FC = 1.25 |
|  | p = 0.020 | p = 0.99 | p = 0.027 | p = 0.018 |
| MOAP1[4] | FC = 1.24 | FC = 1.08 | FC = 1.15 | FC 1.18 |
|  | p = 0.018 | p = 0.29 | p = 0.08 | p = 0.05 |

[1]Involved in regulation of lymphocyte apoptosis
[2]Involved in pPositive regulation of necrotic cell death
[3]Involved in positive regulation of cell death
[4]Involved in apoptotic nuclear changes In addition, as shown in FIGS. 57-60, the top differentially expressed genes with each treatment group were evaluated as compared to cells alone (control).

Figure 52:
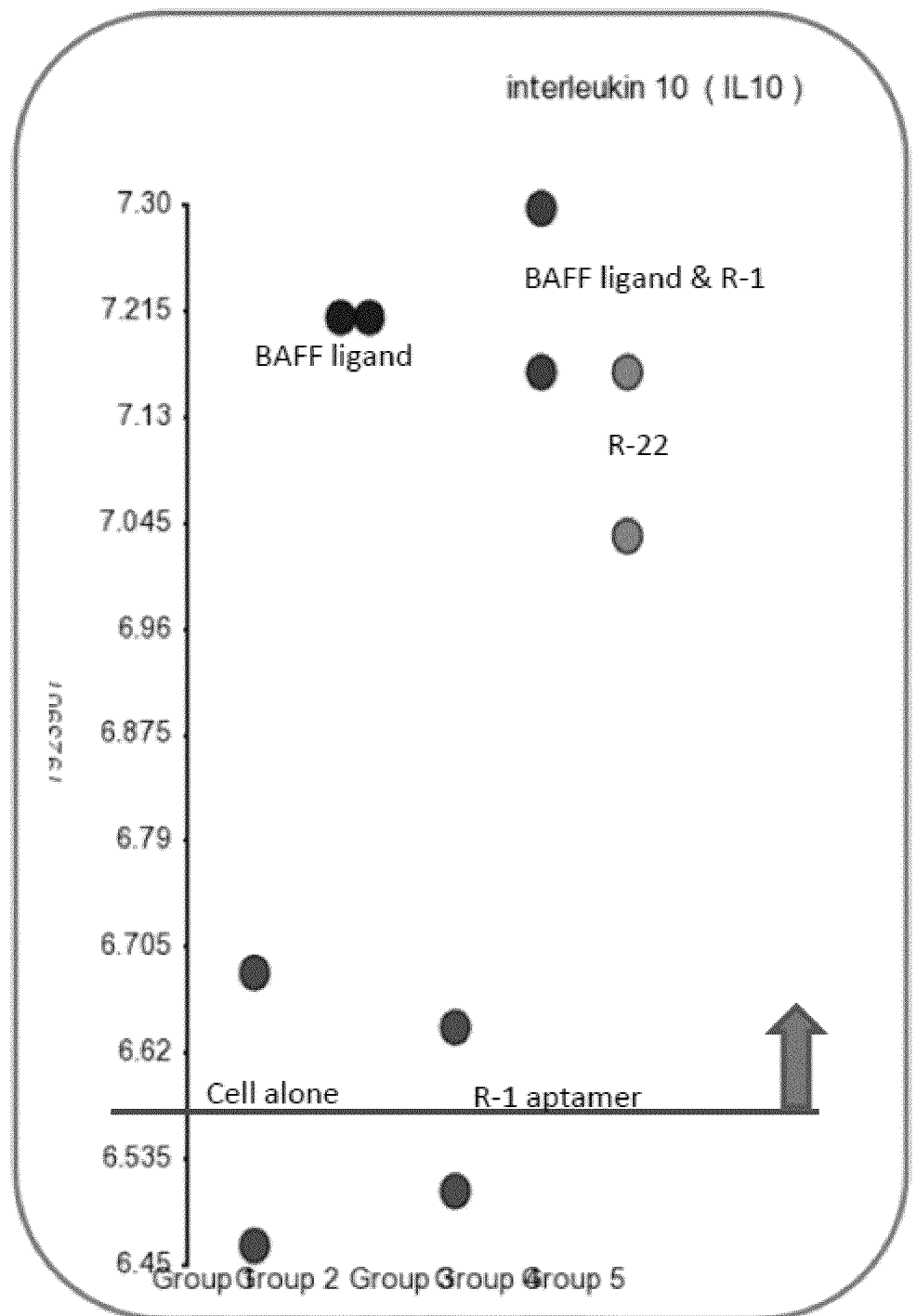
FIG. 52 illustrates the effect of treatment with (1) BAFF ligand, (2) BAFF ligand and R-1 aptamer, (3) R-22 aptamer, (4) R-1 aptamer and (5) the cell alone (control) on the expression of IL-10 in Z138 cells.
Figure 53:
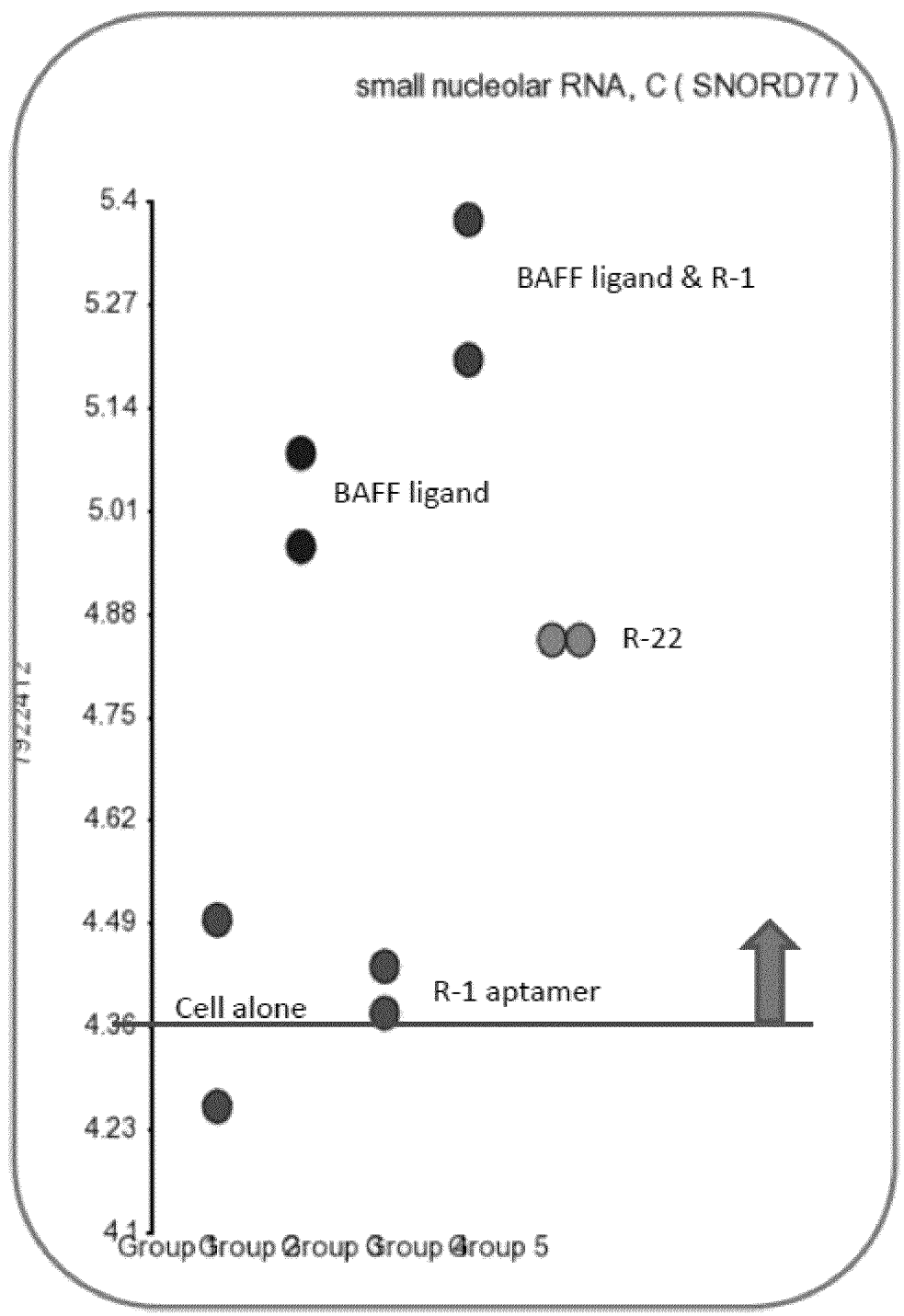
FIG. 53 illustrates the effect of treatment with (1) BAFF ligand, (2) BAFF ligand and R-1 aptamer, (3) R-22 aptamer, (4) R-1 aptamer and (5) the cell alone (control) on the expression of SNORD77 in Z138 cells.
Figure 54:
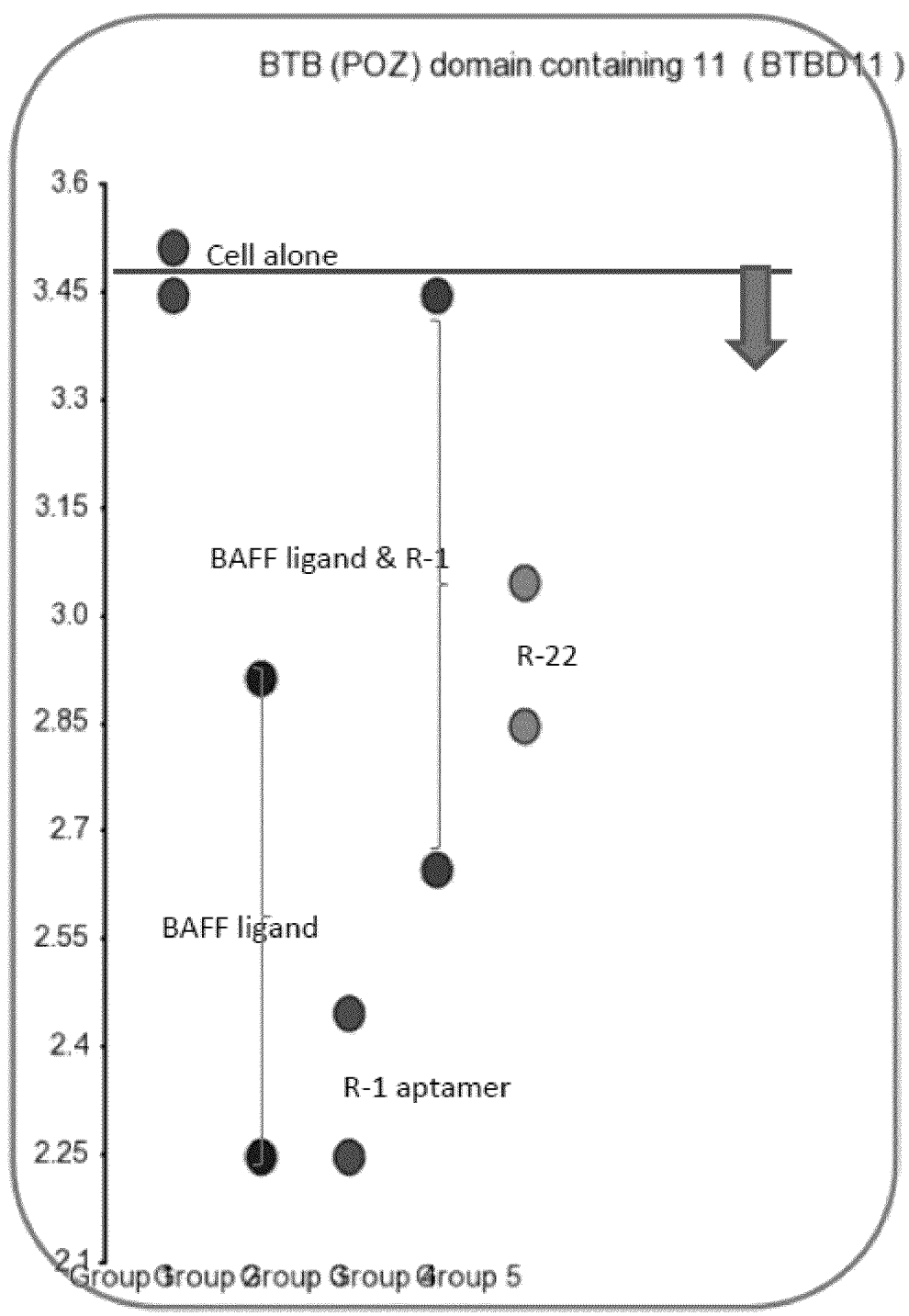
FIG. 54 illustrates the effect of treatment with (1) BAFF ligand, (2) BAFF ligand and R-1 aptamer, (3) R-22 aptamer, (4) R-1 aptamer and (5) the cell alone (control) on the expression of BTBD11 in Z138 cells.
Figure 55:
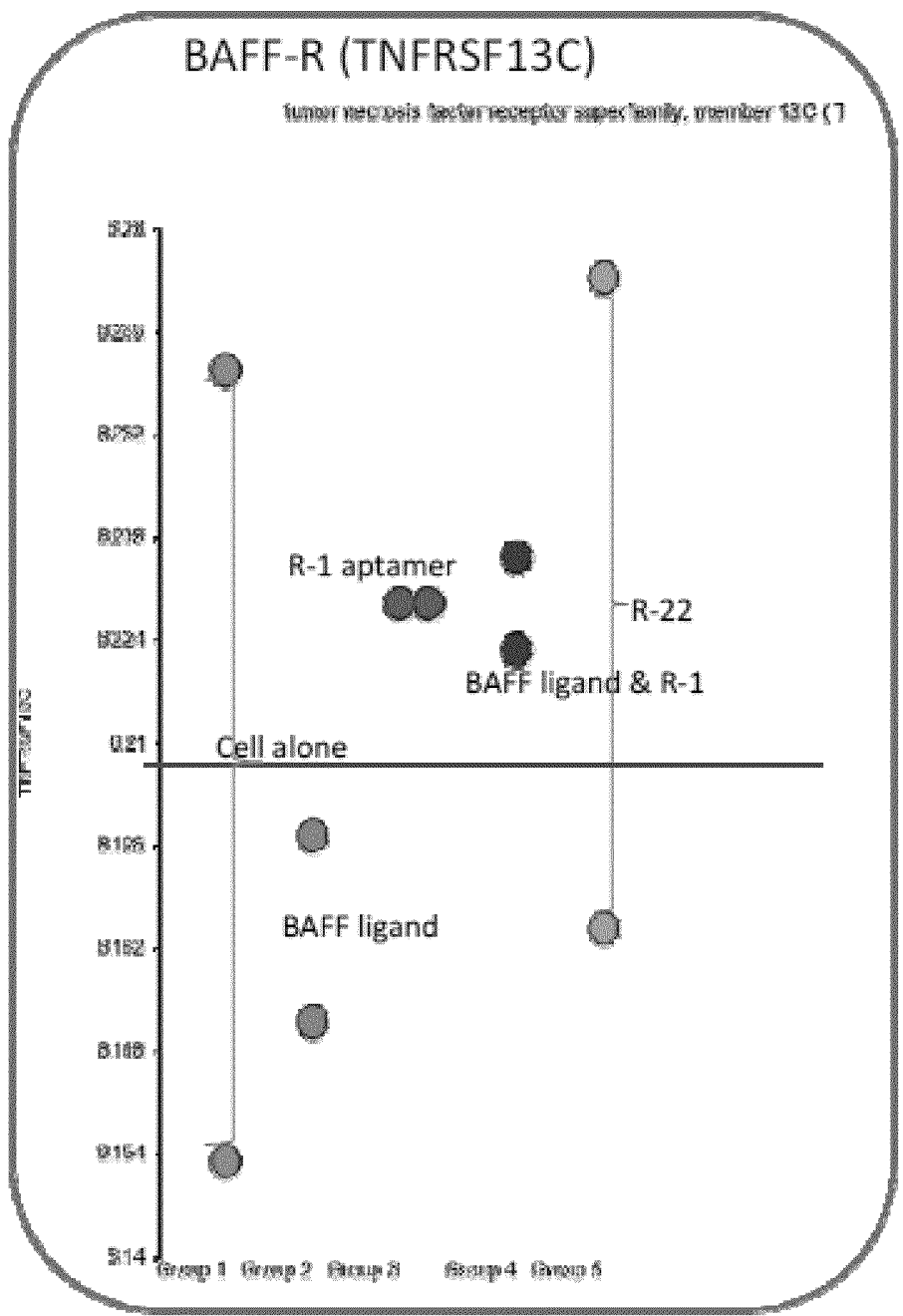
FIG. 55 illustrates the effect of treatment with (1) BAFF ligand, (2) BAFF ligand and R-1 aptamer, (3) R-22 aptamer, (4) R-1 aptamer and (5) the cell alone (control) on the expression of TNFRSF13C (tumor necrosis factor receptor superfamily, member 13C) in Z138 cells.
Figure 56:
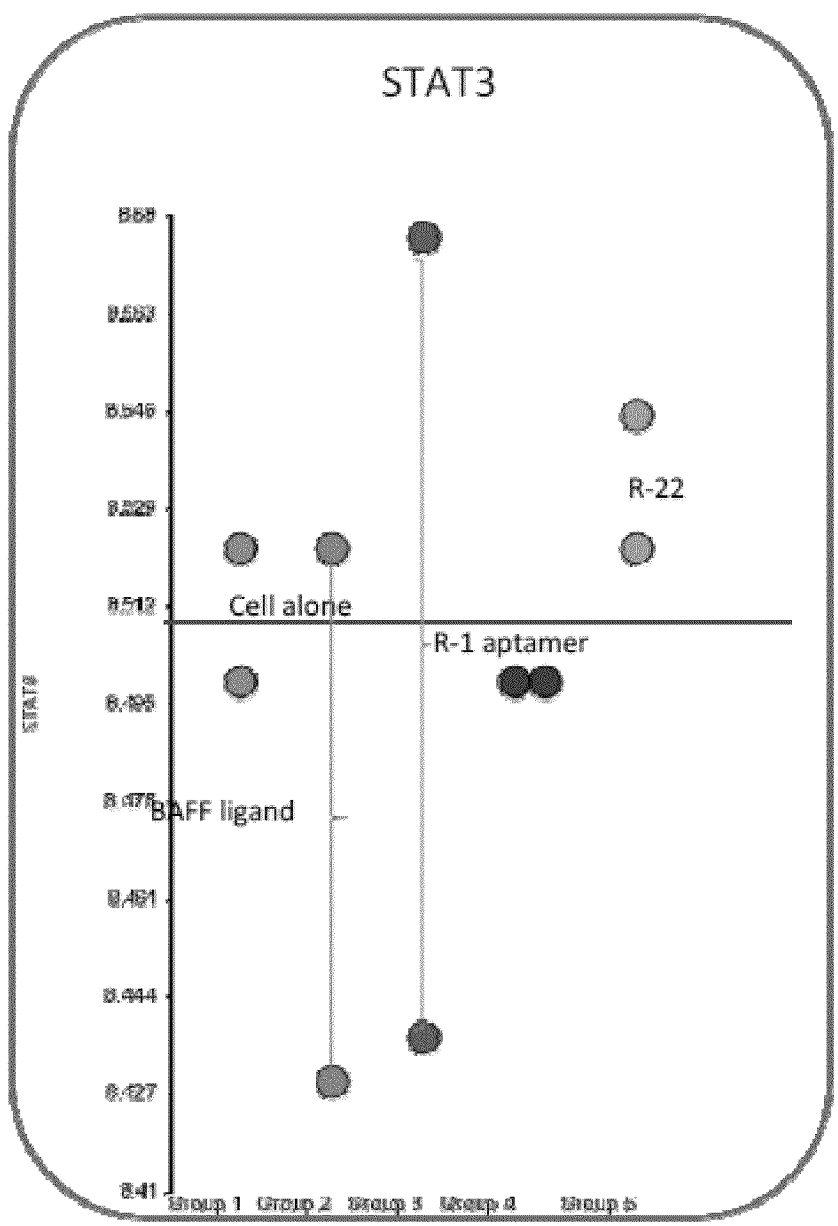
FIG. 56 illustrates the effect of treatment with (1) BAFF ligand, (2) BAFF ligand and R-1 aptamer, (3) R-22 aptamer, (4) R-1 aptamer and (5) the cell alone (control) on the expression of STAT3 in Z138 cells.

The R-1 aptamer has a similar expression profile as the cells alone with respect to upregulation of IL-10 (FIG. 52) and SNORD77 (FIG. 53). This indicates that, unlike the BAFF ligand, R-22 and BAFF ligand plus R-1, R-1 does not enhance proliferation and survival of cancer cells via these upregulated genes. Downregulation of BTBD11 expression is shown in FIG. 54. The effect of treatment with R-1 aptamer, BAFF ligand, R-22, and BAFF ligand plus R-1 on the expression of TNFRSF13C (tumor necrosis factor receptor super family, member 13C) and STAT3 were also determined (FIGS. 55 and 56). Minimal changes in expression were detected, indicating that the aptamer-siRNA chimeras above have additional value as a treatment above and beyond the use of the aptamer alone.

Example 6

R-1 Aptamer Eradicates Tumor in Balb/c Mice

Figure 61:
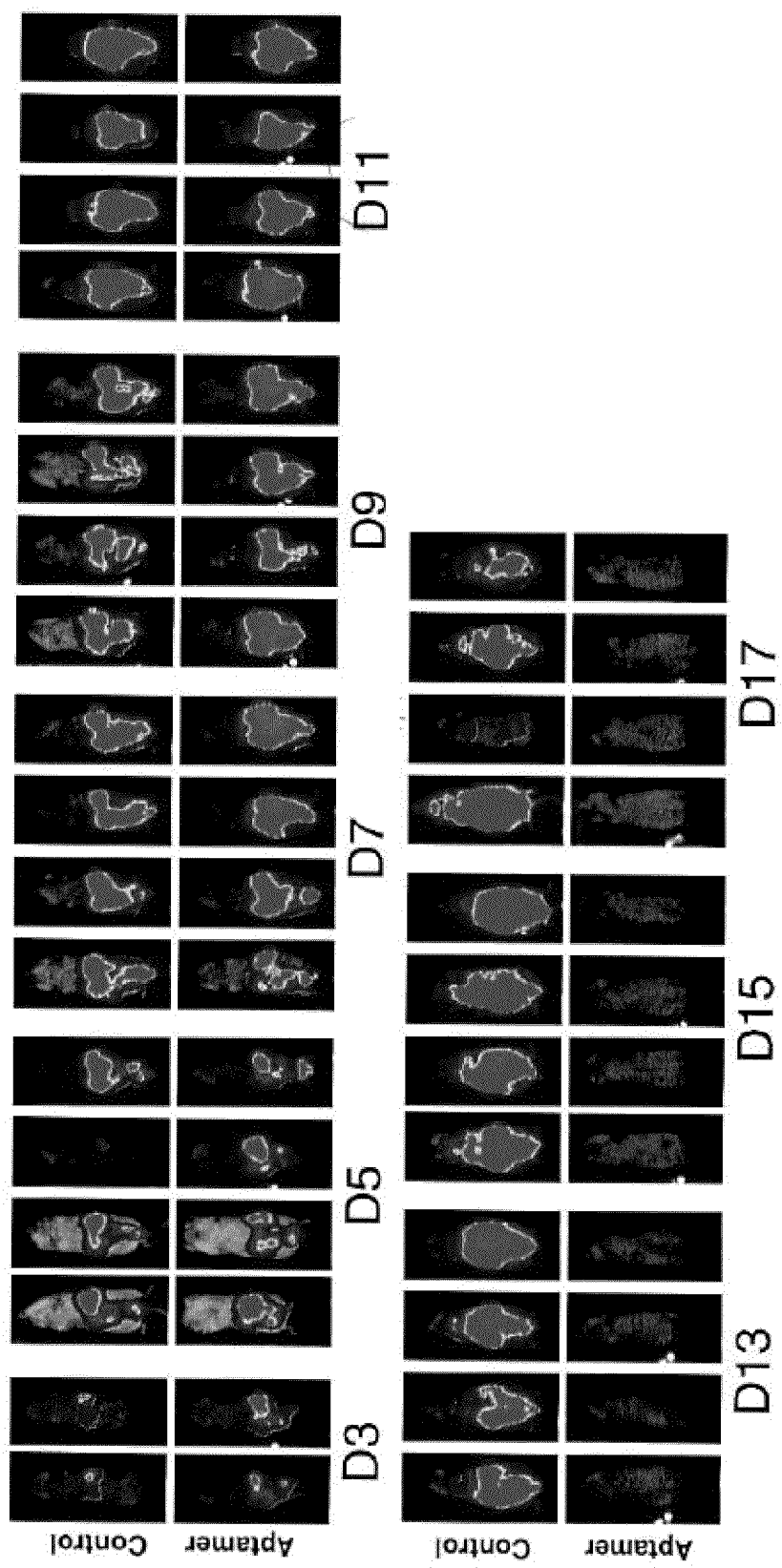
FIG. 61 is a series of images illustrating the effect of R-1 aptamer treatment in tumor-bearing mice. The first row (Control) shows representative images of mice injected with a saline solution in place of the aptamer. The second row (Aptamer) shows representative images of mice injected with the aptamer. For each timepoint (Day (D), 5, 7, 9, 11, 13, 15 and 17), mice were treated with 0.01 nmol/g every other day (left 4 cells in each time point) or 0.05 nmol/g every other day (right 4 cells in each time point). Aptamer treatment was stopped on D11.

Balb/c (white) mice were inoculated with tumor cells (BCL-1 lymphome cell line) that were stably transduced with a luciferase-expressing vector. After the tumor was allowed to grow in the mice, the R-1 BAFF aptamer was injected every other day, starting on Day 0 (i.e., on Day 0, 2, 4, 6, 8, 10). Images were then obtained on days following aptamer injection (i.e., on Day 1, 3, 5, 7, 9, 11, 13, 15, 17). Approximately one hour prior to imaging, the mice were injected with luciferin for detection of tumor cells within the mice. The mice were imaged using a Xenogen machine, which detects luciferase expression. The image was processed to quantify tumor signal to provide qualitative and quantitative data. Results are shown in FIG. 61. As shown in FIG. 61, the tumor was no longer detectable by D13, indicating that the aptamer was effective not only in suppressing tumor proliferation, but was also effective in eradicating the tumor completely. Therefore, the aptamers provided herein may be used as a treatment to suppress or inhibit B cell proliferation and survival in B cell malignancies, and may be used to eradicate primary or metastatic tumors derived from B cell malignancies.

REFERENCES

The references listed below, and all references cited in the specification are hereby incorporated by reference in their entireties, as if fully set forth herein.

1. Aagaard L., Rossi J. J. (2007). RNAi therapeutics: Principles, prospects, and challenges. *Adv. Drug Deliv. Rev.* 59, 75-86.
2. Amarzguioui M., Rossi J. J., Kim D. (2005) Approaches for chemically synthesized siRNA and vector-mediated RNAi. *FEBS Lett,* 579, 5974-5981
3. Amarzguioui, M., et al., Rational design and in vitro and in vivo delivery of Dicer substrate siRNA. Nat Protoc, 2006. 1(2): p. 508-17.
4. Anderson, D. R., et al., Targeted anti-cancer therapy using rituximab, a chimaeric anti-CD20 antibody (IDEC-C2B8) in the treatment of non-Hodgkin's B-cell lymphoma. Biochem Soc Trans, 1997. 25(2): p. 705-8.
5. Bakhshi, A., et al., Cloning the chromosomal breakpoint of t(14;18) human lymphomas: clustering around JH on chromosome 14 and near a transcriptional unit on 18. Cell, 1985. 41(3): p. 899-906.
6. Barik S. (2008)RNAi, Design and Application. *Methods in Molecular Biology.* 442 (Humana Press)
7. Batten M, Groom J, Cachero T G, et al. BAFF mediates survival of peripheral immature B lymphocytes. *J Exp Med.* 2000; 192(10):1453-1466. Prepublished on 2000 Nov. 21 as DOI.
8. Bhindi, R., et al., Brothers in arms: DNA enzymes, short interfering RNA, and the emerging wave of small-molecule nucleic acid-based gene-silencing strategies. Am J Pathol, 2007. 171(4): p. 1079-88.
9. Birmingham A., Anderson E. M., Reynolds A., Ilsley-Tyree D., Leake D., Fedorov Y., Baskerville S., Maksimova E., Robinson K., Karpilow J., Marshall W. S., Khvorova A. (2006) 3' UTR seed matches, but not overall identity, are associated with RNAi off-targets. *Nat Methods,* 3, 199-204
10. Bossen C., Schneider P. (2006) BAFF, APRIL and their receptors: Structure, function and signaling. *Seminars in Immunology,* 18, 263-275.
11. Bowman T, Garcia R, Turkson J, Jove R. STATs in oncogenesis. Oncogene. 2000; 19(21):2474-2488. Prepublished on 2000 Jun. 13 as DOI 10.1038/sj.onc.1203527.
12. Brauer, D. S., et al., Degradable phosphate glass fiber reinforced polymer matrices: mechanical properties and cell response. J Mater Sci Mater Med, 2008. 19(1): p. 121-7.
13. Briones J, Timmerman J M, Hilbert D M, Levy R. BLyS and BLyS receptor expression in non-Hodgkin's lymphoma. *Exp Hematol.* 2002; 30(2):135-141. Prepublished on 2002 Feb. 2 as DOI 50301472X01007743 [pii].
14. Brummelkamp T. R., Bernards R., Agami R. (2002) A system for stable expression of short interfering RNAs in mammalian cells. *Science,* 296, 550-553.
15. Byrom M., Pallotta V., Brown D., Ford L. (2002) Visualizing siRNA in mammalian cells: Fluorescence analysis of the RNAi effect *Ambion Technotes,* 9 (3), 5
16. Campo E, Raffeld M, Jaffe E S. Mantle-cell lymphoma. *Semin Hematol.* 1999; 36(2):115-127.
17. Gaudy A. A. et al. (2003) A micrococcal nuclease homologue in RNAi effector complexes. *Nature,* 425, 411

18. Chen, R. W., et al., Truncation in CCND1 mRNA alters miR-16-1 regulation in mantle cell lymphoma. Blood, 2008. 112(3): p. 822-9.
19. Chu, T. C., et al., Aptamer mediated siRNA delivery. Nucleic Acids Res, 2006. 34(10): p. e73.
20. Coiffier, B., Current strategies for the treatment of diffuse large B cell lymphoma. Curr Opin Hematol, 2005. 12(4): p. 259-65.
21. Craxton A, Magaletti D, Ryan E J, Clark E A. Macrophage- and dendritic cell—dependent regulation of human B-cell proliferation requires the TNF family ligand BAFF. Blood. 2003; 101(11):4464-4471. Prepublished on 2003 Jan. 18 as DOI 10.1182/blood-2002-10-3123 2002-10-3123 [pii].
22. Chu T C, Marks J W, 3rd, Lavery L A, et al. Aptamer:toxin conjugates that specifically target prostate tumor cells. Cancer Res. 2006; 66(12):5989-5992. Prepublished on 2006 Jun. 17 as DOI 66/12/5989 [pii] 10.1158/0008-5472.CAN-05-4583.
23. Dassie J P, Liu X Y, Thomas G S, et al. Systemic administration of optimized aptamer-siRNA chimeras promotes regression of PSMA-expressing tumors. Nat Biotechnol. 2009; 27(9):839-849. Prepublished on 2009 Aug. 25 as DOI nbt.1560 [pii] 10.1038/nbt.1560.
24. De Fougerolles A. R. (2008) Delivery vehicles for small interfering RNA in vivo. Human Gene Therpay, 19, 125-132.
25. Dector M. A., Romero P., Lopez S., Arias C. F. (2002) Rotavirus gene silencing by small interfering RNAs. EMBO J 3, 1175-1180
26. Ding, B. B., et al., Constitutively activated STAT3 promotes cell proliferation and survival in the activated B-cell subtype of diffuse large B-cell lymphomas. Blood, 2008. 111(3): p. 1515-23.
27. Do R K, Hatada E, Lee H, Tourigny M R, Hilbert D, Chen-Kiang S. Attenuation of apoptosis underlies B lymphocyte stimulator enhancement of humoral immune response. J Exp Med. 2000; 192(7):953-964. Prepublished on 2000 Oct. 4 as DOI.
28. Domen, J., K. L. Gandy, and I. L. Weissman, Systemic overexpression of BCL-2 in the hematopoietic system protects transgenic mice from the consequences of lethal irradiation. Blood, 1998. 91(7): p. 2272-82.
29. Elbashir S. M., Harborth J., Lendeckel W., Yalcin A., Weber K., Tuschl T. (2001). Duplexes of 21-nucleotide RNAs mediate RNA interference in cultured mammalian cells. Nature, 411, 494-498.
30. Elbashir, S. M., et al., Duplexes of 21-nucleotide RNAs mediate RNA interference in cultured mammalian cells. Nature, 2001. 411(6836): p. 494-8.
31. Feugier, P., et al., Long-term results of the R-CHOP study in the treatment of elderly patients with diffuse large B-cell lymphoma: a study by the Groupe d'Etude des Lymphomes de l'Adulte. J Clin Oncol, 2005. 23(18): p. 4117-26.
32. Fire A., Xu S., Montgomery M. K., Kostas S. A., Driver S. E., Mello C. C. (1998). Potent and specific genetic interference by double-stranded RNA in Caenorhabditis elegans. Nature, 391, 806-811.
33. Friedberg, J. W. and R. I. Fisher, Diffuse large B-cell NHL. Cancer Treat Res, 2006. 131: p. 121-40.
34. Friedberg, J. W. and R. I. Fisher, Diffuse large B-cell lymphoma. Hematol Oncol Clin North Am, 2008. 22(5): p. 941-52, ix.
35. Fu L, Lin-Lee Y C, Pham L V, Tamayo A T, Yoshimura L C, Ford R J. BAFF-R promotes cell proliferation and survival through interaction with IKKbeta and NF-kappaB/c-Rel in the nucleus of normal and neoplastic B-lymphoid cells. Blood. 2009; 113(19):4627-4636. Prepublished on 2009 Mar. 5 as DOI blood-2008-10-183467 [pii] 10.1182/blood-2008-10-183467.
36. Gold, L., et al., Diversity of oligonucleotide functions. Annu Rev Biochem, 1995. 64: p. 763-97.
37. Ge Q., McManus M. T., Nguyen T., Shen C. H., Sharp P. A., Eisen H. N., Chen J. (2003) RNA interference of influenza virus production by directly targeting mRNA for degradation and indirectly inhibiting all viral RNA transcription. Proc Natl Acad Sci USA, 100, 2718-2723
38. Goossens T., Klein U. & Küppers R. (1998) Frequent occurrence of deletions and duplications during somatic hypermutation: implications for oncogene translocations and heavy chain disease. Proc. Natl Acad. Sci. USA 95, 2463-2468.
39. Gross J A, Johnston J, Mudri S, et al. TACI and BCMA are receptors for a TNF homologue implicated in B-cell autoimmune disease. Nature. 2000; 404(6781):995-999. Prepublished on 2000 May 9 as DOI 10.1038/35010115.
40. Grosshans H., Filipowicz W. (2008) The expanding world of small RNAs. Nature, 451, 414
41. Hannon, G. J. and J. J. Rossi, Unlocking the potential of the human genome with RNA interference. Nature, 2004. 431(2006): p. 371-8.
42. Hannon G. J. (2002). RNA interference. Nature, 418, 244-251.
43. He B, Chadburn A, Jou E, Schattner E J, Knowles D M, Cerutti A. Lymphoma B cells evade apoptosis through the TNF family members BAFF/BLyS and APRIL. J Immunol. 2004; 172(5):3268-3279. Prepublished on 2004 Feb. 24 as DOI.
44. Neale, B. S., et al., siRNA target site secondary structure predictions using local stable substructures. Nucleic Acids Res, 2005. 33(3): p. e30.
45. Hossbach, M., et al., Gene silencing with siRNA duplexes composed of target-mRNA-complementary and partially palindromic or partially complementary single-stranded siRNAs. RNA Biol, 2006. 3(2): p. 82-9.
46. Hughes B. (2008). 2007 FDA drug approvals: a year of flux. Nature Reviews: Drug Discovery, 7:106-109.
47. Jackson A. L., Bartz S. R., Schelter J., Kobayashi S. V., Burchard J., Mao M., Li B., Cavet G., Linsley P. S. (2003) Expression profiling reveals off-target gene regulation by RNAi. Nat Biotechnol, 21, 635-637
48. Jackson, A. L., et al., Position-specific chemical modification of siRNAs reduces "off-target" transcript silencing. RNA, 2006. 12(7): p. 1197-205.
49. Jemal A, Siegel R, Ward E, Hao Y, Xu J, Thun M J. Cancer statistics, 2009. CA Cancer J Clin. 2009; 59(4):225-249.
50. Jia Q., Sun R. (2003) Inhibition of gamma-herpesvirus replication by RNA interference. J Virol 77, 3301-3306.
51. Ju Z L, Shi G Y, Zuo J X, Zhang J W. Unexpected development of autoimmunity in BAFF-R-mutant MRL-lpr mice. Immunology. 2007; 120(2):281-289. Prepublished on 2006 Nov. 1 as DOI IMM2500 [pii] 10.1111/j.1365-2567.2006.02500.x.
52. Kayagaki N., Yan M., Seshasayee D., Wang H., Lee W., French D. M., Grewal I. S., Cochran A. G., Gordon N. C., Yin J., et al. (2002) BAFF/BLyS receptor 3 binds the B cell survival factor BAFF ligand through a discrete surfaceloop and promotes processing of NF-kB2. Immunity, 17, 515-524.
53. Kern C, Cornuel J F, Billard C, et al. Involvement of BAFF and APRIL in the resistance to apoptosis of B-CLL through an autocrine pathway. Blood.

54. 2003-02-0540 [pii]. Kim et al., (2005) Nucleic Acids Res, 33:4140-56
55. Kim D. H., Behlke M. A., Rose S. D., Chang M. S., Choi S., Rossi J. J. (2005) Synthetic dsRNA Dicer substrates enhance RNAi potency and efficacy. *Nat. Biotechnol.*, 23, 222.
56. Khare S D, Sarosi I, Xia X Z, et al. Severe B cell hyperplasia and autoimmune disease in TALL-1 transgenic mice. *Proc Natl Acad Sci USA.* 2000; 97(7):3370-3375. Prepublished on 2000 Mar. 15 as DOI 10.1073/pnas.050580697 050580697 [Pii].
57. Kortylewski M, Yu H. Role of Stat3 in suppressing anti-tumor immunity. *Curr Opin Immunol.* 2008; 20(2):228-233. Prepublished on 2008 May 16 as DOI S0952-7915 (08)00034-4 [pii] 10.1016/j.coi.2008.03.010.
58. Kueppers R. (2005). Mechanisms of B cell lymphoma pathogenesis. *Nature Reviews: Cancer,* 5:251-262.
59. Kueppers R., Dalla-Favera R. (2001) Mechanisms of chromosomal translocations in B-cell lymphomas. *Oncogene,* 20, 5580-5594.
60. Kumar P., Wu H., McBride J. L., Jung K-E., Kim M. H., Davidson B. L., Lee S. K., Shankar P., Manjunath N. (2007) Transvascular delivery of small interfering RNA to the central nervous system. *Nature,* 448, 39-43.
61. Kumar P., Wu H., McBride J. L., Jung K. E., Kim M. H., Davidson B. L., Lee S. K., Shankar P., Manjunath N. (2007). Transvascular delivery of small interfering RNA to the central nervous system. *Nature,* 448, 39-43.
62. Laabi Y., Gras M. P., Carbonnel F., et al. (1992) A new gene, BCM, on chromosome 16 is fused to the interleukin 2 gene by a t(4;16)(q26;p13) translocation in a malignant T cell lymphoma. *EMBO J,* 11, 3897-3904.
63. Lai R, Rassidakis G Z, Medeiros L J, Leventaki V, Keating M, McDonnell T J. Expression of STAT3 and its phosphorylated forms in mantle cell lymphoma cell lines and tumours. *J Pathol.* 2003; 199(1):84-89. Prepublished on 2002 Dec. 11 as DOI 10.1002/path.1253.
64. Leonard J P, Schattner E J, Coleman M. Biology and management of mantle cell lymphoma. *Curr Opin Oncol.* 2001; 13(5):342-347. Prepublished on 2001 Sep. 14 as DOI.
65. Lu P. Y., Woodle M. C. (2008) Delivering Small Interfering RNA for Novel Therapeutics. *Methods in Molecular Biology (Drug Delivery Systems),* 437, 93
66. Lyu, M. A., et al., The rGel/BLyS fusion toxin specifically targets malignant B cells expressing the BLyS receptors BAFF-R, TACI, and BCMA. Mol Cancer Ther, 2007. 6(2): p. 460-70.
67. Mackay F, Schneider P. Cracking the BAFF code. *Nat Rev Immunol.* 2009; 9(7):491-502. Prepublished on 2009 Jun. 13 as DOI nri2572 [pii] 10.1038/nri2572.
68. Mackay F, Woodcock S A, Lawton P, et al. Mice transgenic for BAFF develop lymphocytic disorders along with autoimmune manifestations. *J Exp Med.* 1999; 190(11): 1697-1710. Prepublished on 1999 Dec. 10 as DOI McNamara, J. O., 2nd, et al., *Cell type-specific delivery of siRNAs with aptamer-siRNA chimeras.* Nat Biotechnol, 2006. 24(8): p. 1005-15.
69. Makin, G. and J. A. Hickman, Apoptosis and cancer chemotherapy. Cell Tissue Res, 2000. 301(1): p. 143-52.
70. Matranga C, Tomari Y, Shin C, Bartel D P, Zamore P D. Passenger-strand cleavage facilitates assembly of siRNA into Ago2-containing RNAi enzyme complexes. *Cell.* 2005; 123(4):607-620. Prepublished on 2005 Nov. 8 as DOI S0092-8674(05)00922-0 [pii] 10.1016/j.cell.2005.08.044.
71. Meister G, Landthaler M, Patkaniowska A, Dorsett Y, Teng G, Tuschl T. Human Argonaute2 mediates RNA cleavage targeted by miRNAs and siRNAs. Mol Cell. 2004; 15(2):185-197. Prepublished on 2004 Jul. 21 as DOI 10.1016/j.molcel.2004.07.007 S1097276504004150 [pii].
72. Monti, S., et al., Molecular profiling of diffuse large B-cell lymphoma identifies robust subtypes including one characterized by host inflammatory response. Blood, 2005. 105(5): p. 1851-61.
73. Moore P A, Belvedere O, Orr A, et al. BLyS: member of the tumor necrosis factor family and B lymphocyte stimulator. *Science.* 1999; 285(5425):260-263. Prepublished on 1999 Jul. 10 as DOI 7659 [pii].
74. Nakamura N, Hase H, Sakurai D, et al. Expression of BAFF-R (BR 3) in normal and neoplastic lymphoid tissues characterized with a newly developed monoclonal antibody. *Virchows Arch.* 2005; 447(1):53-60. Prepublished on 2005 Jul. 19 as DOI 10.1007/s00428-005-1275-6.
75. Nardelli B, Belvedere O, Roschke V, et al. Synthesis and release of B-lymphocyte stimulator from myeloid cells. *Blood.* 2001; 97(1):198-204. Prepublished on 2001 Jan. 3 as DOI
76. Nimmanapalli R., Lyu M. A., Du M., Keating M. J., Rosenblum M. G., Gandhi V. (2007) The growth factor fusion construct containing B-lymphocyte stimulator (BLyS) and the toxin rGel induces apoptosis specifically in BAFFR-positive CLL cells. *Blood,* 109, 2557-2564.
77. Novak A J, Grote D M, Stenson M, et al. Expression of BLyS and its receptors in B-cell non-Hodgkin lymphoma: correlation with disease activity and patient outcome. *Blood.* 2004; 104(8):2247-2253. Prepublished on 2004 Jul. 15 as DOI 10.1182/blood-2004-02-0762
78. 2004-02-0762 [pii].Ohki E. C., Tilkins M. L., Ciccarone V. C., Price P. J. (2001) Improving the transfection efficiency of postmitotic neurons. *J Neurosci Methods,* 112, 95-99.
79. Oren D.a., Li Y., Volovik Y., Morris T. S., Dharia C., Das K., Galperina O., Gentz R., Arnold E. (2002) Structural basis of BLyS receptor recognition. *Nat. Struct. Biol.* 9, 288-292
80. Ortega-Paino E., Fransson J., Ek S., Borrebaeck C. A. K. (2008) Functionally associated targets in mantle cell lymphoma as defined by DNA microarrays and RNA interference. *Blood,* 111, 1617-1624.
81. Paddison P. J., Vogt P. K. (2008) RNA Interference, *Current Topics in Microbiology and Immunology.* 320 (Springer)
82. Pai S. I., Lin Y. Y., Macaes B., Meneshian A., Hung C. F., Wu T. C. (2006) Prospects of RNA interference therapy for cancer. *Gene Ther* 13, 464-477
83. Persky, D. O., *Dx/Rx: Lymphoma.* Vol. First edition. 2007: Jones and Bartlett Publishers Inc. p 85-99.
84. Pettersen E. F., Goddard T. D., Huang C. C., Couch G. S., Greenblatt D. M., Meng E. C., Ferrin T. E. (2004) UCSF Chimera—A visualization system for exploratory research analysis *J Comput. Chem.* 25, 1605-1612
85. Pei, Y. and T. Tuschl, On the art of identifying effective and specific siRNAs. Nat Methods, 2006. 3(9): p. 670-6.
86. Polo, J. M., et al., Specific peptide interference reveals BCL6 transcriptional and oncogenic mechanisms in B-cell lymphoma cells. Nat Med, 2004. 10(12): p. 1329-35.
87. Ramanarayanan, J., et al., Pro-apoptotic therapy with the oligonucleotide Genasense (oblimersen sodium) targeting Bcl-2 protein expression enhances the biological anti-tumour activity of rituximab. Br J Haematol, 2004. 127(5): p. 519-30.
88. Randall G., Grakoui A., Rice C. M. (2003) Clearance of replicating hepatitis C virus replicon RNAs in cell culture by small interfering RNAs. Proc Natl Acad Sci USA, 100, 235-240
89. Raoul C., Barker S. D., Aebischer P. (2006) Viral-based modeling and correction of neurodegenerative diseases by RNA interference. Gene Ther, 13, 487-495
90. Reed, J. C., Mechanisms of Bcl-2 family protein function and dysfunction in health and disease. Behring Inst Mitt, 1996(97): p. 72-100.
91. Rose, S. D., et al., Functional polarity is introduced by Dicer processing of short substrate RNAs. Nucleic Acids Res, 2005. 33(13): p. 4140-56.
92. Rossi J. J. (2006) RNAi as a treatment for HIV-1 infection. Biotechniques, 40, 25-29
93. Russ, V., et al., Oligoethylenimine-grafted polypropylenimine dendrimers as degradable and biocompatible synthetic vectors for gene delivery. J Control Release, 2008. 132(2): p. 131-40.
94. Russ, V., et al., Novel degradable oligoethylenimine acrylate ester-based pseudodendrimers for in vitro and in vivo gene transfer. Gene Ther, 2008. 15(1): p. 18-29.
95. Schiemann B., Gommerman J. L., Vora K., Cachero T. G., Shulga-Morskaya S., Dobles M., Frew E., Scott M. L. (2001). An essential role for BAFF in the normal development of B cells through a BCMA-independent pathway. Science, 293, 2111-2114
96. Schneider P., MacKay F., Steiner V., et al. (1999) BAFF, a novel ligand of the tumor necrosis factor family, stimulates B cell growth. J Exp Med., 189, 1747-1756.
97. Schwarz D. S., Hutvagner G., Du T., Xu Z., Aronin N., Zamore P. D. (2003) Asymmetry in the assembly of the RNAi enzyme complex. Cell, 115, 199.
98. Shaffer, A. L., et al., A library of gene expression signatures to illuminate normal and pathological lymphoid biology. Immunol Rev, 2006. 210: p. 67-85.
99. Shulga-Morskaya S, Dobles M, Walsh M E, et al. B cell-activating factor belonging to the TNF family acts through separate receptors to support B cell survival and T cell-independent antibody formation. J Immunol. 2004; 173(4):2331-2341. Prepublished on 2004 Aug. 6 as DOI 173/4/2331 [pii].
100. Simeoni F., Morris M. C., Heitz F., Divita G. (2005) Peptide-based strategy for siRNA delivery into mammalian cells. Methods Mol Biol, 309, 251-260
101. Song J. J. et al. (2003) The crystal structure of the Argonaute2 PAZ domain reveals an RNA binding motif in RNAi effector complexes, Nat. Struct. Biol., 10, 1026.
102. Tecchio C, Nadali G, Scapini P, et al. High serum levels of B-lymphocyte stimulator are associated with clinical-pathological features and outcome in classical Hodgkin lymphoma. Br J Haematol. 2007; 137(6):553-559. Prepublished on 2007 Jun. 2 as DOI BJH6615 [pii] 10.1111/j.1365-2141.2007.06615.x.
103. Thompson J. S., Bixler S. A., Qian F., et al. (2001) BAFF-R, a newly identified TNF receptor that specifically interacts with BAFF. Science, 293, 2108-2111.
104. Thompson J S, Schneider P, Kalled S L, et al. BAFF binds to the tumor necrosis factor receptor-like molecule B cell maturation antigen and is important for maintaining the peripheral B cell population. J Exp Med. 2000; 192(1): 129-135. Prepublished on 2000 Jul. 6 as DOI.
105. Tsujimoto Y., Gorham J., Cossman J., Jaffe E. & Croce C. M. (1985) The t(14;18) chromosome translocations involved in B-cell neoplasms result from mistakes in VDJ joining. Science 229, 1390-1393.
106. Tuerk, C. and L. Gold, Systematic evolution of ligands by exponential enrichment: RNA ligands to bacteriophage T4 DNA polymerase. Science, 1990. 249(4968): p. 505-10.
107. von Bulow G. U., Bram R. J. (1997) NF-AT activation induced by a CAML-interacting member of the tumor necrosis factor receptor superfamily. Science, 278, 138-141.
108. Vose J M. Current approaches to the management of non-Hodgkin's lymphoma. Semin Oncol. 1998; 25(4):483-491. Prepublished on 1998 Sep. 5 as DOI.
109. Wen X, Lyu M A, Zhang R, et al. Biodistribution, Pharmacokinetics, and Nuclear Imaging Studies of (111)In-labeled rGel/BLyS Fusion Toxin in SCID Mice Bearing B Cell Lymphoma. Mol Imaging Biol. Prepublished on 2010 Aug. 6 as DOI 10.1007/s11307-010-0391-0.
110. Williams M E, Densmore J J. Biology and therapy of mantle cell lymphoma. Curr Opin Oncol. 2005; 17(5):425-431. Prepublished on 2005 Aug. 12 as DOI 00001622-200509000-00002 [pii].
111. Wilson, C. and A. D. Keefe, Building oligonucleotide therapeutics using non-natural chemistries. Curr Opin Chem Biol, 2006. 10(6): p. 607-14.
112. Yan M., Brady J. R., Chan B., Lee W. P., Hsu B., Harless S., et al. (2001) Identification of a novel receptor for B lymphocyte stimulator that is mutated in a mouse strain with severe B cell deficiency. Curr Biol, 11, 1547-52
113. Yu, H. and R. Jove, The STATs of cancer—new molecular targets come of age. Nat Rev Cancer, 2004. 4(2): p. 97-105.
114. Yu H, Pardoll D, Jove R. STATs in cancer inflammation and immunity: a leading role for STAT3. Nat Rev Cancer. 2009; 9(11):798-809. Prepublished on 2009 Oct. 24 as DOI nrc2734 [pii] 10.1038/nrc2734.
115. Zhang, L., et al., Tumor targeting of vincristine by mBAFF-modified PEG liposomes in B lymphoma cells. Cancer Lett, 2008. 269(1):26-36.
116. Zhou, J., et al., Selection, characterization and application of new RNA HIV gp 120 aptamers for facile delivery of Dicer substrate siRNAs into HIV infected cells. Nucleic Acids Res, 2009.
117. Zhou J, Rossi J J. The therapeutic potential of cell-internalizing aptamers. Curr Top Med Chem. 2009; 9(12): 1144-1157. Prepublished on 2009 Oct. 29 as DOI.
118. Zhou J, Li H, Li S, Zaia J, Rossi J J. Novel dual inhibitory function aptamer-siRNA delivery system for HIV-1 therapy. Mol Ther. 2008; 16(8):1481-1489. Prepublished on 2008 May 8 as DOI mt200892 [pii]10.1038/mt.2008.92.

What is claimed is:

1. A method for treating a B cell malignancy in a cancer patient comprising administering a therapeutically effective amount of a therapeutic composition, the therapeutic composition comprising a B cell specific aptamer-siRNA chimera comprising an RNA aptamer comprising an RNA molecule having the sequence SEQ ID NO:9, SEQ ID NO:10 or SEQ ID NO:11 that binds BAFF-R, and an siRNA molecule conjugated to the RNA aptamer via a nucleotide linker.

2. The method of claim 1, wherein the aptamer, upon binding BAFF-R, blocks BAFF ligand mediated cell proliferation.

3. The method of claim 1, wherein the siRNA molecule suppresses expression of a target oncogene when internalized by a B cell.

4. The method of claim 3, wherein the target oncogene is selected from Bcl6, Bcl2, STAT3, Cyclin D1, Cyclin E2 and c-myc.

5. The method of claim 1, wherein the siRNA molecule comprises a sense strand SEQ ID NO:7 and an antisense strand SEQ ID NO:8.

6. The method of claim 1, wherein the siRNA molecule is a bifunctional siRNA molecule which suppresses expression of two target oncogenes when internalized by the B cell.

7. The method of claim 6, wherein the two target oncogenes are selected from Bcl6, Bcl2, STAT3, Cyclin D1, Cyclin E2 and c-myc.

8. The method of claim 1, wherein the nucleotide linker is a uracil linker comprising approximately 2-10 uracils.

9. The method of claim 1, wherein the chimera has
a sense strand selected from SEQ ID NO:37, SEQ ID NO:38 or SEQ ID NO:39, and an antisense strand having the sequence SEQ ID NO:40;
a sense strand selected from SEQ ID NO:41 or SEQ ID NO:42 and an antisense strand having the sequence SEQ ID NO:43;
a sense strand having the sequence SEQ ID NO:46 and an antisense strand having the sequence SEQ ID NO:47; or
a sense strand having the sequence SEQ ID NO:49 and an antisense strand having the sequence SEQ ID NO:48.

10. A method for treating a B cell malignancy in a cancer patient comprising administering a therapeutically effective amount of a therapeutic composition, the therapeutic composition comprising a B cell specific RNA aptamer comprising an RNA molecule that binds to BAFF-R having the sequence SEQ ID NO:9, SEQ ID NO:10 or SEQ ID NO:11.

11. The method of claim 10, wherein the RNA molecule is conjugated, via a nucleotide linker, to an siRNA molecule that suppresses expression of one or more target oncogenes in one or more B cells.

12. The method of claim 11, wherein the nucleotide linker is a uracil linker comprising approximately 2-10 uracils.

13. The method of claim 11, wherein the one or more target oncogenes are selected from Bcl6, Bcl2, STAT3, Cyclin D1, Cyclin E2 and c-myc.

14. The method of claim 11, wherein the siRNA molecule is a bifunctional siRNA molecule which suppresses expression of two target oncogenes when internalized by the B cell.

15. The method of claim 14, wherein the two target oncogenes are selected from Bcl6, Bcl2, STAT3, Cyclin D1, Cyclin E2 and c-myc.

16. A method for treating a B cell malignancy in a cancer patient comprising administering a therapeutically effective amount of a therapeutic composition, the therapeutic composition comprising a B cell specific aptamer-siRNA chimera comprising an RNA aptamer that binds BAFF-R, and an siRNA molecule comprising a sense strand SEQ ID NO:7 and an antisense strand SEQ ID NO:8 conjugated to the RNA aptamer via a nucleotide linker.

17. The method of claim 16, wherein the aptamer, upon binding BAFF-R, blocks BAFF ligand mediated cell proliferation.

18. The method of claim 16, wherein the nucleotide linker is a uracil linker comprising approximately 2-10 uracils.

19. The method of claim 16, wherein the siRNA molecule is a bifunctional siRNA molecule which suppresses expression of one or more target oncogenes when internalized by the B cell.

20. The method of claim 19, wherein the one or more target oncogenes are selected from Bcl6, Bcl2, STAT3, Cyclin D1, Cyclin E2 and c-myc.

* * * * *

SEQUENCE LISTING

<160> NUMBER OF SEQ ID NOS: 85

<210> SEQ ID NO 1

<211> LENGTH: 25
<212> TYPE: RNA
<213> ORGANISM: Artificial Sequence
<220> FEATURE:
<223> OTHER INFORMATION: Synthetic

<400> SEQUENCE: 1
ccacagaugu gaaguucauu uccaa                                          25

<210> SEQ ID NO 2
<211> LENGTH: 27
<212> TYPE: RNA
<213> ORGANISM: Artificial Sequence
<220> FEATURE:
<223> OTHER INFORMATION: Synthetic

<400> SEQUENCE: 2
uuggaaauga acuucacauc uguggca                                        27

<210> SEQ ID NO 3
<211> LENGTH: 27
<212> TYPE: RNA
<213> ORGANISM: Artificial Sequence
<220> FEATURE:
<223> OTHER INFORMATION: Synthetic

<400> SEQUENCE: 3
ugugccacag augugaaguu cauuucc                                        27

<210> SEQ ID NO 4
<211> LENGTH: 25
<212> TYPE: RNA
<213> ORGANISM: Artificial Sequence
<220> FEATURE:
<223> OTHER INFORMATION: Synthetic

<400> SEQUENCE: 4
aaaugaacuu cacaucugug gcaca                                          25

<210> SEQ ID NO 5
<211> LENGTH: 25
<212> TYPE: RNA
<213> ORGANISM: Artificial Sequence
<220> FEATURE:
<223> OTHER INFORMATION: Synthetic

<400> SEQUENCE: 5
cuccagauuc caagcacauu gugaa                                          25

<210> SEQ ID NO 6
<211> LENGTH: 27
<212> TYPE: RNA
<213> ORGANISM: Artificial Sequence
<220> FEATURE:
<223> OTHER INFORMATION: Synthetic

<400> SEQUENCE: 6
uucacaaugu gcuuggaauc uggagca                                        27

<210> SEQ ID NO 7
<211> LENGTH: 27
<212> TYPE: RNA
<213> ORGANISM: Artificial Sequence
<220> FEATURE:
<223> OTHER INFORMATION: Synthetic

<400> SEQUENCE: 7

```
gagaacggaa gcugcagaaa gauacga                                              27

<210> SEQ ID NO 8
<211> LENGTH: 25
<212> TYPE: RNA
<213> ORGANISM: Artificial Sequence
<220> FEATURE:
<223> OTHER INFORMATION: Synthetic

<400> SEQUENCE: 8
guaucuuucu gcagcuuccg uucuc                                                25

<210> SEQ ID NO 9
<211> LENGTH: 81
<212> TYPE: RNA
<213> ORGANISM: Artificial Sequence
<220> FEATURE:
<223> OTHER INFORMATION: Synthetic

<400> SEQUENCE: 9
gggaggacga ugcgggaggc ucaacaauga uagagcccgc aauguugaua guugugccca          60
gucugcagac gacucgcccg a                                                    81

<210> SEQ ID NO 10
<211> LENGTH: 81
<212> TYPE: RNA
<213> ORGANISM: Artificial Sequence
<220> FEATURE:
<223> OTHER INFORMATION: Synthetic

<400> SEQUENCE: 10
gggaggacga ugcggauaac uauugugcua gagggcuuau uuaugugagc cgguugauag          60
uugcgcagac gacucgcccg a                                                    81

<210> SEQ ID NO 11
<211> LENGTH: 80
<212> TYPE: RNA
<213> ORGANISM: Artificial Sequence
<220> FEATURE:
<223> OTHER INFORMATION: Synthetic

<400> SEQUENCE: 11
gggaggacga ugcggauccu ccgaaggucg cgccaacguc acacauuaag cuuuuguucg          60
ucugcagacg acucgcccga                                                      80

<210> SEQ ID NO 12
<211> LENGTH: 15
<212> TYPE: RNA
<213> ORGANISM: Artificial Sequence
<220> FEATURE:
<223> OTHER INFORMATION: Synthetic

<400> SEQUENCE: 12
gggaggacga ugcgg                                                           15

<210> SEQ ID NO 13
<211> LENGTH: 16
<212> TYPE: RNA
<213> ORGANISM: Artificial Sequence
<220> FEATURE:
<223> OTHER INFORMATION: Synthetic

<400> SEQUENCE: 13
```
cagacgacuc gcccga                                                        16

<210> SEQ ID NO 14
<211> LENGTH: 50
<212> TYPE: RNA
<213> ORGANISM: Artificial Sequence
<220> FEATURE:
<223> OTHER INFORMATION: Synthetic

<400> SEQUENCE: 14
gaggcucaac aaugauagag cccgcaaugu ugauaguugu gcccagucug               50

<210> SEQ ID NO 15
<211> LENGTH: 50
<212> TYPE: RNA
<213> ORGANISM: Artificial Sequence
<220> FEATURE:
<223> OTHER INFORMATION: Synthetic

<400> SEQUENCE: 15
gaggcucggc uuaguaagua aagauugagc ccgcaugacg cuccgagugc               50

<210> SEQ ID NO 16
<211> LENGTH: 50
<212> TYPE: RNA
<213> ORGANISM: Artificial Sequence
<220> FEATURE:
<223> OTHER INFORMATION: Synthetic

<400> SEQUENCE: 16
ggaggcucuu agagcccugc aucuuggaaa auaggauaag gcccgugcac               50

<210> SEQ ID NO 17
<211> LENGTH: 49
<212> TYPE: RNA
<213> ORGANISM: Artificial Sequence
<220> FEATURE:
<223> OTHER INFORMATION: Synthetic

<400> SEQUENCE: 17
gaggcucgug gauguuuauc gaagagcccg caauccgguu ugucuggug                49

<210> SEQ ID NO 18
<211> LENGTH: 50
<212> TYPE: RNA
<213> ORGANISM: Artificial Sequence
<220> FEATURE:
<223> OTHER INFORMATION: Synthetic

<400> SEQUENCE: 18
gagguucggu cauauagggg uacugaaccc gcgucggugu ucgguuuggc               50

<210> SEQ ID NO 19
<211> LENGTH: 50
<212> TYPE: RNA
<213> ORGANISM: Artificial Sequence
<220> FEATURE:
<223> OTHER INFORMATION: Synthetic

<400> SEQUENCE: 19
ugaggcucau agagcaccgc aaagauagaa aguuguugcc aucgauagug               50

<210> SEQ ID NO 20
<211> LENGTH: 50
<212> TYPE: RNA
<213> ORGANISM: Artificial Sequence
<220> FEATURE:
<223> OTHER INFORMATION: Synthetic

<400> SEQUENCE: 20
ugaggcucga uuagagguug gucucuugug agcccguauc gcgaaugcug          50

<210> SEQ ID NO 21
<211> LENGTH: 50
<212> TYPE: RNA
<213> ORGANISM: Artificial Sequence
<220> FEATURE:
<223> OTHER INFORMATION: Synthetic

<400> SEQUENCE: 21
uuugaggcuc gcgacuacga agagcaaacc guaucgcguu gcagcaugga          50

<210> SEQ ID NO 22
<211> LENGTH: 50
<212> TYPE: RNA
<213> ORGANISM: Artificial Sequence
<220> FEATURE:
<223> OTHER INFORMATION: Synthetic

<400> SEQUENCE: 22
cagguuuccc guuugucggu ucaaacggcg uccugccguu aguuggugug          50

<210> SEQ ID NO 23
<211> LENGTH: 50
<212> TYPE: RNA
<213> ORGANISM: Artificial Sequence
<220> FEATURE:
<223> OTHER INFORMATION: Synthetic

<400> SEQUENCE: 23
uuuccccggc caaguagcug ggcguccgca uuccucagga ccguacgccg          50

<210> SEQ ID NO 24
<211> LENGTH: 52
<212> TYPE: RNA
<213> ORGANISM: Artificial Sequence
<220> FEATURE:
<223> OTHER INFORMATION: Synthetic

<400> SEQUENCE: 24
uuucccuagg aucacaucga ucuuaggcgu ccgcacacgu caaccucccg ug       52

<210> SEQ ID NO 25
<211> LENGTH: 50
<212> TYPE: RNA
<213> ORGANISM: Artificial Sequence
<220> FEATURE:
<223> OTHER INFORMATION: Synthetic

<400> SEQUENCE: 25
aaucgccgaa ugaggcucuu agagcauucg gcgcgcaaac caggacacgc          50

<210> SEQ ID NO 26
<211> LENGTH: 50
<212> TYPE: RNA
<213> ORGANISM: Artificial Sequence
<220> FEATURE:
<223> OTHER INFORMATION: Synthetic

<400> SEQUENCE: 26
ucaaucgcgu aauaacgcgu uugugaacug aucuaauccg gucugagguug         50

<210> SEQ ID NO 27
<211> LENGTH: 50
<212> TYPE: RNA
<213> ORGANISM: Artificial Sequence
<220> FEATURE:
<223> OTHER INFORMATION: Synthetic

<400> SEQUENCE: 27
auaacuauug ugcuagaggg cuuauuuaug ugagccgguu gauaguugcg         50

<210> SEQ ID NO 28
<211> LENGTH: 50
<212> TYPE: RNA
<213> ORGANISM: Artificial Sequence
<220> FEATURE:
<223> OTHER INFORMATION: Synthetic

<400> SEQUENCE: 28
augacugaca gggacuucuu ggcaauuuug cugcgaguuc acgguggcgc         50

<210> SEQ ID NO 29
<211> LENGTH: 50
<212> TYPE: RNA
<213> ORGANISM: Artificial Sequence
<220> FEATURE:
<223> OTHER INFORMATION: Synthetic

<400> SEQUENCE: 29
uuuacugacc guuuguagg uugguagccu ugcuucacaa gaagugugcg          50

<210> SEQ ID NO 30
<211> LENGTH: 50
<212> TYPE: RNA
<213> ORGANISM: Artificial Sequence
<220> FEATURE:
<223> OTHER INFORMATION: Synthetic

<400> SEQUENCE: 30
gacuuagaug ucacguugua uaaaucgguc guccucuggu acguacgcug         50

<210> SEQ ID NO 31
<211> LENGTH: 48
<212> TYPE: RNA
<213> ORGANISM: Artificial Sequence
<220> FEATURE:
<223> OTHER INFORMATION: Synthetic

<400> SEQUENCE: 31
gauaggacau gcgauucccg uuguuuacgg ucguuacuca ggucuggc           48

<210> SEQ ID NO 32
<211> LENGTH: 50
<212> TYPE: RNA
<213> ORGANISM: Artificial Sequence
<220> FEATURE:
<223> OTHER INFORMATION: Synthetic

<400> SEQUENCE: 32
uugauuguaa gaauugugca uaaggcauuu caccuccuag caacguggac         50

<210> SEQ ID NO 33
<211> LENGTH: 56
<212> TYPE: RNA
<213> ORGANISM: Artificial Sequence
<220> FEATURE:
<223> OTHER INFORMATION: Synthetic

```
<400> SEQUENCE: 33
cuuauggucu uuauuuguuu uuuuuuuucu cggacccgcc cgguucuug gucugc            56

<210> SEQ ID NO 34
<211> LENGTH: 51
<212> TYPE: RNA
<213> ORGANISM: Artificial Sequence
<220> FEATURE:
<223> OTHER INFORMATION: Synthetic

<400> SEQUENCE: 34
uguccgaauc ucgagaaacg ggauuccgcg uccgcgucau guguaguugg u                51

<210> SEQ ID NO 35
<211> LENGTH: 49
<212> TYPE: RNA
<213> ORGANISM: Artificial Sequence
<220> FEATURE:
<223> OTHER INFORMATION: Synthetic

<400> SEQUENCE: 35
auccuccgaa ggucgcgcca acgucacaca uuaagcuuuu guucgucug                  49

<210> SEQ ID NO 36
<211> LENGTH: 7
<212> TYPE: RNA
<213> ORGANISM: Artificial Sequence
<220> FEATURE:
<223> OTHER INFORMATION: Synthetic

<400> SEQUENCE: 36 gaggcuc                                                                7

<210> SEQ ID NO 37
<211> LENGTH: 108
<212> TYPE: RNA
<213> ORGANISM: Artificial Sequence
<220> FEATURE:
<223> OTHER INFORMATION: Synthetic

<400> SEQUENCE: 37
gggaggacga ugcgggaggc ucaacaauga uagagcccgc aauguugaua guugugccca      60
gucugcagac gacucgcccg auuccacaga ugugaaguuc auuccaa                   108

<210> SEQ ID NO 38
<211> LENGTH: 108
<212> TYPE: RNA
<213> ORGANISM: Artificial Sequence
<220> FEATURE:
<223> OTHER INFORMATION: Synthetic

<400> SEQUENCE: 38
gggaggacga ugcggauaac uauugugcua gagggcuuau uuaugugagc cgguugauag      60
uugcgcagac gacucgcccg auuccacaga ugugaaguuc auuccaa                   108

<210> SEQ ID NO 39
<211> LENGTH: 106
<212> TYPE: RNA
<213> ORGANISM: Artificial Sequence
<220> FEATURE:
<223> OTHER INFORMATION: Synthetic

<400> SEQUENCE: 39
```
ggaggacgau gcggauccuc cgaaggucgc gccaacguca cacauuaagc uuuguucgu    60 cugcagacga cucgcccgau uccacagaug ugaaguucau uuccaa    106

<210> SEQ ID NO 40
<211> LENGTH: 27
<212> TYPE: RNA
<213> ORGANISM: Artificial Sequence
<220> FEATURE:
<223> OTHER INFORMATION: Synthetic

<400> SEQUENCE: 40
uuggaaauga acuucacauc uguggca    27

<210> SEQ ID NO 41
<211> LENGTH: 110
<212> TYPE: RNA
<213> ORGANISM: Artificial Sequence
<220> FEATURE:
<223> OTHER INFORMATION: Synthetic

<400> SEQUENCE: 41
gggaggacga ugcgggaggc ucaacaauga uagagcccgc aauguugaua guugugccca    60
gucugcagac gacucgcccg auuugugcca cagaugugaa guucauuucc    110

<210> SEQ ID NO 42
<211> LENGTH: 110
<212> TYPE: RNA
<213> ORGANISM: Artificial Sequence
<220> FEATURE:
<223> OTHER INFORMATION: Synthetic

<400> SEQUENCE: 42
gggaggacga ugcggauaac uauugugcua gagggcuuau uuaugugagc cgguugauag    60
uugcgcagac gacucgcccg auuugugcca cagaugugaa guucauuucc    110

<210> SEQ ID NO 43
<211> LENGTH: 25
<212> TYPE: RNA
<213> ORGANISM: Artificial Sequence
<220> FEATURE:
<223> OTHER INFORMATION: Synthetic

<400> SEQUENCE: 43
aaaugaacuu cacaucugug gcaca    25

<210> SEQ ID NO 44
<211> LENGTH: 108
<212> TYPE: RNA
<213> ORGANISM: Artificial Sequence
<220> FEATURE:
<223> OTHER INFORMATION: Synthetic

<400> SEQUENCE: 44
gggaggacga ugcgggaggc ucaacaauga uagagcccgc aauguugaua guugugccca    60
gucugcagac gacucgcccg auucuccaga uuccaagcac auugugaa    108

<210> SEQ ID NO 45
<211> LENGTH: 27
<212> TYPE: RNA
<213> ORGANISM: Artificial Sequence
<220> FEATURE:
<223> OTHER INFORMATION: Synthetic

<400> SEQUENCE: 45

```
uucacaaugu gcuuggaauc uggagca                                              27

<210> SEQ ID NO 46
<211> LENGTH: 116
<212> TYPE: RNA
<213> ORGANISM: Artificial Sequence
<220> FEATURE:
<223> OTHER INFORMATION: Synthetic

<400> SEQUENCE: 46
gggaggacga ugcgggaggc ucaacaauga uagagcccgc aauguugaua guugugccca          60
gucugcagac gacucgcccg auuuuuuuug agaacggaag cugcagaaag aucga              116

<210> SEQ ID NO 47
<211> LENGTH: 25
<212> TYPE: RNA
<213> ORGANISM: Artificial Sequence
<220> FEATURE:
<223> OTHER INFORMATION: Synthetic

<400> SEQUENCE: 47
guaucuuucu gcagcuuccg uucuc                                                25

<210> SEQ ID NO 48
<211> LENGTH: 116
<212> TYPE: RNA
<213> ORGANISM: Artificial Sequence
<220> FEATURE:
<223> OTHER INFORMATION: Synthetic

<400> SEQUENCE: 48
gggaggacga ugcgggaggc ucaacaauga uagagcccgc aauguugaua guugugccca          60
gucugcagac gacucgcccg auuuuuuuuu cagucguauc uuucugcagc uuccgu             116

<210> SEQ ID NO 49
<211> LENGTH: 25
<212> TYPE: RNA
<213> ORGANISM: Artificial Sequence
<220> FEATURE:
<223> OTHER INFORMATION: Synthetic

<400> SEQUENCE: 49
ggaagcugca gaaagauacg acuga                                                25

<210> SEQ ID NO 50
<211> LENGTH: 23
<212> TYPE: DNA
<213> ORGANISM: Artificial Sequence
<220> FEATURE:
<223> OTHER INFORMATION: Synthetic

<400> SEQUENCE: 50
ctcctctccg gagcattttg ata                                                  23

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ttaaagacag tttttgggta atct                                                 24
```

```
<210> SEQ ID NO 52
<211> LENGTH: 18
<212> TYPE: DNA
<213> ORGANISM: Artificial Sequence
<220> FEATURE:
<223> OTHER INFORMATION: Synthetic

<400> SEQUENCE: 52
ggcgacctgg aagtccaa                                                       18

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
ccatcagcac cacagccttc                                                     20

<210> SEQ ID NO 54
<211> LENGTH: 32
<212> TYPE: DNA
<213> ORGANISM: Artificial Sequence
<220> FEATURE:
<223> OTHER INFORMATION: Synthetic

<400> SEQUENCE: 54
taatacgact cactataggg aggacgatgc gg                                       32

<210> SEQ ID NO 55
<211> LENGTH: 16
<212> TYPE: DNA
<213> ORGANISM: Artificial Sequence
<220> FEATURE:
<223> OTHER INFORMATION: Synthetic

<400> SEQUENCE: 55
tcgggcgagt cgtctg                                                         16

<210> SEQ ID NO 56
<211> LENGTH: 100
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(80)
<223> OTHER INFORMATION: n is a, c, g, or t

<400> SEQUENCE: 56
ccaagcttgc atgcctgcag nnnnnnnnnn nnnnnnnnnn nnnnnnnnnn nnnnnnnnnn         60
nnnnnnnnnn nnnnnnnnnn ggtaccgagc tcgaattccc                              100

<210> SEQ ID NO 57
<211> LENGTH: 117
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(97)
<223> OTHER INFORMATION: n is a, c, g, or t

<400> SEQUENCE: 57
```

```
taatacgact cactataggg aattcgagct cggtaccnnn nnnnnnnnnn nnnnnnnnnn    60
nnnnnnnnnn nnnnnnnnnn nnnnnnnnnn nnnnnnnctg caggcatgca agcttgg      117
```

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58

```
ccaagcttgc atgcctgcag                                                20
```

<210> SEQ ID NO 59
<211> LENGTH: 117
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(97)
<223> OTHER INFORMATION: n is a, c, g, or t

<400> SEQUENCE: 59

```
taatacgact cactataggg aattcgagct cggtaccnnn nnnnnnnnn nnnnnnnnnn     60 nnnnnnnnnn nnnnnnnnnn nnnnnnnnnn nnnnnnnctg caggcatgca agcttgg      117
```

<210> SEQ ID NO 60
<211> LENGTH: 117
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(80)
<223> OTHER INFORMATION: n is a, c, g, or t

<400> SEQUENCE: 60

```
ccaagcttgc atgcctgcag nnnnnnnnnn nnnnnnnnnn nnnnnnnnnn nnnnnnnnnn    60
nnnnnnnnnn nnnnnnnnnn ggtaccgagc tcgaattccc tatagtgagt cgtatta      117
```

<210> SEQ ID NO 61
<211> LENGTH: 100
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(80)
<223> OTHER INFORMATION: n is a, c, g, t or u

<400> SEQUENCE: 61

```
gggaauucga gcucggtacc nnnnnnnnnn nnnnnnnnnn nnnnnnnnnn nnnnnnnnnn    60
nnnnnnnnnn nnnnnnnnnn cugcaggcau gcaagcuugg                         100
```

<210> SEQ ID NO 62
<211> LENGTH: 37
<212> TYPE: DNA
<213> ORGANISM: Artificial Sequence
<220> FEATURE:
<223> OTHER INFORMATION: Synthetic

```
<400> SEQUENCE: 62
taatacgact cactataggg aattcgagct cggtacc                            37

<210> SEQ ID NO 63
<211> LENGTH: 35
<212> TYPE: RNA
<213> ORGANISM: Artificial Sequence
<220> FEATURE:
<223> OTHER INFORMATION: Synthetic

<400> SEQUENCE: 63
uuuuuuuuga gaacggaagc ugcagaaaga uacga                             35

<210> SEQ ID NO 64
<211> LENGTH: 25
<212> TYPE: RNA
<213> ORGANISM: Artificial Sequence
<220> FEATURE:
<223> OTHER INFORMATION: Synthetic

<400> SEQUENCE: 64
guaucuuucu gcagcuuccg uucuc                                        25

<210> SEQ ID NO 65
<211> LENGTH: 35
<212> TYPE: RNA
<213> ORGANISM: Artificial Sequence
<220> FEATURE:
<223> OTHER INFORMATION: Synthetic

<400> SEQUENCE: 65
uuuuuuuuuc agucguaucu uucugcagcu uccgu                             35

<210> SEQ ID NO 66
<211> LENGTH: 25
<212> TYPE: RNA
<213> ORGANISM: Artificial Sequence
<220> FEATURE:
<223> OTHER INFORMATION: Synthetic

<400> SEQUENCE: 66
ggaagcugca gaaagauacg acuga                                        25

<210> SEQ ID NO 67
<211> LENGTH: 50
<212> TYPE: DNA
<213> ORGANISM: Artificial Sequence
<220> FEATURE:
<223> OTHER INFORMATION: Synthetic

<400> SEQUENCE: 67
tgaggagctg agaacggaag ctgcagaaag atacgactga ggcgcctacc             50

<210> SEQ ID NO 68
<211> LENGTH: 25
<212> TYPE: RNA
<213> ORGANISM: Artificial Sequence
<220> FEATURE:
<223> OTHER INFORMATION: Synthetic

<400> SEQUENCE: 68
ggaagcugca gaaagauacg acuga                                        25

<210> SEQ ID NO 69
<211> LENGTH: 27
```

```
<212> TYPE: RNA
<213> ORGANISM: Artificial Sequence
<220> FEATURE:
<223> OTHER INFORMATION: Synthetic

<400> SEQUENCE: 69
ucagucguau cuuucugcag cuuccgu                                       27

<210> SEQ ID NO 70
<211> LENGTH: 21
<212> TYPE: RNA
<213> ORGANISM: Artificial Sequence
<220> FEATURE:
<223> OTHER INFORMATION: Synthetic

<400> SEQUENCE: 70
cggaagcugc agaaagauac g                                             21

<210> SEQ ID NO 71
<211> LENGTH: 21
<212> TYPE: RNA
<213> ORGANISM: Artificial Sequence
<220> FEATURE:
<223> OTHER INFORMATION: Synthetic

<400> SEQUENCE: 71
uaucuuucug cagcuuccgu u                                             21

<210> SEQ ID NO 72
<211> LENGTH: 22
<212> TYPE: RNA
<213> ORGANISM: Artificial Sequence
<220> FEATURE:
<223> OTHER INFORMATION: Synthetic

<400> SEQUENCE: 72
gaacggaagc ugcagaaaga ua                                            22

<210> SEQ ID NO 73
<211> LENGTH: 22
<212> TYPE: RNA
<213> ORGANISM: Artificial Sequence
<220> FEATURE:
<223> OTHER INFORMATION: Synthetic

<400> SEQUENCE: 73
ucuuucugca gcuuccguuc uc                                            22

<210> SEQ ID NO 74
<211> LENGTH: 23
<212> TYPE: RNA
<213> ORGANISM: Artificial Sequence
<220> FEATURE:
<223> OTHER INFORMATION: Synthetic

<400> SEQUENCE: 74
ggaagcugca gaaagauacg acu                                           23

<210> SEQ ID NO 75
<211> LENGTH: 23
<212> TYPE: RNA
<213> ORGANISM: Artificial Sequence
<220> FEATURE:
<223> OTHER INFORMATION: Synthetic

<400> SEQUENCE: 75
```

```
ucguaucuuu cugcagcuuc cgu                                              23
```

<210> SEQ ID NO 76
<211> LENGTH: 20
<212> TYPE: RNA
<213> ORGANISM: Artificial Sequence
<220> FEATURE:
<223> OTHER INFORMATION: Synthetic

<400> SEQUENCE: 76

```
ggaagcugca gaaagauacg                                                  20
```

<210> SEQ ID NO 77
<211> LENGTH: 20
<212> TYPE: RNA
<213> ORGANISM: Artificial Sequence
<220> FEATURE:
<223> OTHER INFORMATION: Synthetic

<400> SEQUENCE: 77

```
uaucuuucug cagcuuccgu                                                  20
```

<210> SEQ ID NO 78
<211> LENGTH: 19
<212> TYPE: RNA
<213> ORGANISM: Artificial Sequence
<220> FEATURE:
<223> OTHER INFORMATION: Synthetic

<400> SEQUENCE: 78

```
ggaagcugca gaaagauac                                                   19
```

<210> SEQ ID NO 79
<211> LENGTH: 19
<212> TYPE: RNA
<213> ORGANISM: Artificial Sequence
<220> FEATURE:
<223> OTHER INFORMATION: Synthetic

<400> SEQUENCE: 79

```
aucuuucugc agcuuccgu                                                   19
```

<210> SEQ ID NO 80
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: C at position 7 may be absent
<220> FEATURE:
<221> NAME/KEY: misc_feature
<222> LOCATION: (9)..(9)
<223> OTHER INFORMATION: U at position 9 may be absent

<400> SEQUENCE: 80

```
aaucgccgua au                                                          12
```

<210> SEQ ID NO 81
<211> LENGTH: 18
<212> TYPE: RNA
<213> ORGANISM: Artificial Sequence
<220> FEATURE:
<223> OTHER INFORMATION: Synthetic

<400> SEQUENCE: 81

```
gcaggagggc aguuugag                                                      18

<210> SEQ ID NO 82
<211> LENGTH: 21
<212> TYPE: RNA
<213> ORGANISM: Artificial Sequence
<220> FEATURE:
<223> OTHER INFORMATION: Synthetic

<400> SEQUENCE: 82
cgccucaguc guaucuuucu g                                                  21

<210> SEQ ID NO 83
<211> LENGTH: 19
<212> TYPE: RNA
<213> ORGANISM: Artificial Sequence
<220> FEATURE:
<223> OTHER INFORMATION: Synthetic

<400> SEQUENCE: 83
cauugaccuc aacuacaug                                                     19

<210> SEQ ID NO 84
<211> LENGTH: 19
<212> TYPE: RNA
<213> ORGANISM: Artificial Sequence
<220> FEATURE:
<223> OTHER INFORMATION: Synthetic

<400> SEQUENCE: 84
ucuccauggu ggugaagac                                                     19

<210> SEQ ID NO 85
<211> LENGTH: 153
<212> TYPE: PRT
<213> ORGANISM: Artificial Sequence
<220> FEATURE:
<223> OTHER INFORMATION: human recombinant B-cell activating factor

<400> SEQUENCE: 85
```

Met Ala Val Gln Gly Pro Glu Glu Thr Val Thr Gln Asp Cys Leu Gln
1               5                   10                  15

Leu Ile Ala Asp Ser Glu Thr Pro Thr Ile Gln Lys Gly Ser Tyr Thr
            20                  25                  30

Phe Val Pro Trp Leu Leu Ser Phe Lys Arg Gly Ser Ala Leu Glu Glu
        35                  40                  45

Lys Glu Asn Lys Ile Leu Val Lys Glu Thr Gly Tyr Phe Phe Ile Tyr
    50                  55                  60

Gly Gln Val Leu Tyr Thr Asp Lys Thr Tyr Ala Met Gly His Leu Ile
65                  70                  75                  80

Gln Arg Lys Lys Val His Val Phe Gly Asp Glu Leu Ser Leu Val Thr
                85                  90                  95

Leu Phe Arg Cys Ile Gln Asn Met Pro Glu Thr Leu Pro Asn Asn Ser
            100                 105                 110

Cys Tyr Ser Ala Gly Ile Ala Lys Leu Glu Glu Gly Asp Glu Leu Gln
        115                 120                 125

Leu Ala Ile Pro Arg Glu Asn Ala Gln Ile Ser Leu Asp Gly Asp Val
    130                 135                 140

Thr Phe Phe Gly Ala Leu Lys Leu Leu
145                 150